(12) United States Patent  
Okabe et al.

(10) Patent No.: US 8,991,203 B2  
(45) Date of Patent: Mar. 31, 2015

(54) ELECTROSTATIC ATOMIZING APPARATUS, APPLIANCE, AIR CONDITIONER, AND REFRIGERATOR

(75) Inventors: Makoto Okabe, Tokyo (JP); Katsumasa Sakamoto, Tokyo (JP); Reiji Morioka, Tokyo (JP); Masumi Handa, Tokyo (JP); Hiroshi Nakashima, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 25 days.

(21) Appl. No.: 13/246,191

(22) Filed: Sep. 27, 2011

(65) Prior Publication Data

US 2012/0017628 A1   Jan. 26, 2012

Related U.S. Application Data

(62) Division of application No. 13/260,402, filed as application No. PCT/JP2010/052444 on Feb. 18, 2010.

(30) Foreign Application Priority Data

Mar. 27, 2009   (JP) .................. 2009-079584

(51) Int. Cl.  
*A23L 3/36* (2006.01)  
*F24F 6/12* (2006.01)  
(Continued)

(52) U.S. Cl.  
CPC . *F24F 6/12* (2013.01); *B05B 5/057* (2013.01); *B05B 5/16* (2013.01); *B05B 5/0255* (2013.01);  
(Continued)

(58) Field of Classification Search  
USPC ................. 62/3.2, 3.6, 78, 98, 303, 314, 373; 239/690, 690.1, 697, 698, 704, 706, 239/708  
See application file for complete search history.

(56) References Cited

U.S. PATENT DOCUMENTS

| 3,325,698 A | 6/1967 | Mooneyhan |
| 3,816,748 A | 6/1974 | Harrison |

(Continued)

FOREIGN PATENT DOCUMENTS

| AU | 768635 B2 | 12/2003 |
| CN | 2415294 Y | 1/2001 |

(Continued)

OTHER PUBLICATIONS

Machine Translation of Description of JP2007-046891—retreived on Mar. 2014.*

(Continued)

*Primary Examiner* — Cheryl J Tyler  
*Assistant Examiner* — Orlando E Aviles Bosques  
(74) *Attorney, Agent, or Firm* — Buchanan Ingersoll & Rooney PC

(57) ABSTRACT

It is an object to provide an electrostatic atomizing apparatus which is simply structured, is easy to assemble, is low in cost, has clogging resistance against foreign matter, can be used for a long time, and is highly reliable, or a home electrical appliance such as a refrigerator, air conditioner, etc. including the electrostatic atomizing apparatus. A discharge electrode formed of foam metal, whereto water that attaches to a surface is supplied by capillary action, a counter electrode provided so as to be opposed to the discharge electrode, and a water supply that is provided directly above the discharge electrode via a predetermined clearance, supplying water to the discharge electrode or the electrode holding part, are included.

15 Claims, 29 Drawing Sheets

(51) Int. Cl.
- *B05B 5/057* (2006.01)
- *B05B 5/16* (2006.01)
- *B05B 5/025* (2006.01)
- *B05B 5/053* (2006.01)
- *F24F 11/00* (2006.01)
- *A61L 9/14* (2006.01)

(52) U.S. Cl.
CPC ............. *B05B 5/0533* (2013.01); *B05B 5/0535* (2013.01); *F24F 11/0086* (2013.01); *A61L 9/14* (2013.01); *F24F 2011/0047* (2013.01); *F24F 2011/0094* (2013.01)
USPC ........... 62/303; 62/3.2; 62/3.6; 62/78; 62/373

(56) References Cited

U.S. PATENT DOCUMENTS

| | | |
|---|---|---|
| 5,577,958 A | 11/1996 | Kumekawa et al. |
| 5,981,319 A | 11/1999 | Lothian et al. |
| 6,139,995 A | 10/2000 | Burm et al. |
| 6,449,139 B1 | 9/2002 | Farahmandi et al. |
| 6,552,786 B1 | 4/2003 | Frech et al. |
| 7,503,512 B2 | 3/2009 | Nakada et al. |
| 7,959,717 B2 | 6/2011 | Yano et al. |
| 2008/0292450 A1 | 11/2008 | Yano et al. |
| 2009/0179093 A1 | 7/2009 | Wada et al. |
| 2010/0000240 A1 | 1/2010 | Nakada et al. |
| 2010/0024462 A1 | 2/2010 | Kamisako et al. |
| 2010/0025505 A1 | 2/2010 | Suda et al. |
| 2010/0044476 A1* | 2/2010 | Yano et al. ................ 239/699 |
| 2010/0071402 A1 | 3/2010 | Mihara et al. |
| 2010/0077770 A1 | 4/2010 | Kamisako et al. |
| 2010/0077791 A1 | 4/2010 | Kamisako et al. |
| 2010/0133367 A1* | 6/2010 | Yano et al. ................ 239/700 |
| 2010/0147003 A1 | 6/2010 | Ueda et al. |

FOREIGN PATENT DOCUMENTS

| | | |
|---|---|---|
| CN | 2821457 Y | 9/2006 |
| CN | 101235977 A | 8/2008 |
| CN | 101311637 A | 11/2008 |
| EP | 1 944 092 A1 | 7/2008 |
| EP | 2 025 411 A1 | 2/2009 |
| EP | 2 144 022 A1 | 1/2010 |
| GB | 2459595 A | 11/2009 |
| GB | 2460357 A | 12/2009 |
| GB | 2460973 A | 12/2009 |
| JP | S62-94785 A | 5/1987 |
| JP | 2-96579 U | 8/1990 |
| JP | 3-89376 U | 9/1991 |
| JP | 03-089376 U | 9/1991 |
| JP | H0389376 U | 9/1991 |
| JP | H04-8081 U | 1/1992 |
| JP | 04-116367 A | 4/1992 |
| JP | 05-133670 A | 5/1993 |
| JP | 6-257933 A | 9/1994 |
| JP | 7-41376 U | 7/1995 |
| JP | 07-041376 U | 7/1995 |
| JP | 08-042960 A | 2/1996 |
| JP | 08-145545 A | 6/1996 |
| JP | 09-105575 | 4/1997 |
| JP | 11-023041 A | 1/1999 |
| JP | 2888243 B2 | 5/1999 |
| JP | 1 083 390 A2 | 3/2001 |
| JP | 2001-074299 A | 3/2001 |
| JP | 2001-272097 A | 10/2001 |
| JP | 2002-203657 A | 7/2002 |
| JP | 2002-267325 A | 9/2002 |
| JP | 2003-121050 A | 4/2003 |
| JP | 2003-121058 A | 4/2003 |
| JP | 2003-172577 A | 6/2003 |
| JP | 2003-214757 A | 7/2003 |
| JP | 2003-214758 A | 7/2003 |
| JP | 2003-287331 A | 10/2003 |
| JP | 2003-287355 A | 10/2003 |
| JP | 2004-060998 A | 2/2004 |
| JP | 2004-061063 A | 2/2004 |
| JP | 2004-293939 A | 10/2004 |
| JP | 2004-353959 A | 12/2004 |
| JP | 2005-028323 A | 2/2005 |
| JP | 2005-226947 A | 8/2005 |
| JP | 2005-337694 A | 8/2005 |
| JP | 2005-254208 A | 9/2005 |
| JP | 2005-282873 A | 10/2005 |
| JP | 2006-007195 A | 1/2006 |
| JP | 2006-035171 A | 2/2006 |
| JP | 2006-038444 A | 2/2006 |
| JP | 2006-057999 A | 3/2006 |
| JP | 2006-61072 A | 3/2006 |
| JP | 2006-068711 A | 3/2006 |
| JP | 2006-090632 A | 4/2006 |
| JP | 2006-105404 A | 4/2006 |
| JP | 2006-118825 A | 5/2006 |
| JP | 2006-145080 A | 6/2006 |
| JP | 2006-150162 A | 6/2006 |
| JP | 2006-162195 A | 6/2006 |
| JP | 2006-189209 A | 7/2006 |
| JP | 2006-337012 A | 12/2006 |
| JP | 2007-021376 A | 2/2007 |
| JP | 2007-029812 A | 2/2007 |
| JP | 2007-040681 A | 2/2007 |
| JP | 2007-046891 A | 2/2007 |
| JP | 2007-046892 A | 2/2007 |
| JP | 2007-054808 A | 3/2007 |
| JP | 2007-101023 A | 4/2007 |
| JP | 2007-101033 A | 4/2007 |
| JP | 2007-101034 A | 4/2007 |
| JP | 2007-117971 A | 5/2007 |
| JP | 2007-181835 A | 7/2007 |
| JP | 2007-240055 A | 9/2007 |
| JP | 2007-240056 A | 9/2007 |
| JP | 2007-263551 A | 10/2007 |
| JP | 2007-275800 A | 10/2007 |
| JP | 2007-292434 A | 11/2007 |
| JP | 2007-327741 A | 12/2007 |
| JP | 2008-18404 A | 1/2008 |
| JP | 2008-032363 A | 2/2008 |
| JP | 2008-039315 A | 2/2008 |
| JP | 2008-039354 A | 2/2008 |
| JP | 2008-070001 A | 3/2008 |
| JP | 2008-089203 | 4/2008 |
| JP | 2008-089203 A | 4/2008 |
| JP | 2008-089282 A | 4/2008 |
| JP | 2008-133980 A | 6/2008 |
| JP | 2008-149243 A | 7/2008 |
| JP | 2008-155144 A | 7/2008 |
| JP | 2008-185289 A | 8/2008 |
| JP | 2008-190813 A | 8/2008 |
| JP | 2008-190819 A | 8/2008 |
| JP | 2008-212696 A | 9/2008 |
| JP | 2008-238060 A | 10/2008 |
| JP | 2008-292134 A | 12/2008 |
| JP | 2008-292135 A | 12/2008 |
| JP | 2008-292136 A | 12/2008 |
| JP | 2008292130 A | 12/2008 |
| JP | 2009-002587 A | 1/2009 |
| JP | 2009-2588 A | 1/2009 |
| JP | 2009-002590 A | 1/2009 |
| JP | 2009-007965 A | 1/2009 |
| JP | 2009-030934 A | 2/2009 |
| JP | 2009-036411 A | 2/2009 |
| SG | 149781 | 11/2010 |
| TW | 200800408 A | 1/2008 |
| WO | WO 2007/142022 A1 | 12/2007 |
| WO | 2008/065737 A1 | 6/2008 |
| WO | 2008/072759 A1 | 6/2008 |
| WO | 2008/139704 A1 | 11/2008 |
| WO | WO 2009/044939 A1 | 4/2009 |

OTHER PUBLICATIONS

Submission of Information dated Jan. 7, 2014, issued in corresponding Japanese Patent Application No. 2013-133786 and a Partial English translation thereof.*

(56) References Cited

OTHER PUBLICATIONS

Submission of Information dated May 24, 2013 issued by the Japanese Patent Office in corresponding Japanese Patent Application No. 2012-285438, and a partial translation thereof.
Inquiry dated Jun. 11, 2013 issued by the Japanese Patent Office in corresponding Japanese Patent Application No. 2011-91231, and a partial translation thereof.
Submission of Information issued on Oct. 11, 2012 by the Japanese Patent Office in corresponding Japanese Application No. 2011-91231, and an English translation thereof.
Office Action issued on Oct. 23, 2012 by the Japanese Patent Office in corresponding Japanese Application No. 2011-91231, and an English translation thereof.
Office Action (Notification of Reasons for Rejection) dated Dec. 20, 2011, issued by the Japanese Patent Office in corresponding Japanese Patent Application No. 2011-091230 and English Translation of Office Action. (6 pages).
Office Action dated Feb. 12, 2013 issued by the Japanese Patent Office in corresponding Japanese Patent Application No. 2011-091229, and a partial English translation thereof.
Notification dated Mar. 21, 2013 issued by the Taiwanese Patent Office in corresponding Taiwanese Patent Application No. 99105600, and an English translation thereof.
Search Report dated Jul. 2, 2013 issued in corresponding Singapore Patent Application No. 201107715-3.
Submission of Information dated Jul. 24, 2013 issued in corresponding Japanese Patent Application No. 2012-285438, and a partial English translation thereof.
Office Action dated Aug. 6, 2013 issued in corresponding Japanese Patent Application No. 2012-171090, and a partial English translation thereof.
European Search Report dated Aug. 27, 2013 issued in corresponding European Patent Application No. 13 15 3069.3.
Office Action dated Sep. 10, 2013 issued in corresponding Japanese Patent Application No. 2012-285438, and a partial English trnaslation thereof.
The extended European Search Report dated Jul. 11, 2012, issued in corresponding European Patent Application No. 11007840.9. (8 pages).
The extended European Search Report dated Jul. 11, 2012, issued in corresponding European Patent Application No. 10755790.2. (4 pages).
Office Action from Japanese Patent Office issued in corresponding Japanese Patent Application No. 2011-091230 dated Aug. 9, 2011, with an English translation thereof.
Japanese Office Action (Reasons) dated Aug. 7, 2012, issued in corresponding Japanese Patent Application No. 2011-091231, and partial English language translation of Office Action. (5 pages).
Office Action dated Aug. 21, 2012, issued in corresponding Japanese Patent Application No. 2011-124181, and an English Translation thereof. (7 pages).
Office Action from Japanese Patent Office issued in corresponding Japanese Patent Application No. 2011-091226 dated Aug. 30, 2011, with a partial English translation thereof.
Office Action dated Sep. 25, 2012, issued in corresponding Tawainese Patent Application No. 99105600, and an English Translation thereof. (4 pages).
Office Action (Notification of the First Office Action) issued on Sep. 4, 2013, by the Chinese Patent Office in corresponding Chinese Patent Application No. 21080014877.6, and a partial English Translation of the Office Action. (17 pages).
Office Action issued on Sep. 24, 2013, by the Japanese Patent Office in corresponding Japanese Patent Application No. 2012-171091, and a partial English Translation of the Office Action. (4 pages).
The partial European Search Report issued on Oct. 1, 2013, by the European Patent Office in corresponding European Patent Application No. 13175635.5-1760. (6 pages).
Office Action issued on Oct. 8, 2013, by the Japanese Patent Office in corresponding Japanese Patent Application No. 2013-133786, and a partial English Translation of the Office Action. (7 pages).

Office Action (Notification of the First Office Action) issued on Sep. 4, 2013, by the Chinese Patent Office in corresponding Chinese Patent Application No. 201080014877.6, and a partial English Translation of the Office Action. (17 pages).
Inquiry issued on Sep. 24, 2013, by the Japanese Patent Office in corresponding Japanese Patent Application No. 2012-171091, and a partial English Translation of the Office Action. (4 pages).
An English translation of the Singapore Written Opinion and Singapore Search Report dated Apr. 18, 2012 issued in corresponding Singapore Patent Application No. 201106635-4. (18 pages).
Submission of Information issued on Oct. 9, 2012 by the Japanese Patent Office in corresponding Japanese Patent Application No. 2011-124181, and an English translation thereof.
International Search Report (PCT/ISA/210) issued on Jun. 1, 2010, by Japanese Patent Office as the International Searching Authority for International Application No. PCT/JP2010/052444.
Office Action (Reasons) issued on Mar. 4, 2014, by the Japanese Patent Office in corresponding Japanese Patent Application No. 2011-91231 and partial English translation of the Office Action. (5 pages).
Office Action (Decision of Rejection) issued on Mar. 4, 2014, by the Japanese Patent Office in corresponding Japanese Patent Application No. 2013-133786 and partial English translation of the Office Action. (2 pages).
Office Action issued on Apr. 1, 2014, by the Japanese Patent Office in corresponding Japanese Patent Application No. 2012-171090, and an English Translation of the Office Action. (7 pages).
Chinese Office Action dated Apr. 8, 2014 (Notification of the Second Office Action) issued in corresponding Chinese Patent Application No. 201080014877.6 and an English translation thereof (18 pgs.).
Office Action issued on May 27, 2014, by the Japanese Patent Office in corresponding Japanese Patent Application No. 2013-003064 and an English translation of the Office Action. (3 pages).
Office Action issued on Jun. 3, 2014, by the Japanese Patent Office in corresponding Japanese Patent Application No. 2012-171091 and an English translation of the Office Action. (4 pages).
Notice by Submission of Information dated Apr. 9, 2013 issued in corresponding Japanese Patent Application No. 2012-171091, and a partial translation thereof.
Notice by Submission of Information dated Apr. 16, 2013 issued in corresponding Japanese Patent Application No. 2012-171091, and a partial translation thereof.
Office Action dated Apr. 23, 2013 issued in corresponding Japanese Patent Application No. 2012-171091, and a partial translation thereof.
Office Action dated Apr. 23, 2013 issued in corresponding Japanese Patent Application No. 2012-285438, and a partial translation thereof.
Office Action dated May 8, 2013 issued in corresponding European Patent Application No. 10 755 790.2.
Office Action dated May 8, 2013 issued in corresponding European Patent Application No. 11 007 840.9.
European Search Report dated May 10, 2013 issued in corresponding European Patent Application No. 13 153 064.4.
Office Action dated Apr. 3, 2013 issued in corresponding U.S. Appl. No. 13/260,402.
Office Action issued on Jul. 15, 2014, by the Japanese Patent Office in corresponding Japanese Patent Application No. 2012-171090, and an English Translation of the Office Action. (8 pages).
Reconsideration Report issued on Jul. 15, 2014, by the Japanese Patent Office in corresponding Japanese Patent Application No. 2013-133786, and an English Translation of the Office Action. (4 pages).
Office Action issued on Jul. 22, 2014, by the Chinese Patent Office in corresponding Chinese Patent Application No. 201210553574.2, and an English Translation of the Office Action. (22 pages).
Office Action issued on Aug. 5, 2014, by the Japanese Patent Office in corresponding Japanese Patent Application No. 2014-080773, and an English Translation of the Office Action. (8 pages).
Office Action issued by the U.S. Patent and Trademark Office in the U.S. Appl. No. 13/260,402, mailed Sep. 18, 2014, U.S. Patent and Trademark Office, Alexandria, VA. (31 pages).

(56) References Cited

OTHER PUBLICATIONS

Office Action issued on Sep. 4, 2012 in the Japanese Patent Office in corresponding JP 2011-091228, and a partial translation thereof.
Office Action issued on Sep. 18, 2012 in the Japanese Patent Office in corresponding JP 2012-171091, and a partial translation thereof.
Final Office Action dated Jan. 8, 2013, issued by the Japanese Patent Office in corresponding Japanese Patent Application No. 2011-091231 and partial English translation thereof. (5 pages).
Submission of Information dated Dec. 17, 2012, issued by the Japanese Patent Office in corresponding Japanese Patent Application No. 2011-091231 and an English translation thereof. (9 pages).
Japanese Office Action (Decision of Rejection) dated Feb. 12, 2014, issued in corresponding Japanese Patent Application No. 2012-285438 and an English Translation thereof. (3 pgs).
Japanese Office Action dated Dec. 10, 2013, issued in corresponding Japanese Patent Application No. 2013-003064 and a partial English Translation thereof. (9 pgs).
Submission of Information dated Jan. 7, 2014, issued in corresponding Japanese Patent Application No. 2013-133786 and a partial English Translation thereof. (2 pgs).
Singapore Search Report and Written Opinion dated Jan. 2, 2014, issued by Intellectual Property Office of Singapore in corresponding Singapore Patent Application No. 201301679-5. (16 pgs).
Extended European Search Report dated Jan. 28, 2014, issued by the European Patent Office in corresponding European Patent Application 13175635.5 (12 pgs).
European Communication pursuant to Article 94(3) EPC dated Jan. 24, 2014, issued by the European Patent Office in corresponding European Patent Application 13153064.4 (4 pgs).

\* cited by examiner

Fig. 25
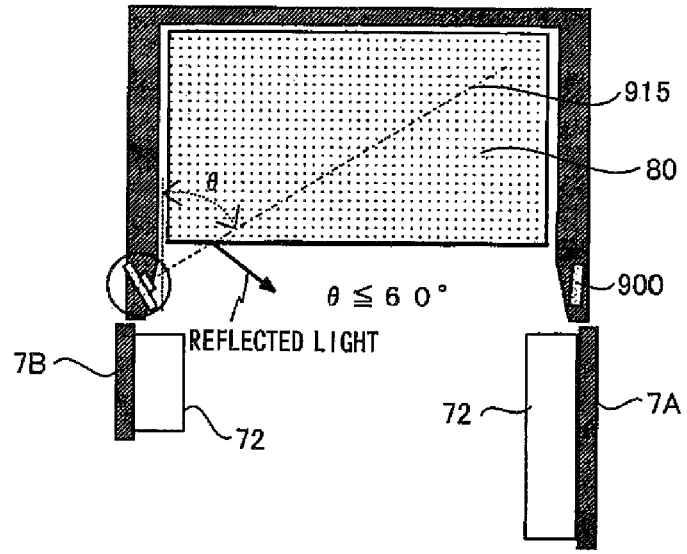
(a)
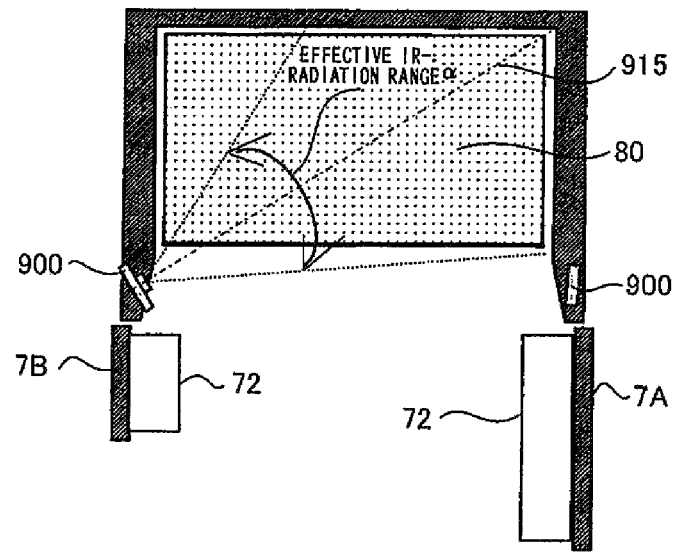
(b)

ELECTROSTATIC ATOMIZING APPARATUS, APPLIANCE, AIR CONDITIONER, AND REFRIGERATOR

TECHNICAL FIELD

The present invention relates to an electrostatic atomizing apparatus that generates nano-size mist, an (home electrical) appliance such as a refrigerator, a display case, an industrial refrigerator, a storage, etc., and an air conditioner (including an air purifier and a humidifier and the like), etc., and an air conditioner inside of an appliance.

BACKGROUND ART

It is described an electrostatic atomizing apparatus equipped with a conveying part for conveying water from a water reservoir part, a counter electrode arranged so as to be opposed in a conveying direction of the conveying part, and a water application electrode for applying a voltage to water in a route leading from the water reservoir part to a distal end of the counter electrode side of the conveying part, in an upper portion of the water reservoir part, wherein the conveying part is constituted by a porous ceramic formed of solid acid as a material (for example, see Patent literature 1).

It is described an electrostatic atomizing apparatus equipped with a water conveying part for conveying water by capillary action, a water supplying part for supplying water to the water conveying part, and an applying electrode for applying a voltage to the water conveyed by the water conveying part, wherein the water supplying part is a heat exchange part consisting of an endothermic plate having an endothermic surface and generating dew condensation water by cooling air on the endothermic surface, a Peltier element, and a heat sink, and the heat exchange part is located below the water conveying part (for example, see Patent literature 2).

In recent years, it has been proposed a refrigerator equipped with an atomizing apparatus including a cooling panel that condenses moisture in air in the refrigerator and that is provided in a cooling air duct, a conveying part that conveys the water condensed by the cooling panel to a water reservoir part, a capillary water drawing member that conveys the water in the water reservoir part to a voltage application part between an application electrode and a counter electrode, wherein the atomizing apparatus can generate mist or ozone capable of deodorizing inside a storage compartment by applying a voltage (for example, see Patent literature 3).

Further, it is proposed a refrigerator equipped with a water storage tank installed below a cover of the refrigerator wherein the cover is provided to make the humidity inside of a vegetable case high, and a mist generator (ultrasonic transducer) in a lower part (bottom surface) of the water storage tank (for example, see Patent literature 4).

Furthermore, it is described a refrigerator equipped with an multi-color illuminating means in a display unit provided on a front door of the refrigerator, which switches light emission colors or a light emission condition by operation of a control unit, and displays "bacterial eradication mode" on the display unit when a bacterial eradication button is pressed by a user (for example, see Patent literature 5).

Further, it is described a refrigerator equipped with an ultrasonic humidifier in a vegetable compartment that utilizes defrosted water for feeding water (for example, see Patent literature 6).

Furthermore, it is described a refrigerator that is equipped with an atomizing apparatus for supplying fine mist to a storage compartment, and a water storage part for storing liquid supplied to the atomizing apparatus, and that includes, in a pathway (canalicular path) connecting the atomizing apparatus and the water storage part, a removing member for removing a content of the liquid (for example, see Patent literature 7).

CITATION LIST

Patent Literature

Patent literature 1: JP 2006-035171 A
Patent literature 2: JP 2007-181835 A
Patent literature 3: JP 2007-101034 A
Patent literature 4: JP 2006-162195 A
Patent literature 5: JP 2003-172577 A
Patent literature 6: JP 6-257933 A
Patent literature 7: JP 2008-089203 A

SUMMARY OF INVENTION

Technical Problem

In the atomizing apparatus described in Patent literature 1, a ceramic is used for the conveying part. However, generally, a ceramic has a porosity (voidage) of approximately 10 to 50% and a pore diameter (average of pore diameters or diameters of void parts) of approximately 0.1 to 3 μm, and has electrical resistance of approximately $(0.2 \text{ to } 2) \times 10^{12}$ Ω·m, which is large. As just described, ceramic materials have extremely low clogging resistance against foreign matter since the pore diameters are extremely small, and there is a problem in reliability when the ceramic materials are used for a long period. Further, since the voidage is low as well, the capillary force is small and absorptive power or a retaining amount of water is small, hence there is a possibility that it takes a long time before electrostatic atomization starts, or that atomization is interrupted. Additionally, since the impedance is extremely high, the ceramic materials do not readily conduct electricity, and it is less likely that a high voltage is applied to the ceramic materials, hence large electrical power is necessary.

Further, the conveying part is inserted in the water reservoir part so as to be directed in the vertical direction, the counter electrode is arranged so as to be opposed to an end of the upper part of the conveying part, and the water reservoir part is integrally formed with the conveying part and the counter electrode, etc. It is necessary to remove the water reservoir part from a main body of an appliance such as an air purifier due to necessity of supplying water to the water reservoir part; however, when a user removes the water reservoir part from the main body of the appliance, since the water reservoir part is integrally formed with the conveying part and the counter electrode, etc., it is necessary to remove the conveying part and an electrode part such as the counter electrode at the same time, which may cause the user to touch the electrode part and get an electrical shock.

In the atomizing apparatus described in Patent literature 2, the heat exchange part is provided below the water conveying part, and the heat exchange part is formed by arranging the Peltier element below the endothermic plate having the endothermic surface, and then the heat sink below the Peltier element; therefore, when the amount of dew condensation water generated on the endothermic surface is large, the dew condensation water may overflow and spill over the Peltier element provided below the endothermic surface, which may break down the Peltier element weak in water.

Since the refrigerator equipped with the atomizing apparatus described in Patent literature 3 includes the conveying part that conveys the water condensed on the cooling panel to the water reservoir part, there are problems that the path from the cooling panel to the water reservoir part is long, the conveying part has a complicated structure, the number of components is large, the cost is high, the assembling efficiency is low, and further, the conveying part is clogged with dust or the like entering the conveying part and the condensed water is not supplied to the water reservoir part. Furthermore, the capillary water drawing member and the application electrode are separate members, which makes the structure complicated, the assembling efficiency low, and the cost high. Additionally, a water level detection means is provided in the water reservoir part, and there are problems that the number of components is large, the cost is high and control is complex.

In the refrigerator equipped with the atomizing apparatus in the vegetable case described in Patent literature 4, since a vegetable container and the cover are directly used as a cooling panel of the mist generator, collection of dew condensation water depends on the shapes and the sizes of the vegetable container and the cover; therefore, there are many restrictions in the shapes of the vegetable container and the cover, the installation space of which is limited and the drastic shape modification or the like of which is impossible also for the necessity of enlargement of the inner volume, and it is not easy to stably secure water necessary for mist spray. Further, since the vegetable container and the cover are directly used for the cooling panel, it is necessary to set the humidity inside of the vegetable case high so as to generate dew condensation water, development to the other storage compartments wherein the humidity cannot be high, and the like is difficult. Furthermore, since the mist generator (ultrasonic transducer) is installed on the bottom surface of the water storage tank, the structure including a seal structure as a countermeasure against water leakage between the water storage tank and the mist generator, etc. is complicated, the assembling efficiency is low, and the cost is increased. Additionally, since the ultrasonic transducer is used for the mist generator, mist cannot be miniaturized, and it is difficult to spray the mist uniformly in the refrigerator.

Further, in Patent literature 3 and Patent literature 4, a user finds it difficult to recognize and has no way to ascertain whether the atomizing apparatus is operating. What is more, the user cannot recognize whether the electrostatic atomizing apparatus is really operating or when the electrostatic atomizing apparatus has started to operate, and thus the user feels suspicious.

Further, in the refrigerator described in Patent literature 5, "bacterial eradication mode" is displayed when a user presses the bacterial eradication button; however, when the refrigerator enters the bacterial eradication mode in a case of the user not pressing the bacterial eradication button, the user cannot know whether the bacterial eradication is performed if the user is not in front of the refrigerator, and thus the user feels uneasy.

Furthermore, the refrigerator described in Patent literature 6 is equipped with the ultrasonic humidifier in the vegetable compartment that utilizes defrosted water for feeding water; however, a concrete structure of how the defrosted water is utilized for the feeding water is not described at all, hence it is difficult to obtain the defrosted water when needed. Further, it is necessary to use an atomization filter having pore diameters of 0.2 to 0.3 mm and a thickness of 80 to 100 μm to generate mist, handling and installation structure of which is difficult, which makes the structure complicated. Furthermore, since the ultrasonic transducer is used in the mist generator, mist cannot be miniaturized, and it is difficult to spray the mist uniformly in the refrigerator.

Further, in the refrigerator described in Patent literature 7, the pathway (canalicular path) is provided inside of a heat insulating material for connecting the atomizing apparatus and the water storage part, and further, it is necessary to install a water conveyance means that controls the amount of conveyed water, which makes the structure complicated and the cost high. Additionally, it is necessary to form linear micropores in a horn from the bottom surface part to the end for supplying water to the atomizing part at the end, which makes the processing difficult and the cost high.

It is an object of the present invention to provide a simply structured, easy-to-assemble and low-cost electrostatic atomizing apparatus (mist spraying apparatus), or an (home electrical) appliance, such as a refrigerator, an air conditioner, etc., equipped with the electrostatic atomizing apparatus.

Further, it is an object of the present invention to provide an electrostatic atomizing apparatus (mist spraying apparatus) which has high clogging resistance against foreign matter, can be used for a long time, is highly reliable, has large absorptive power and retaining amount of water, starts electrostatic atomization within a short time, generates atomization without interruption, has low impedance, and consumes low power, or to provide an (home electrical) appliance, such as a refrigerator, an air conditioner, etc., equipped with the electrostatic atomizing apparatus.

Further, it is an object of the present invention to provide a highly reliable electrostatic atomizing apparatus (mist spraying apparatus) wherein dew condensation water does not spill over a Peltier element, and breakdown, etc. of the Peltier element does not occur even when the Peltier element is used between a heat absorbing plate and a heat sink in a heat exchange part, or to provide an (home electrical) appliance, such as a refrigerator, an air conditioner, etc., equipped with the electrostatic atomizing apparatus.

Furthermore, it is an object of the present invention to provide an (home electrical) appliance, such as a refrigerator, an air conditioner, etc., that is capable of miniaturizing and spraying uniformly in a storage compartment atomized water particles.

Further, it is an object of the present invention to provide a simply structured, low-cost and inexpensive electrostatic atomizing apparatus wherein a conveying part, a pathway (canalicular path), processing of micropores to electrodes, etc. is unnecessary, or an (home electrical) appliance, such as a refrigerator, an air conditioner, etc., equipped with the electrostatic atomizing apparatus.

Furthermore, it is an object of the present invention to provide an electrostatic atomizing apparatus that is equipped with a means whereby whether the electrostatic atomizing apparatus is operating, a history of when the electrostatic atomizing apparatus operated, etc. can be visually confirmed.

Further, it is an object to provide an electrostatic atomizing apparatus that is applicable to a storage compartment of any temperature zones.

Furthermore, it is an object of the present invention to provide an electrostatic atomizing apparatus which is operable without installing a water reservoir part or a water level detection means, composed of a small number of components, and simply structured, or to provide an (home electrical) appliance, such as a refrigerator, an air conditioner, etc., equipped with the electrostatic atomizing apparatus.

Further, it is an object of the present invention to provide an (home electrical) appliance, such as a refrigerator, an air conditioner, etc., equipped with a high-performance and highly reliable electrostatic atomizing apparatus that can prevent running out of water.

Furthermore, it is an object of the present invention to provide a low-cost and highly reliable electrostatic atomizing apparatus that is capable of humidification and bacterial eradication in a storage compartment, wherein clogging, etc. does not occur, or an (home electrical) appliance, such as a refrigerator, an air conditioner, etc., equipped with the electrostatic atomizing apparatus.

Additionally, it is an object of the present invention to provide especially an air conditioner which can attain the above-mentioned objects among these (home electrical) appliances.

Solution to Problem

The electrostatic atomizing apparatus according to the present invention includes a discharge electrode composed of a main body part having an approximately rectangular parallelepiped shape or an approximately columnar shape elongated in an axial direction, and a protrusion part having an approximately rectangular parallelepiped shape, an approximately columnar shape, an approximately pyramid shape, or an approximately conical shape, the protrusion part protruding at an approximately right angle to the axial direction of the main body part, being shorter than a length in the axial direction of the main body part, and being formed integrally with the main body part, whereto water that attaches to a surface of the main body is supplied by a capillary action, an electrode holding part that holds the discharge electrode, a counter electrode that is provided so as to be opposed to the protrusion part, and a water supply means that is provided directly above the main body part via a predetermined clearance, and that supplies water to the discharge electrode or the electrode holding part, wherein the length in the axial direction of the main body part is within a range of equal to or larger than 4 times and equal to or smaller than 20 times as long as the protrusion part.

Advantageous Effects of Invention

According to the present invention, processing efficiency is better, water can be stably supplied to the protrusion part for a long period of time, and mist can be stably sprayed.

BRIEF DESCRIPTION OF DRAWINGS

FIG. 2 is opened, describing the present embodiment.

FIG. 25 is a top view of a refrigerating compartment 2 of an alternative refrigerator 1 describing the embodiment of the present invention.

DESCRIPTION OF EMBODIMENTS

Embodiment 1

Refrigerator

Figure 1:
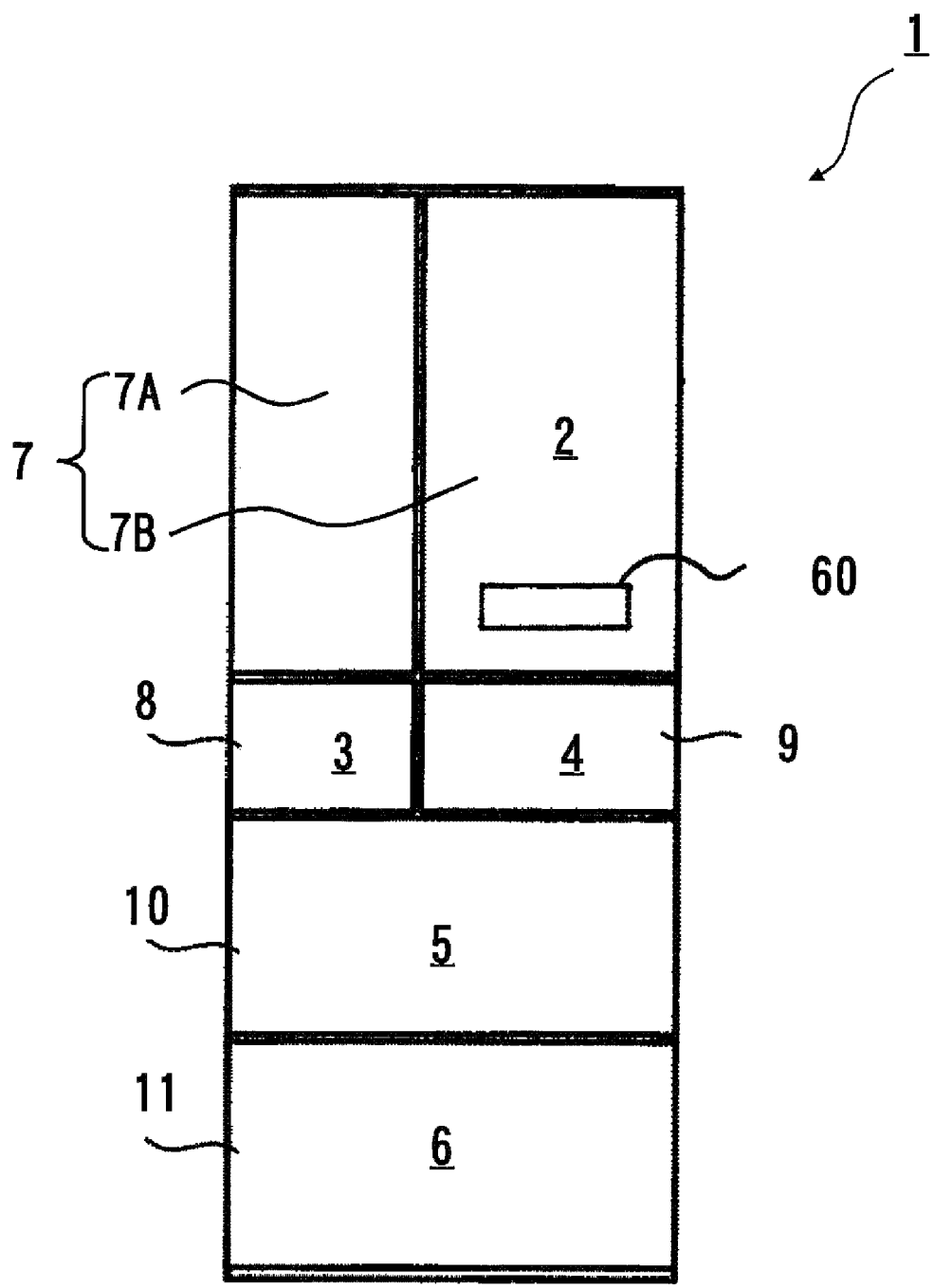
FIG. 1 is a front view of a refrigerator 1 describing an embodiment of the present invention.
Figure 2:
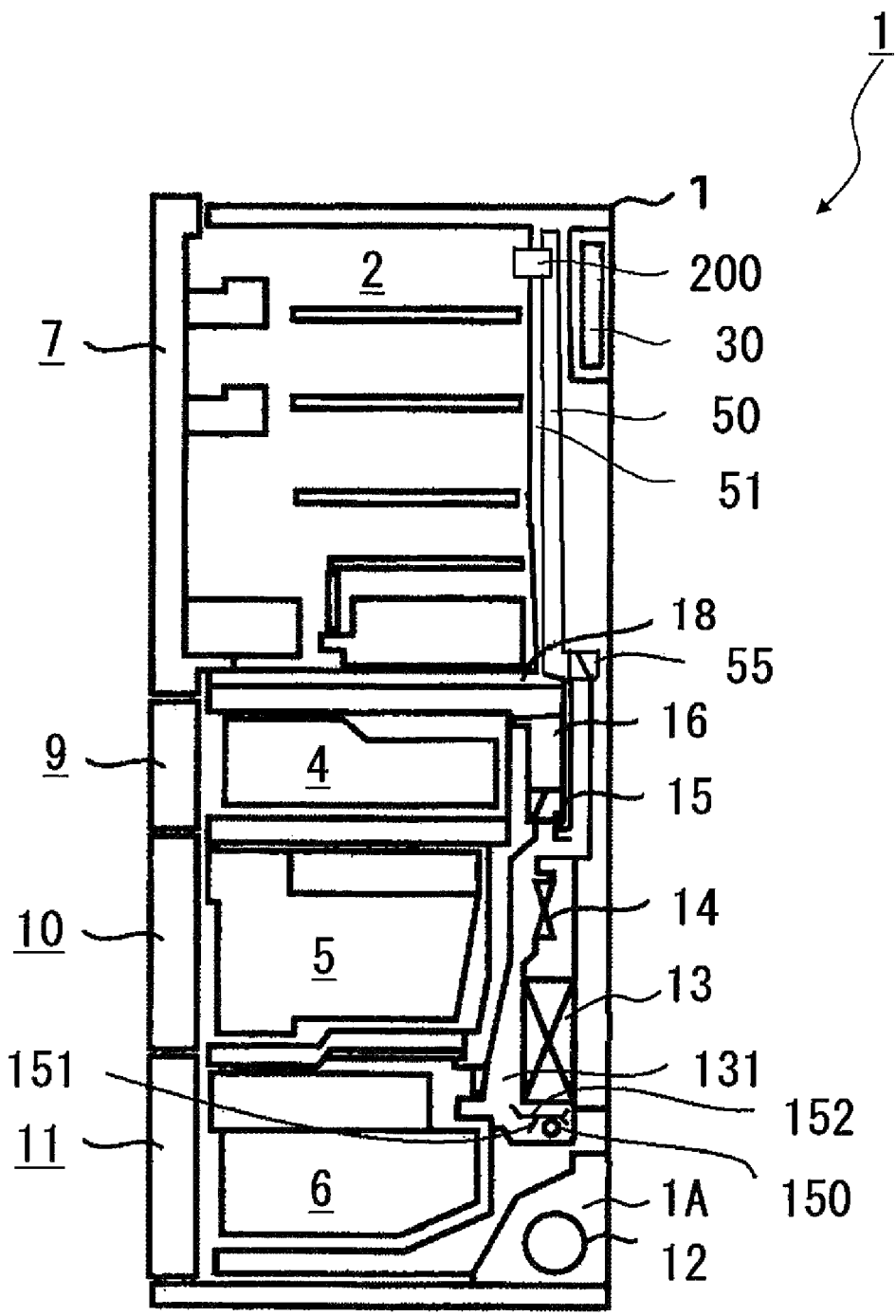
FIG. 2 is a sectional side view of the refrigerator 1 describing the embodiment of the present invention.

FIG. 1 is a front view of the refrigerator 1 describing the first embodiment of the present invention, and FIG. 2 is a sectional side view of the refrigerator 1 describing the first embodiment of the present invention. In the diagrams, the refrigerator 1 is provided with a side-by-side (or an openable) refrigerating compartment 2 at the top shelf. A switching compartment 4 and an ice making compartment 3 are arranged in parallel on the right and left sides below the refrigerating compartment 2. A freezing compartment 6 is provided at the bottom shelf in the refrigerator 1, and a vegetable compartment 5 is provided above the freezing compartment 6. The vegetable compartment 5 is located below the switching compartment 4 and the ice making compartment 3 arranged in parallel on the right and left sides, and above the freezing compartment 6.

Of course, the layout of each compartment does not limit the present embodiment. In a so-called mid-freezer type, wherein the switching compartment 4 and the ice making compartment 3 are arranged in parallel on the right and left sides below the refrigerating compartment 2 provided at an upper shelf, and the freezing compartment 6 is provided below the switching compartment 4 and the ice making compartment 3 arranged in parallel on the right and left sides, and further above the vegetable compartment 5 provided at a lower shelf, that is, the freezing compartment 6 is provided between the vegetable compartment 5, and the switching compartment 4 and the ice making compartment 3 arranged in parallel on the right and left sides, compartments at low temperatures (for example, the ice making compartment 3, the switching compartment 4 and the freezing compartment 6) are close to one another; therefore, heat insulating materials between the compartments at low temperatures are unnecessary, heat leak is small, and thus an energy-saving and low-cost refrigerator can be provided.

A side-by-side refrigerating compartment door 7, which can be freely opened and closed, is provided in a front side opening of the refrigerating compartment 2, which is a storage compartment, and the refrigerating compartment door 7 is formed as a side-by-side door with two of a left refrigerating compartment door 7A and a right refrigerating compartment door 7B. Of course, it may not be the side-by-side door, but a rotary door of one door type. To the ice making compartment 3, the switching compartment 4, the vegetable compartment 5 and the freezing compartment 6, which are the other storage compartments, a slide-out ice making compartment door 8 that can freely open and close an opening of the ice making compartment 3, a slide-out switching compartment door 9 that can freely open and close an opening of the switching compartment 4, a slide-out vegetable compartment door 10 that can freely open and close an opening of the vegetable compartment 5, and a slide-out freezing compartment door 11 that can freely open and close an opening of the freezing compartment 6 are provided, respectively. Further, either of the right refrigerating compartment door 7B or the left refrigerating compartment door 7A on the right and left sides of the refrigerating compartment 2, which is a storage compartment, is equipped with control switches (a compartment selection switch 60a, a temperature zone transfer switch 60b, an instant freezing switch 60c, an ice making transfer switch 60d, and a mist spray switch 60e) that perform a temperature setting, etc. inside the storage compartment, and a control panel 60 that performs display of temperature information such as a temperature inside, a set temperature, etc., and operation information of the control switches, display information of a liquid crystal display unit, and temperature information inside of the storage compartment, etc. are controlled by the control device 30 composed of a control board whereto a microcomputer, etc. is mounted, which is installed in an upper rear surface of the main body of the refrigerator (the rear of the refrigerating compartment).

A compressor 12 is located in a machine compartment 1A formed in the bottom rear surface of the refrigerator 1. The refrigerator 1 includes a refrigerating cycle. The compressor 12 is one component constituting the refrigerating cycle, is located in the machine compartment 1A, and has an effect to compress a refrigerant inside of the refrigerating cycle. The refrigerant compressed by the compressor 12 is condensed in a condenser (not shown in the diagrams). The refrigerant being condensed is depressurized in a capillary tube (not show in the diagrams) or an expansion valve (not shown in the diagrams), which is a depression unit. A cooler 13 is one component constituting the refrigerating cycle of the refrigerator and is located in a cooler compartment 131. The refrigerant depressed by the depression unit evaporates in the cooler 13, and by an endothermic effect at the time of evaporation, air surrounding the cooler 13 is cooled. A cool air circulation fan 14 is located in the vicinity of the cooler 13 inside the cooler compartment 131. The cool air circulation fan 14 is for blowing cool air cooled around the cooler 13 to each compartment (the refrigerating compartment 2, the ice making compartment 3, the switching compartment 4, the vegetable compartment 5 and the freezing compartment 6), which is the storage compartment of the refrigerator 1, via cooling air trunks (for example, a switching compartment cooling air trunk 16, a refrigerating compartment cooling air trunk 50, etc.).

A defrosting heater 150 (a glass tube heater for defrosting, such as a carbon heater wherein carbon fibers emitting light with a wavelength of 0.2 μm to 0.4 μm that penetrates a silica glass tube are used in the silica glass tube, for example) as a defrosting means that performs defrosting of the cooler 13 is installed below the cooler 13. A heater roof 151 is provided between the cooler 13 and the defrosting heater 150, and above the defrosting heater 150 so that defrosted water dropping from the cooler 13 does not directly strikes the defrosting heater 150. If a heater of a black medium such as a carbon heater, etc. is used for the defrosting heater 150, frost over the cooler 13 can be efficiently melted by radiation heat transfer; therefore, it is possible to maintain the surface temperature at a low temperature (approximately 70° C. to 80° C.), and even when refrigerant leakage, etc. occurs in a case where a flammable refrigerant (for example, isobutane, which is a hydrocarbon refrigerant, or the like) is used as a refrigerant used in the refrigerating cycle, the risk of ignition can be reduced. Further, since it is possible to melt the frost over the cooler 13 more efficiently by radiation heat transfer in comparison with a nichrome wire heater, the frost formed over the cooler 13 is gradually melted and is less likely to drop in a cluster at once;

therefore, the drop sound at the time the frost drops on the heater roof 151 can be reduced, thus a low noise refrigerator high in defrosting efficiency can be provided.

Here, the defrosting heater 150 can be an inlaid type heater integrally incorporated into the cooler 13. Further, a glass tube type heater and the inlaid type heater can be used together.

A switching compartment damper 15, which is an air volume control means, is for controlling a cool air volume of cool air blown into the switching compartment 4, which is the storage compartment, by the cool air circulation fan 14, controlling the temperature inside the switching compartment 4 to a predetermined temperature, and switching a set temperature of the switching compartment 4. The cool air cooled by the cooler 13 passes through a switching compartment cooling air trunk 16, which is a cooling air trunk, and is blown into the switching compartment 4. Additionally, the switching compartment cooling air trunk 16 is provided downstream of the switching compartment damper 15.

Further, a refrigerating compartment damper 55, which is an air volume control means, is also for controlling a cool air volume of cool air blown into the refrigerating compartment 2, which is the storage compartment, by the cool air circulation fan 14, for controlling the temperature inside the refrigerating compartment 2 to a predetermined temperature, and for changing a set temperature of the refrigerating compartment 2. The cool air cooled by the cooler 13 passes through the refrigerating compartment cooling air trunk 50, which is a cooling air trunk, and is blown into the refrigerating compartment 2.

The storage compartment, for example, the switching compartment 4 is a compartment (storage compartment) wherein the temperature inside of the storage compartment can be selected from plural levels between a freezing temperature zone (equal to or lower than −17° C.) and a vegetable compartment temperature zone (3 to 10° C.), and the temperature inside of the storage compartment is selected and switched with control of the control panel 60 installed in either of the left refrigerating compartment door 7A or the right refrigerating compartment door 7B of the refrigerator 1.

A switching compartment thermistor 19 (see FIG. 3) as the first temperature detecting means to detect an air temperature inside the switching compartment 4 is installed on, for example, a rear wall surface of the switching compartment 4, and a thermopile 22 (see FIG. 3, or an infrared ray sensor) as the second temperature detecting means to directly detect a surface temperature of a stored product put inside of the switching compartment 4, which is the storage compartment, is installed on, for example, a top surface (a center part, a front part, or a back part, etc.) of the switching compartment 4. The switching compartment damper 15 as the air volume control device that can control an air volume and block an air trunk to prevent inflow of cool air is provided in the air trunk that sends cool air from the cooler compartment 131 to the switching compartment 4, and by opening and closing the switching compartment damper 15 according to a detected temperature of the switching compartment thermistor 19, which is the first temperature detecting means, (or a detected temperature of the thermopile 22), a temperature in the switching compartment 4 is controlled by the control device 30 to be in the selected temperature zone, or to be within the set temperature range. Further, a temperature of a food item, which is a stored product inside the switching compartment 4, is directly detected by the thermopile 22, which is the second temperature detecting means.

The electrostatic atomizing apparatus 200, which is a mist spraying apparatus that sprays mist in the storage compartment, is installed on a partition wall 51 (an insulated wall) at a rear side of the refrigerating compartment 2, which is the storage compartment. In the electrostatic atomizing apparatus 200, a cooling plate 210 (described hereinafter) for collecting moisture in air inside the storage compartment as dew condensation water is provided in a manner to penetrate through the partition wall 51 (the insulated wall) at the rear side of the refrigerating compartment 2 from the inside of the refrigerating compartment 2, which is the storage compartment, and to protrude into the refrigerating compartment cooling air trunk 50, which is a cooling air trunk.

Figure 3:
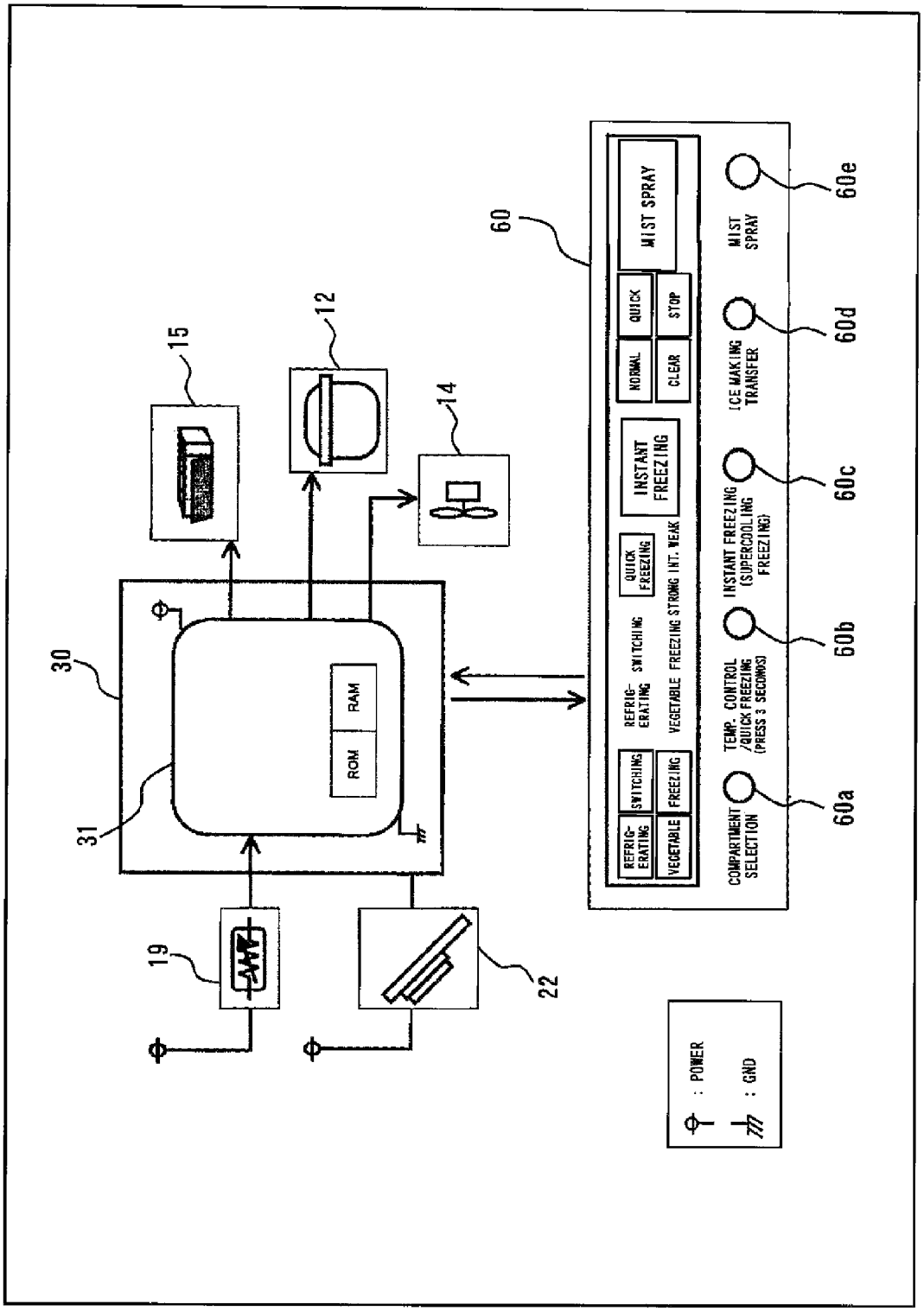
FIG. 3 is a block diagram of a control device 30 of the refrigerator 1 describing the embodiment of the present invention.

FIG. 3 is a block diagram of the control device 30 of the refrigerator 1 describing the first embodiment of the present invention. A microcomputer 31 (micro) is mounted on the control device 30. The control device 30 performs, with previously memorized programs, control over temperatures in each storage compartment of the refrigerator 1, control over the numbers of rotations of the compressor 12 and the cool air circulation fan 14, control of opening and closing the switching compartment damper 15 and the refrigerating compartment damper 55, control over voltage application to the electrostatic atomizing apparatus 200 (a discharge electrode 230 and a counter electrode 240 described hereinafter), etc. The control panel 60 is equipped with the following switches:

(1) the compartment selection switch 60a for selecting the storage compartments such as the refrigerating compartment, the freezing compartment, the switching compartment, etc.;

(2) the temperature zone transfer switch 60b for switching a temperature zone (refrigeration, freezing, chilling, soft freezing, etc.) in the storage compartment such as the switching compartment, etc., and for switching to or from quick cooling, strong, intermediate, weak, etc.;

(3) the instant freezing switch 60c (instant freezing is also called supercooling freezing) whereby the inside of the storage compartment is made to be a frozen storage after a supercooling state;

(4) the ice making transfer switch 60d for selecting, regarding ice making, clear ice, normal, quick, stop, etc.; and (5) the mist spray switch 60e (selecting electrostatic spray) for energizing the electrostatic atomizing apparatus 200 and performing mist spray (electrostatic spray) inside the storage compartments.

Now, a temperature detection sensor that detects temperatures inside a storage compartment (for example, the switching compartment 4) will be explained. In the present embodiment, the switching compartment thermistor 19 as the first temperature detecting means, and the thermopile 22 as the second temperature detecting means are provided as the temperature detection sensors that detect a temperature inside the storage compartment (for example, the switching compartment 4). The detected temperature by the switching compartment thermistor 19, which is the first temperature detecting means that detects a temperature of air inside the storage compartment (for example, the switching compartment 4), is input into the microcomputer 31 that constitutes the control device 30 and is compared with a predetermined value by the microcomputer 31 (for example, a temperature determination means inside the microcomputer 31) whereby a temperature determination is performed, and the temperature is controlled so as to be within a predetermined temperature range. Further, a detected signal by the thermopile 22, which is the second temperature detecting means that directly detects a surface temperature of a food item, etc. inside the storage compartment (for example, the switching compartment 4), is input into the microcomputer 31, is subjected to arithmetic processing by the microcomputer 31 (for example, a computing means inside the microcomputer 31) and is converted into the surface temperature of the food item, etc., and then, predetermined temperature control such as rapid freezing control, supercooling freezing control, etc. is performed. Further, the control device 30 performs control of various types such as temperature control inside each storage compartment (the refrigerating compartment 2, the ice making compartment 3, the switching compartment 4, the vegetable compartment 5, and the freezing compartment 6) and energization control of the electrostatic atomizing apparatus 200 and so on, and displays a set temperature of each storage compartment, a food (surface) temperature, and an operation status of the electrostatic atomizing apparatus 200 installed in each storage compartment, on the control panel 60 (display panel) installed in either of the left refrigerating compartment door 7A or the right refrigerating compartment door 7B.

(Electrostatic Atomizing Apparatus)

Figure 4:
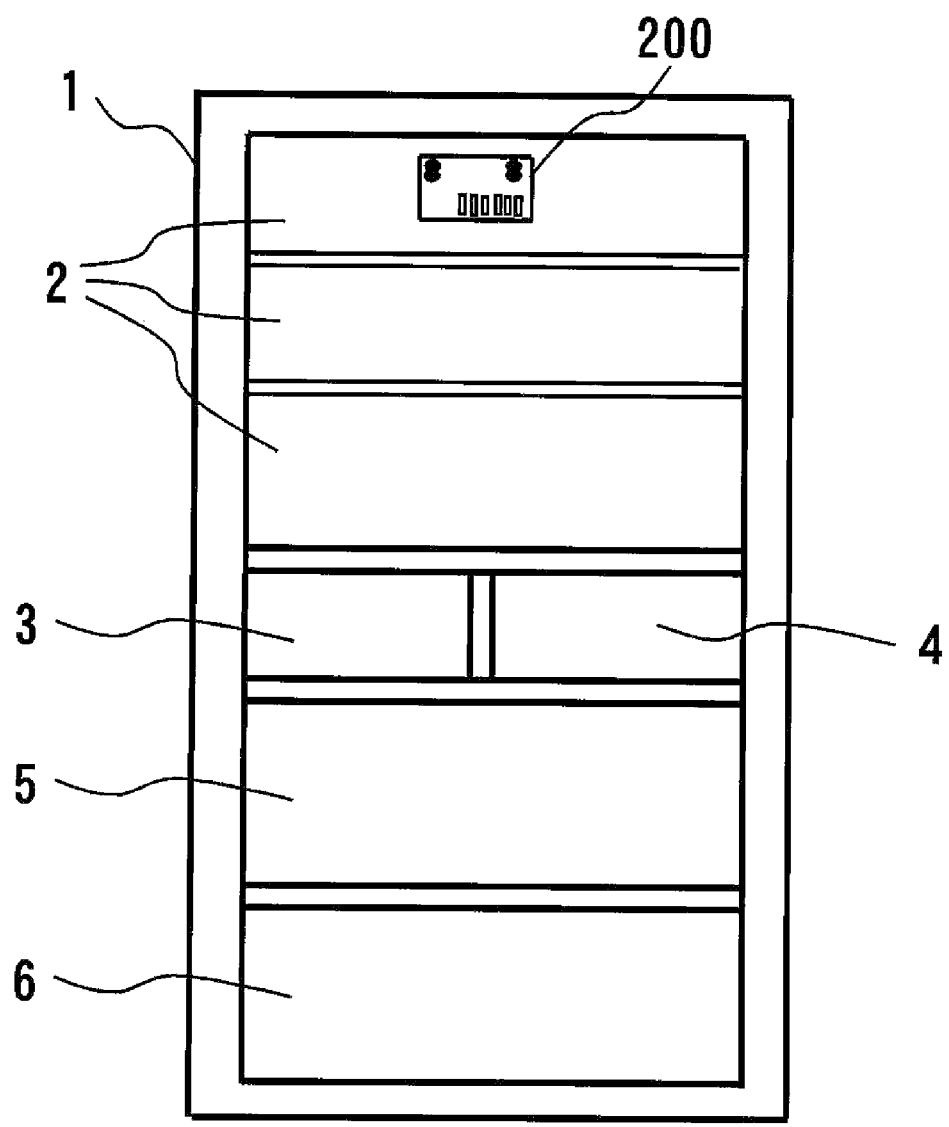
FIG. 4 is a front view of an inside of a storage compartment from an anterior view in a state a door of the refrigerator 1 shown in FIG. 1
Figure 5:
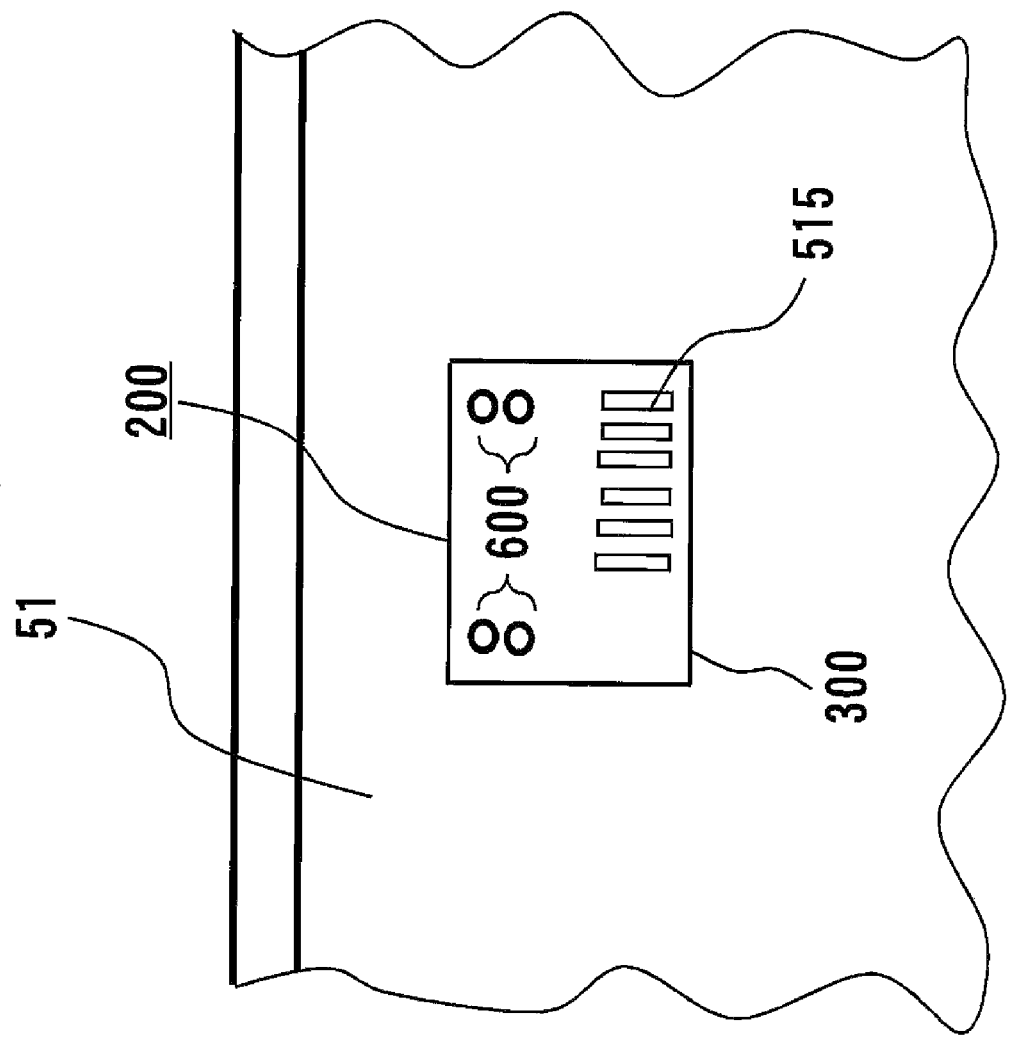
FIG. 5 is a front view of an electrostatic atomizing apparatus 200 in a state where a cover is attached, which is installed in the refrigerator 1 describing the present embodiment.
Figure 6:
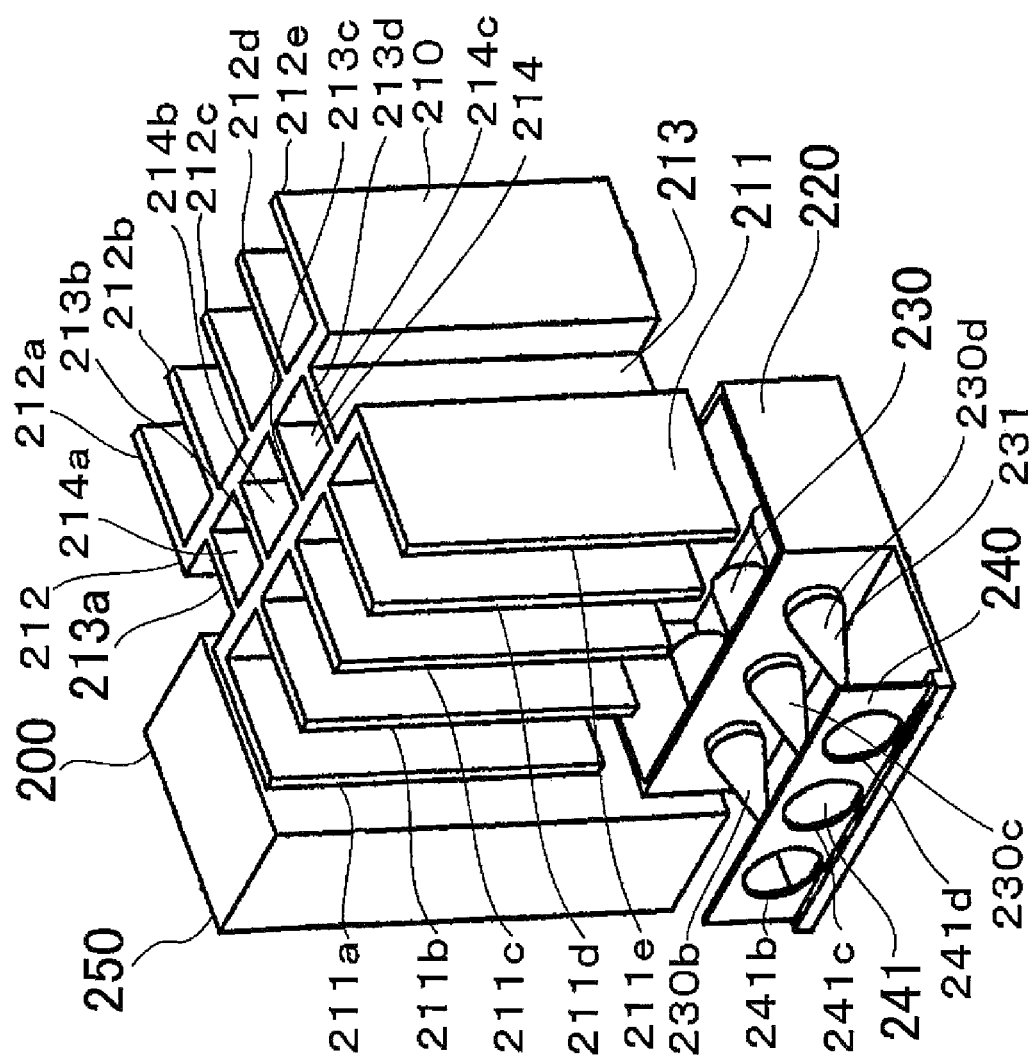
FIG. 6 is a perspective view of inside the cover of the electrostatic atomizing apparatus 200 that is installed in the refrigerator 1 describing the present embodiment.
Figure 7:
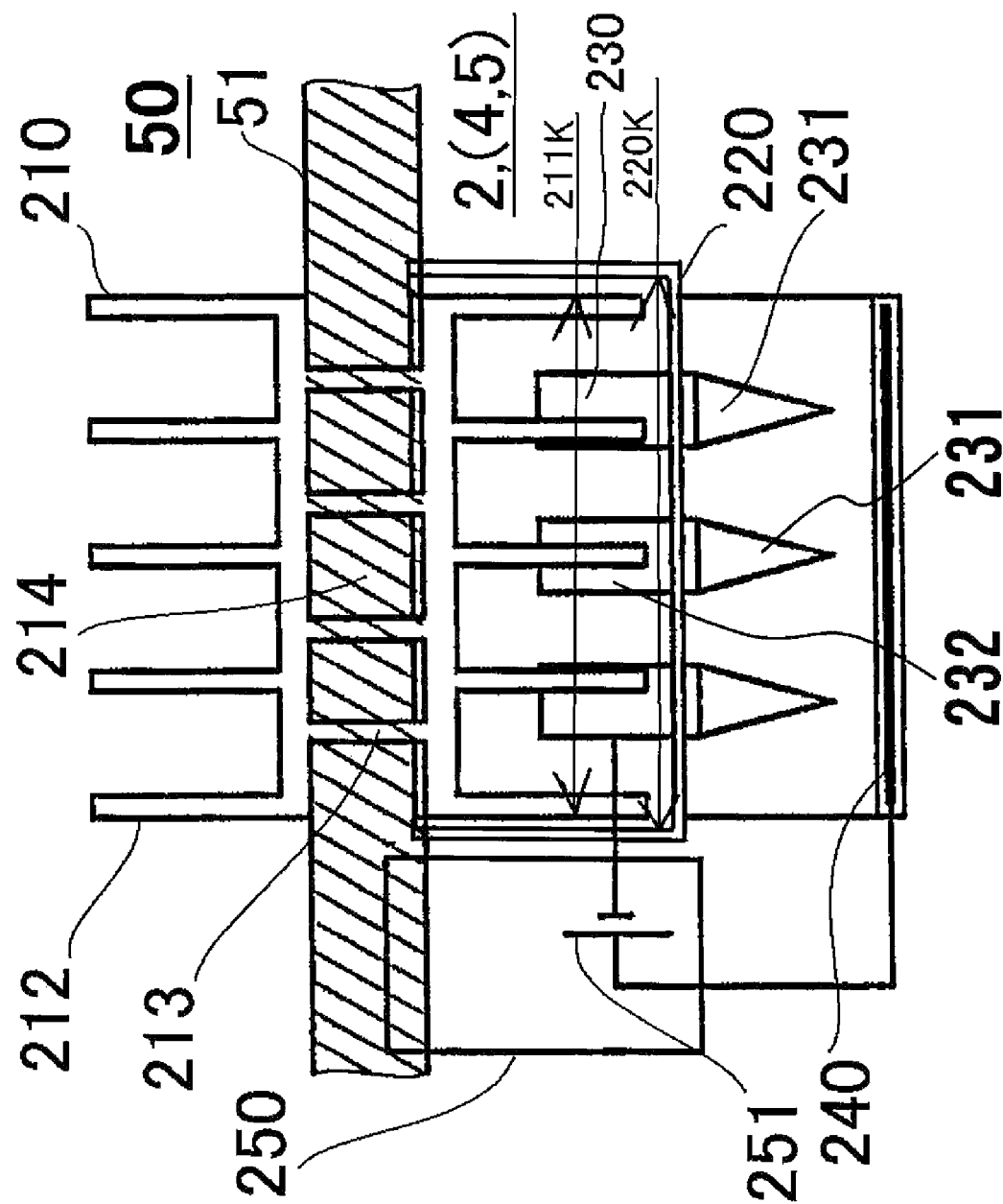
FIG. 7 is a top view of inside the cover, viewed from a top, of the electrostatic atomizing apparatus 200 that is installed in the refrigerator 1 describing the present embodiment.
Figure 8:
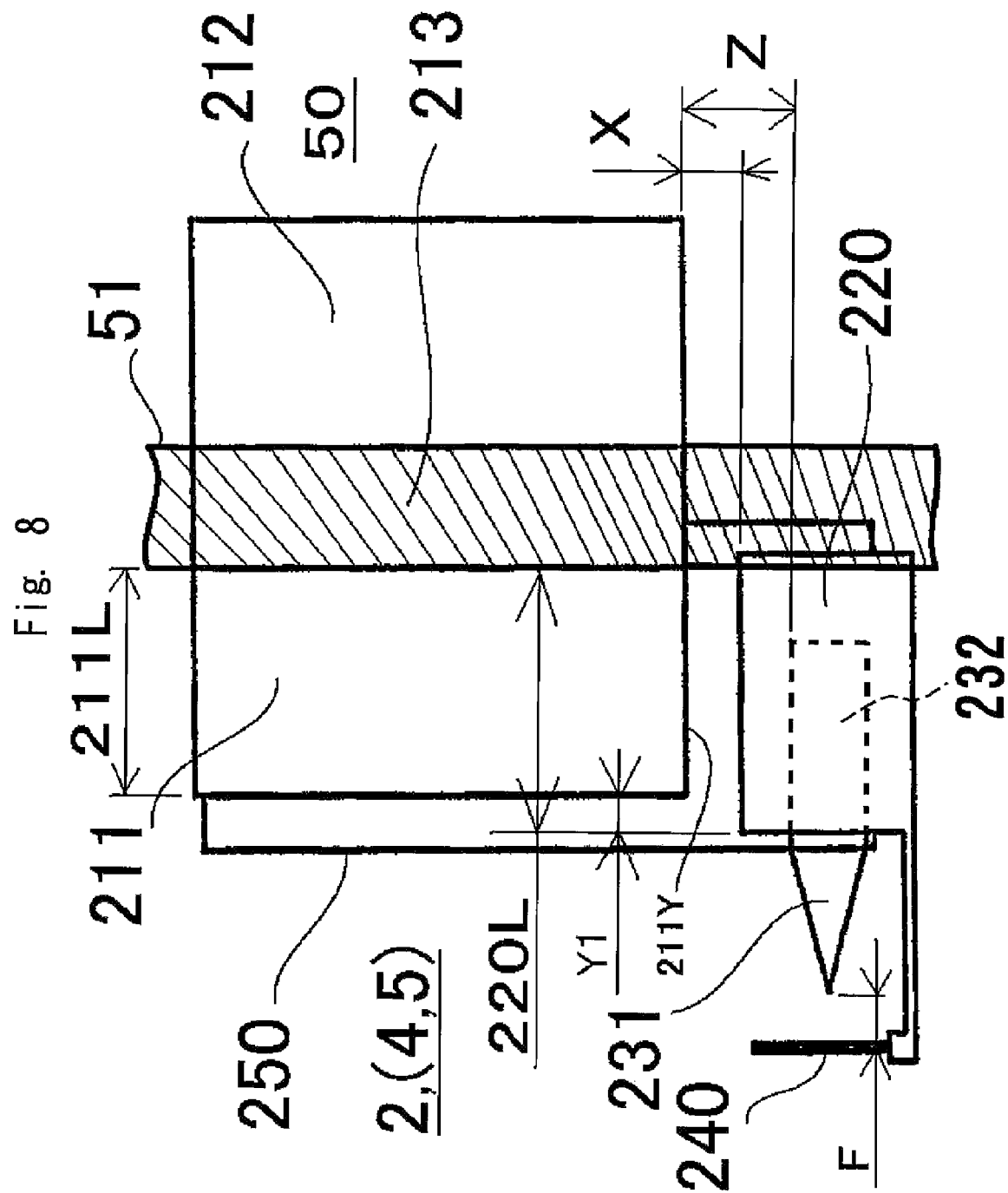
FIG. 8 is a side view of inside the cover, viewed from a side, of the electrostatic atomizing apparatus 200 that is installed in the refrigerator 1 describing the present embodiment.

FIG. 4 is a front view of the inside of the storage compartment from the anterior view in a state the door of the refrigerator 1 shown in FIG. 1 and FIG. 2 is opened, describing the present embodiment. FIG. 5 is a front view of the electrostatic atomizing apparatus 200 in a state where the cover is attached, which is installed in the refrigerator 1 describing the present embodiment, FIG. 6 is a perspective view of inside the cover of the electrostatic atomizing apparatus 200 that is installed in the refrigerator 1 describing the present embodiment, FIG. 7 is a top view of inside the cover, viewed from the top, of the electrostatic atomizing apparatus 200 that is installed in the refrigerator 1 describing the present embodiment, and FIG. 8 is a side view of inside the cover, viewed from a side, of the electrostatic atomizing apparatus 200 that is installed in the refrigerator 1 describing the present embodiment.

The electrostatic atomizing apparatus 200 is installed in the upper rear of inside of a storage compartment (it may be the refrigerating compartment 2, the vegetable compartment 5, etc., for example, and may be any storage compartment) in the present embodiment. In the electrostatic atomizing apparatus 200, the cooling plate 210 as a water supply means is provided in a manner to penetrate through the partition wall 51 (the heat insulating wall) formed at the rear of the refrigerating compartment 2, for example, which is a storage compartment, and to extend across the side of the refrigerating compartment 2, which is the storage compartment, and the side of the cooling air trunk 50. The cooling plate 210 is integrally formed of (or integrally made up by dividing) a material (for example, aluminum, aluminum alloy, copper alloy, etc.) that is resistant to decay and having a good heat conductance, and is made up of a heat absorbing fin part 211 that is provided in a manner to protrude on the side of the refrigerating compartment 2, which is the storage compartment, a heat dissipating fin part 212 that is provided in a manner to protrude on the cooling air trunk 50 side, and a heat conducting part 213 that connects the heat absorbing fin part 211 (a storage compartment side fin part) and the heat dissipating fin part 212 (a cooling air trunk side fin part), wherein the heat conducting part 213 is arranged so that cool air leakage from the cooling air trunk 50 to the storage compartment is approximately sealed, in the partition wall 51 (the heat insulating wall) between the cooling air trunk 50 and the refrigerating compartment 2, to the extent that the temperature in the storage compartment is controllable. The heat absorbing fin part 211 and the heat dissipating fin part 212 need not be particularly protruding if a predetermined cooling effect (heat absorbing performance, heat dissipating performance, etc.) is obtained.

Now, it is described a case with reference to FIG. 8 wherein an electrode holding part 220 in a shape of a container including an opening or a notch for discharging water is provided below (immediately below) a lower end surface 211Y of the heat absorbing fin part 211 (the storage compartment side fin part) via a predetermined clearance X in a vertical direction. The electrode holding part 220 made of a resin is provided below (immediately below) the lower end surface 211Y of the heat absorbing fin part 211 (the storage compartment side fin part) via the approximately 1 mm to 20 mm predetermined clearance X in the vertical direction, and since dew condensation water drops directly over the electrode holding part 220 immediately below, a conveying part for conveying dew condensation water generated in the heat absorbing fin part 211 to the electrode holding part 220 is unnecessary, and the refrigerator 1, which is low in cost and having a simple and compact structure is attained. The discharge electrode 230 is held in the electrode holding part 220, and the discharge electrode 230 is made up of a main body part 232 and a protrusion part 231.

Further, the predetermined clearance X in the vertical direction (dropping direction of dew condensation water) between the lower end surface 211Y of the heat absorbing fin part 211 and the upper end of the electrode holding part 220 is set approximately 1 mm to 20 mm so as to prevent dew condensation water dropping out of the heat absorbing fin part 211 from being blown toward the outside of the container of the electrode holding part 220 by cool air for cooling the inside of the storage compartment, and from dropping to the outside of the container. Additionally, the predetermined clearance X between the heat absorbing fin part 211 and the electrode holding part 220 should be as small as possible in size, preferably be not larger than approximately 10 mm, so that it can be prevented that air inside the storage compartment enters the inside of the container of the electrode holding part 220, a temperature inside the container of the electrode holding part 220 drops, and the dew condensation water inside the container of the electrode holding part 220 freezes.

Further, in this case, a clearance Z between the lower end surface 211Y of the heat absorbing fin part 211, which is the water supply means, and the discharge electrode 230 (the upper surface) should be as small as possible in size, preferably be approximately 1 mm to 30 mm, so that a dropping velocity of the dew condensation water dropping from the heat absorbing fin part 211 to the discharge electrode 230 directly below or the electrode holding part 220 via a space is kept low, the shock at the time the dew condensation water drops over the discharge electrode 230 or the electrode holding part 220 is cushioned, and the dew condensation water is prevented from spattering and jumping out of the container, and the like. In addition, the discharge electrode 230 and the counter electrode 240 are fixed to and held by the electrode holding part 220. However, as for the clearance Z between the lower end surface 211Y of the heat absorbing fin part 211 and the discharge electrode 230, there is a possibility that an electrical current is discharged between the lower end surface 211Y of the heat absorbing fin part 211 and the discharge electrode 230 in a case where a voltage is applied between the discharge electrode 230 and the counter electrode 240 if water droplets are in a state being attached to the surface of the discharge electrode 230, hence it is necessary to maintain a clearance where electric discharge does not occur, and the predetermined clearance Z should preferably be not smaller than 4 mm. Further, since electric discharge is less likely to occur in a state wherein water is not accumulated on the discharge electrode 230, it is preferable that the electrode holding part 220 has a structure such that it is provided with an opening, a notch, etc. to prevent the water from attaching to or accumulating on the surface of the discharge electrode 230 opposed to the heat absorbing fin part 211, which is the water supply means, and thereby preventing the water from accumulating in the holding portion of the discharge electrode 230 in the electrode holding part 220 (or it is also preferable to have a structure such that the water can be discharged from the holding portion of the discharge electrode 230 to prevent the water from accumulating on the surface of the discharge electrode 230, a water reservoir part for accumulating the discharged water is separately provided at a lower part, and thereby preventing the water accumulated in the water reservoir part from contacting with the discharge electrode 230).

Furthermore, the size of the electrode holding part 220 (for example, a width direction size 220K and a length direction size 220L in FIG. 7 and FIG. 8) is approximately the same as the size of the cooling plate 210 (for example, a width direction size 211K and a length direction size 211L in FIG. 7 and FIG. 8), or larger than the size of the cooling plate 210, thereby dew condensation water generated by the cooling plate 210 dropping inside the container of the electrode holding part 220 is caught and does not jump outside.

Next, it is described with reference to FIG. 9 a case where a circumference of an outer surface of a lower end surface 211Y of the heat absorbing fin part 211 (the storage compartment side fin part) is covered for a predetermined length P by a feed-water means cover part 220X, which is an upper inner wall of the electrode holding part 220. Also in this case, the electrode holding part 220 remains to be provided below the heat absorbing fin part 211.

Figure 9:
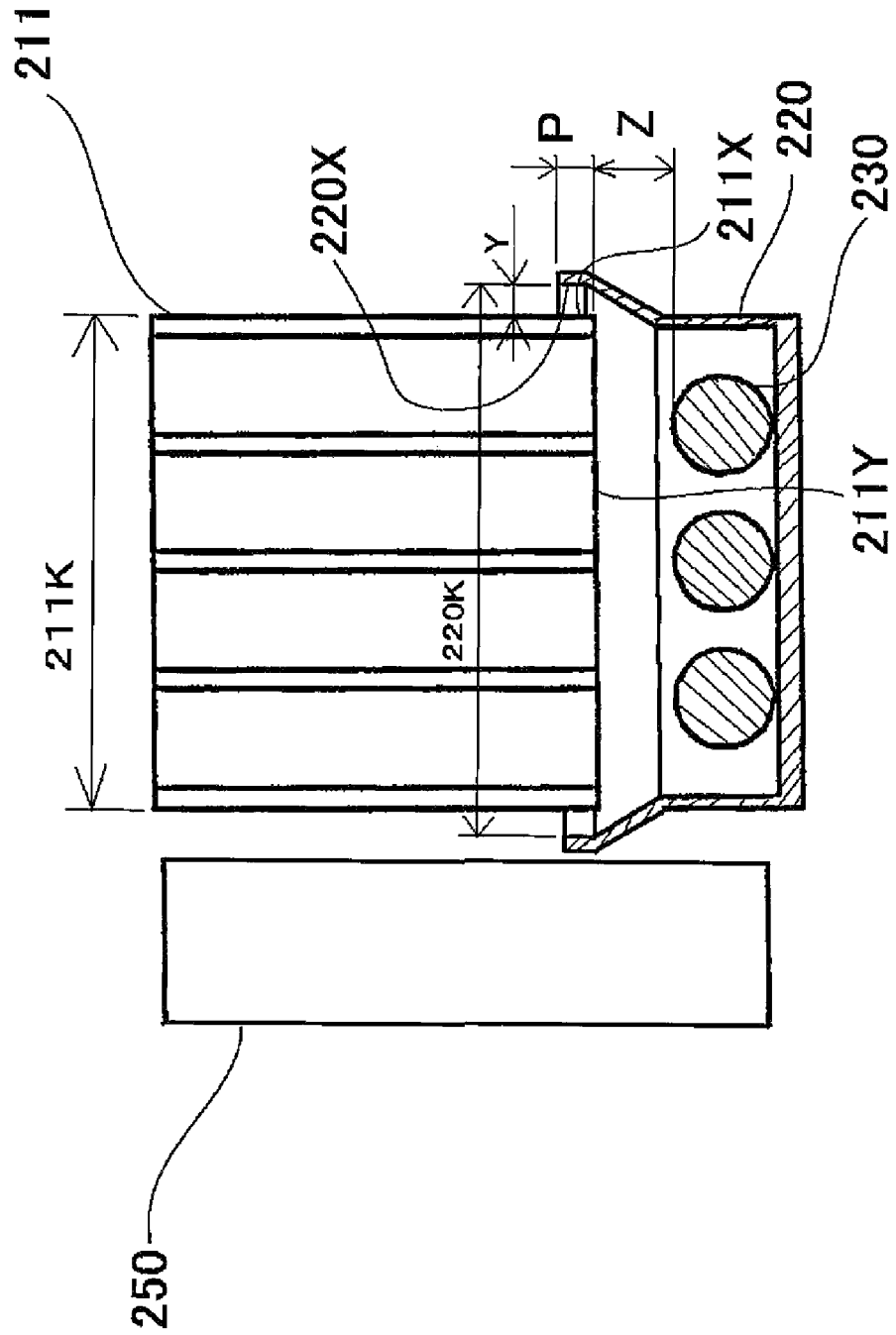
FIG. 9 is a front sectional view of inside the cover, viewed from a front of the refrigerator 1, of the electrostatic atomizing apparatus 200 that is installed in the refrigerator 1 describing the present embodiment.

FIG. 9 is a front sectional view of inside the cover, viewed from the front of the refrigerator 1, of the electrostatic atomizing apparatus 200 that is installed in the refrigerator 1 describing the present embodiment. In the diagram, the circumference of an outer side surface 211X of the lower end surfaces 211Y (the lower parts of the heat absorbing fin parts 211 on the inner side of the refrigerator in the cooling plate 210) of the plural heat absorbing fin parts 211 (the storage compartment side fin parts) is covered for the predetermined length P by the feed-water means cover part 220X, which is the upper inner wall of the electrode holding part 220. Now, predetermined clearances Y (see FIG. 9) and Y1 (see FIG. 8) are provided between the circumference of the outer side surface 211X of the lower end surfaces 211Y (the lower parts of the heat absorbing fin parts 211 on the inner side of the refrigerator in the cooling plate 210) of the heat absorbing fin parts 211 (the storage compartment side fin parts) and the feed-water means cover part 220X, which is the upper inner wall (the feed-water means cover part) of the electrode holding part 220 in a lateral direction (a direction approximately perpendicular to a dropping direction of dew condensation water). Here, the predetermined clearance Y, which is a lateral clearance when the electrostatic atomizing apparatus 200 is viewed from the front, may be different on the both lateral sides (right and left) from the anterior view; however, if the predetermined clearances on the both lateral sides are the same Y, the calculation is as follows:

$$211K+2\times Y=220K$$

The prescribed clearance Y1, which is a front side clearance when the electrostatic atomizing apparatus 200 is viewed from the front, has a relation as follows:

$$211L+Y1=220L.$$

Further, it is preferable that cool air inside the storage compartment is taken into the container of the electrode holding part 220 so as not to have a temperature of dew condensation water dropping inside the container of the electrode holding part 220 rise and bacteria thrive, and that the clearances Y and Y1 between the heat absorbing fin parts 211 and the electrode holding part 220 are not smaller than 1 mm, desirably not smaller than 2 mm. Since the sizes of the predetermined clearances Y and Y1 relate to the dimension of the clearance (the dimension of the opening part formed between the heat absorbing fin parts 211 and the electrode holding part 220 through which cool air can enter inside of the container: the dimension that can be expressed as $220K\times 220L-211K\times 211L$, for example) between the heat absorbing fin part 211 and the container of the electrode holding part 220, the clearances and the dimension of the clearances should be set so that dew condensation water dropping inside the container of the electrode holding part 220 is within a predetermined temperature range (for example, equal to or higher than approximately a freezing point temperature (for example, 0° C.) and equal to or lower than approximately 5° C.) which is equal to or higher than a temperature at which the dew condensation water does not freeze, and which is equal to or lower than a temperature at which bacteria are less likely to thrive in the dew condensation water.

Now, by making dew condensation water dropping from the water supply means (the heat absorbing fin parts 211 of the cooling plate 210), which is the feed-water means, covered so as to be in an approximately sealed state, or at least partially covered by the feed-water means cover part 220X of the electrode holding part 220, a water droplet 275 (see FIG. 16) dropping inside an electrode housing part 225 of the electrode holding part 220 is less likely to be subject to environmental influences (influences of airflow, the temperature, etc.) where the heat absorbing fin parts 211 of the cooling plate 210 and the electrode holding part 220 are situated, hence the dropping dew condensation water is less likely to spatter somewhere by flows of air or cool air, etc., or the dew condensation water generated at the feed-water means (the heat absorbing fin part 211 of the cooling plate 210) is less likely to freeze, and the electrostatic atomizing apparatus 200 that is highly reliable is obtained.

Further, the size (for example, the width direction size 220K and the length direction size 220L) of the upper opening (the feed-water means cover part 220X) of the container of the electrode holding part 220 is the same as the size (for example, the width direction size 211K and the length direction size 211L) of the outer side (the outer surface or the outer circumferential surface) at the lower part of the heat absorbing fin parts 211, or larger than the size of the heat absorbing fin parts 211, and preferably by covering the outer side surface 211X of the heat absorbing fin parts 211 via the prescribed clearances Y and Y1 with a width of approximately 1 mm to 20 mm, air inside the storage compartment is less likely to enter inside of the electrode holding part 220, hence it is possible to prevent the dew condensation water dropping inside the container of the electrode holding part 220 from being frozen. In this case, if the clearances Y and Y1 between the outer side surface 211X of the heat absorbing fin parts 211 and the inner surface (the feed-water means cover part 220X) of the container of the electrode holding part 220 at a position opposed to the position of the outer side surface 211X of the heat absorbing fin parts 211 are too small, the dew condensation water that has condensed at the heat absorbing fin parts 211 may contact the wall surface of the container, and may spill outside the container by surface tension and so on; therefore, the predetermined clearance Y between the outer side surface 211X of the heat absorbing fin parts 211 and the feed-water means cover part 220X, which is the side inner wall of the container opening of the electrode holding part 220, should be equal to or larger than 2 mm, and particularly be 2 mm to 20 mm. Additionally, the prescribed clearance Y1 between the lower front surface of the heat absorbing fin parts 211 and the front inner wall of the container opening of the electrode holding part 220 should be approximately the same as the predetermined clearance Y, equal to or larger than 2 mm, and particularly be 2 mm to 20 mm.

Furthermore, the length P (the length P where the upper end of the feed-water means cover part 220X of the electrode holding part 220 overlaps the heat absorbing fin parts 211, see FIG. 9) between the lower end surfaces 211Y of the heat absorbing fin parts 211 and the upper end of the container (the feed-water means cover part 220X) of the electrode holding part 220 should be set by an experiment and so on so that the dew condensation water dropping from the cooling plate 210 does not spatter or jump outside the container, and should be approximately 1 mm to 20 mm. Now, the sizes of the heat absorbing fin parts 211 and the electrode holding part 220 (the feed-water means cover part 220X) will be defined. As for the heat absorbing fin parts 211, it is defined the width direction size 211K and the length direction size 211L. Further, as for the electrode holding part 220 (the feed-water means cover part 220X), the width direction size 220K and the length direction size 220L are defined. The width direction size 211K of the heat absorbing fin parts 211 is smaller than the width direction size 220K of the electrode holding part 220 by twice the predetermined clearance Yin the width direction. The length direction size 211L of the heat absorbing fin parts 211 is smaller than the length direction size 220L of the electrode holding part 220 (the feed-water means cover part 220X) by a predetermined clearance P1 in the length direction when defining the predetermined clearance in the length direction as P1 (may be the same as or different from the predetermined clearance P in the width direction).

Further, in this case, the clearance Z between the lower end surfaces 211Y (the bottom surface) of the heat absorbing fin parts 211, which is the water supply means, and the upper surface of the discharge electrode 230 should be as small as possible in size so as to keep a dropping velocity of the dew condensation water dropping from the heat absorbing fin parts 211 low, and inhibit shock and spattering, etc. at the time of dropping over the discharge electrode 230 or the electrode holding part 220, and should be equal to or smaller than 30 mm, preferably equal to or lower than approximately 10 mm. In addition, the clearance Z should be as small as possible, equal to or smaller than approximately 10 mm but equal to or larger than 0.5 mm (preferably equal to or lower than 8 mm but equal to or larger than 1 mm), and further, if the clearance Z is equal to or lower than approximately 6 mm but equal to or larger than approximately 1 mm, the dew condensation water can be continuously supplied (moved) from the heat absorbing fin parts 211 to the discharge electrode 230 directly by surface tension or capillary action, hence shock or spattering at the time of dropping can be inhibited. Now, if the clearance Z is smaller than 1 mm, the heat absorbing fin parts 211 and the discharge electrode 230 contact with each other due to vibration at the time of operating, starting and stopping, etc. of the compressor 12 and the cool air circulation fan 14, etc. in the refrigerator 1, which is a cause of failure such as attrition, a crack, etc. and which causes a problem of noise and vibration because of the contact; therefore the clearance Z should preferably be equal to or larger than 1 mm. Additionally, there is a possibility that an electric current is discharged between the lower end surfaces 211Y of the heat absorbing fin part 211s and the discharge electrode 230 in a case wherein a voltage is applied between the discharge electrode 230 and the counter electrode 240 in a state water is attached to the upper surface opposed to the heat absorbing fin parts 211, which is the water supply means, for the discharge electrode 230; therefore, it is necessary not to accumulate water in the discharge electrode 230, and to maintain the clearance where electric discharge does not occur, and the prescribed clearance Z should preferably be equal to or larger than 4 mm.

As described above, the cooling plate 210 (the heat absorbing fin parts 211), which is the water supply means, is provided directly above the discharge electrode 230 (or the electrode holding part 220) via the predetermined clearance Z; therefore, the dew condensation water drops over the directly below electrode holding part 220 (or the discharge electrode 230) in the shape of the container when compared with a case wherein the water supply means is situated at a lower part of the discharge electrode 230 or in a different place, and a conveying part for conveying the dew condensation water generated at the heat absorbing fin parts 211 of the cooling plate 210, which is the water supply means, to the electrode holding part 220 (or the discharge electrode 230) is unnecessary, thus the refrigerator 1 that is compact in size, low in cost, having a simple structure can be obtained.

In the above, it is described an example in which the discharge electrode 230 is provided directly below the lower end surfaces 211Y of the heat absorbing fin parts 211; however, it is also applicable that the discharge electrode 230 is provided at the side of the outer side surface 211X of the lower end surfaces 211Y of the heat absorbing fin parts 211. In this case, in order to supply dew condensation water that has condensed at the heat absorbing fin parts 211 to the discharge electrode 230, a predetermined side clearance between the side surface of the heat absorbing fin parts 211 and the discharge electrode 230 should preferably be as small as possible so that the dew condensation water generated at the heat absorbing fin parts 211 is transmitted and can be supplied to the discharge electrode 230 by surface tension or capillary action without directly dropping downward from the heat absorbing fin parts 211, and should be equal to or smaller than approximately 5 mm but equal to or larger than approximately 0.2 mm (preferably equal to or smaller than approximately 3 mm but equal to or larger than approximately 0.5 mm). When the predetermined side clearance is set equal to or smaller than approximately 5 mm but equal to or larger than approximately 0.2 mm (preferably equal to or smaller than approximately 3 mm but equal to or larger than approximately 0.5 mm), the dew condensation water can be continuously supplied to the discharge electrode 230 directly from the heat absorbing fin parts 211 by surface tension or capillary action; therefore, it is possible to prevent that the dew condensation water is not supplied to the discharge electrode 230. Now, if the predetermined side clearance is smaller than 0.2 mm, the heat absorbing fin parts 211 and the discharge electrode 230 contact with each other due to vibration at the time of operating, starting and stopping, etc. of the compressor 12 and the cool air circulation fan 14, etc. in the refrigerator 1, which is a cause of failure such as attrition, a crack, etc., and which causes a problem of noise and vibration because of the contact; therefore the predetermined side clearance should preferably be equal to or larger than 0.2 mm.

Furthermore, by fixing the electrode holding part 220 to the partition wall 51 below (directly below) the heat absorbing fin parts 211 (the storage compartment side fin parts) with a screw, etc., a conveying part for conveying the dew condensation water condenses at the heat absorbing fin parts 211 to the electrode holding part 220 is unnecessary, and further, the installation site of the electrode holding part 220 inside the storage compartment can be concentrated in the rear surface of the storage compartment or the side surface of the storage compartment, and the electrostatic atomizing apparatus 200 or the electrode holding part 220, etc. can be formed integrally with the rear surface of the storage compartment or the side surface of the storage compartment; therefore, an attaching part needs not be provided separately, and the projecting volume inside the storage compartment can be reduced, hence the structure is made simple and compact in size, and the inner volume inside the storage compartment can be increased by a corresponding volume by which the installation area of the electrode holding part 220 is made small and compact, thus, the refrigerator 1 that is low in cost, user friendly, having a large inner volume and improved storage efficiency can be obtained.

Further, in the electrode holding part 220, at least one or more pieces (plural pieces of two or more are desirable) of the discharge electrodes 230 formed of foam metal such as titanium are provided so as to protrude (so as to protrude from a wall surface of the electrode holding part 220) toward the outside of the container via a notch or a hole formed in the wall surface (a front wall or a side wall) of the electrode holding part 220 or an upper end of the wall surface (the front wall or the side wall) of the electrode holding part 220. In the present embodiment, since the foam metal such as titanium with pore diameters of 10 to 800 μm (preferably with pore diameters of 50 to 300 μm, preferably between 50 and 150 μm), and a voidage of 60 to 90% (preferably 70 to 80%), etc. is used, capillary force is large and water as a conductive material is efficiently applied electricity, hence it is easy to set an applied voltage and generate nano-size mist reliably. The discharge electrode 230 is made up of the main body part 232 and the protrusion part 231, and the discharge electrode 230 needs not penetrate through the electrode holding part 220, and it is only necessary that the protrusion part 231 is provided so as to protrude from the electrode holding part 220.

As described above, since the discharge electrode 230 is provided in the front surface or the side surface of the electrode holding part 220 so as not to penetrate lower than the bottom face of the electrode holding part 220, there is no possibility that water leaks downward from a clearance at the position that the discharge electrode 230 is installed in the bottom face of the container of the electrode holding part 220. In a structure wherein the discharge electrode 230 is attached to the bottom face of the container, a seal structure around the position whereto the discharge electrode is attached becomes complicated due to necessity of supplying water to the discharge electrode 230; however, in a case wherein the discharge electrode 230 is installed in the front wall or the side wall of the container, by selecting an installed position of the discharge electrode 230 such as a position of a notch or a hole, etc. so that at least a part of the wall surface (the front surface wall or the side surface wall) remains in the wall surface of the electrode holding part 220 whereto the discharge electrode 230 is installed and by forming a water discharge spout at another position, water does not leak downward by sliding down the discharge electrode 230 from the installed position of the discharge electrode 230 and the seal structure can be simplified; therefore, treatment of the leaked water is unnecessary, the assembly efficiency is increased, the number of the components can be reduced, and the cost can be reduced.

Now, the heat absorbing fin part 211 includes plural heat absorbing fin plates 211a, 211b, 211c, 211d and 211e, and the heat dissipating fin part 212 includes plural heat dissipating fin plates 212a, 212b, 212c, 212d and 212e, which enable efficient heat absorption and heat dissipation. In addition, at least one discharge electrode 230 (the plural discharge electrodes 230b, 230c and 230d are respectively disposed below (directly below) each of the plural heat absorbing fin plates 211b, 211c and 211d in the diagram) is disposed below (directly below) at least one heat absorbing fin plate (for example, the heat absorbing fin plates 211b, 211c and 211d in the diagram) among the plural heat absorbing fin plates 211a, 211b, 211c, 211d and 211e of the heat absorbing fin parts 211, and dew condensation water that has condensed at the plural heat absorbing fin plates 211b, 211c and 211d drops over the discharge electrode 230 directly below each fin, thereby water can be efficiently supplied to the discharge electrode 230. It is defined here that the intervals between the plural heat absorbing fin plates 211b, 211c and 211d are predetermined intervals (for example, approximately 0.5 mm to 3 mm). The predetermined intervals are desirably equal to or larger than 0.5 mm in order to prevent the intervals between the fin plates from being clogged with dust, etc. and water droplets that have condensed due to too small intervals between the fin plates from being hard to drop by surface tension, and are desirably equal to or smaller than 3 mm since when the intervals between the fin plates are increased, the number of the fin plates is reduced and fin efficiency becomes inefficient. Therefore, in the present embodiment, the predetermined intervals between the plural heat absorbing fin plates 211b, 211c and 211d are set equal to or larger than 0.5 mm but equal to or smaller than 2 mm.

Thus, it is possible to supply water to the discharge electrode 230 even when dew condensation water is small in amount and dew condensation water is not accumulated in the electrode holding part 220, hence there is no possibility that mist cannot be sprayed in a storage compartment due to lack of dew condensation water, and the refrigerator 1 equipped with electrostatic atomizing apparatus 200 that is high-performance and highly reliable can be provided. Further, since a conveying part that conveys dew condensation water that has condensed at the heat absorbing fin part 211 to the electrode holding part 220 is unnecessary, and there is no possibility that the conveying part is clogged with dust, etc. and dew condensation water is not supplied to the discharge electrode 230, the electrostatic atomizing apparatus 200 and the refrigerator 1 simple in structure, low in cost and highly reliable can be provided.

Figure 10:
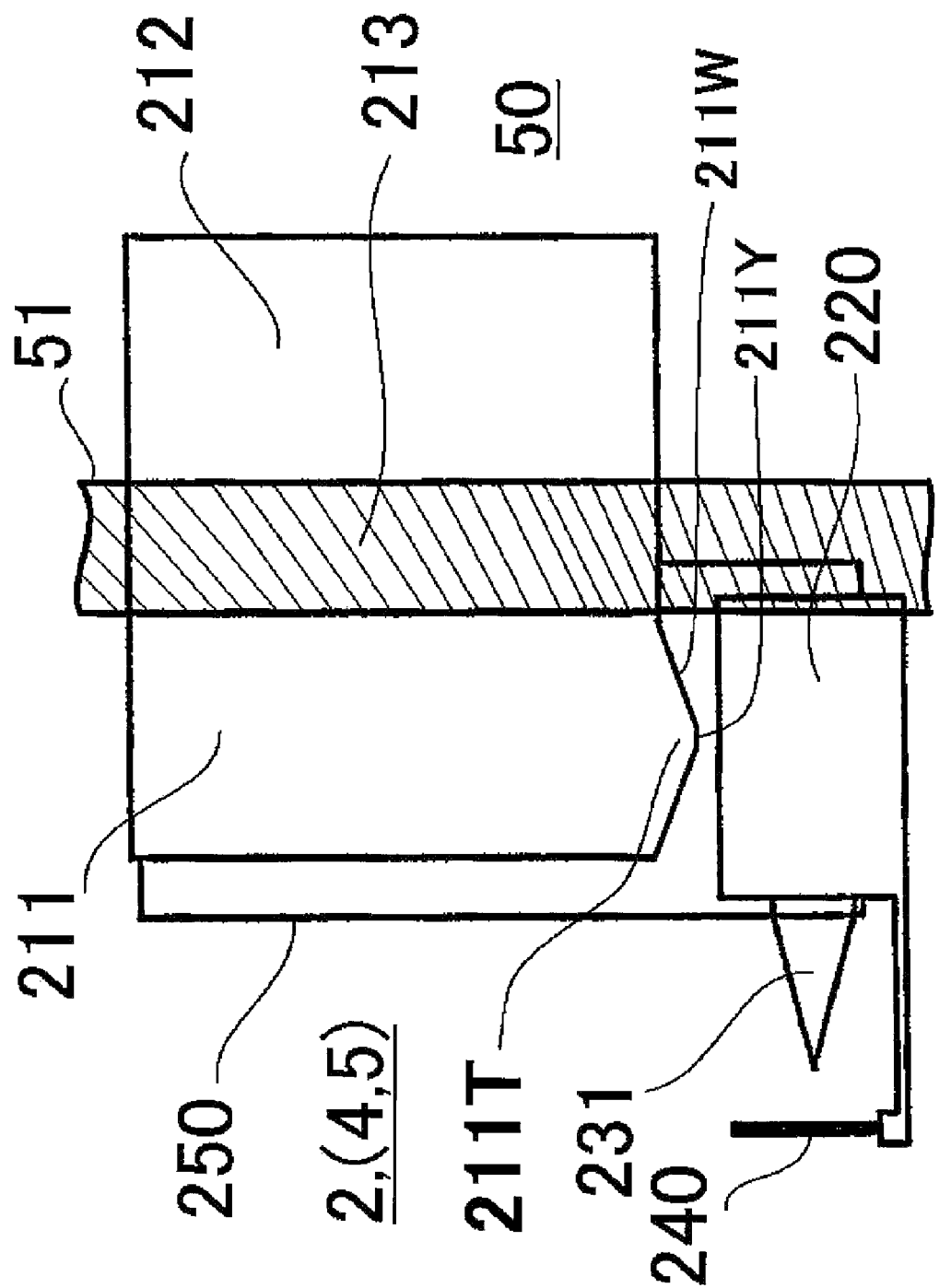
FIG. 10 is a side view of inside the cover, viewed from a side, of the electrostatic atomizing apparatus 200 that is installed in the refrigerator 1 describing the present embodiment.

Now, in the present embodiment, it is configured such that it is possible to have the dew condensation water that has condensed in the heat absorbing fin part 211 drop into the electrode holding part 220 after being accumulated in one point (or required prescribed points (for example, about 1 to 4 points)). FIG. 10 is a side view of inside the cover, viewed from the side, of the electrostatic atomizing apparatus 200 that is installed in the refrigerator 1 describing the embodiment. As shown in the diagram, a slant part (a tilt portion) is formed in a shape of the lower end of the heat absorbing fin part 211 and dew condensation water is collected in a part where it is desired to collect the dew condensation water after being led along the slant part. By forming the shape of the lower end of the heat absorbing fin part 211 in a shape having a slant part 211W and a protrusion part 211T as a shape to protrude downward, such as an approximately triangle shape, a trapezoidal shape, a conical shape, a sawtooth shape, etc., it is possible to set the dew condensation water to slide down the slant part 211W, to be collected at the protrusion part 211T (portion where it is desired to collect the dew condensation water), and to drop into a required portion in the electrode holding part 220; therefore, the dropping position of the dew condensation can be specified and perceived, thus the size of the electrode holding part 220 can be reduced, and the electrostatic atomizing apparatus 200 that is compact in size can be obtained.

Figure 11:
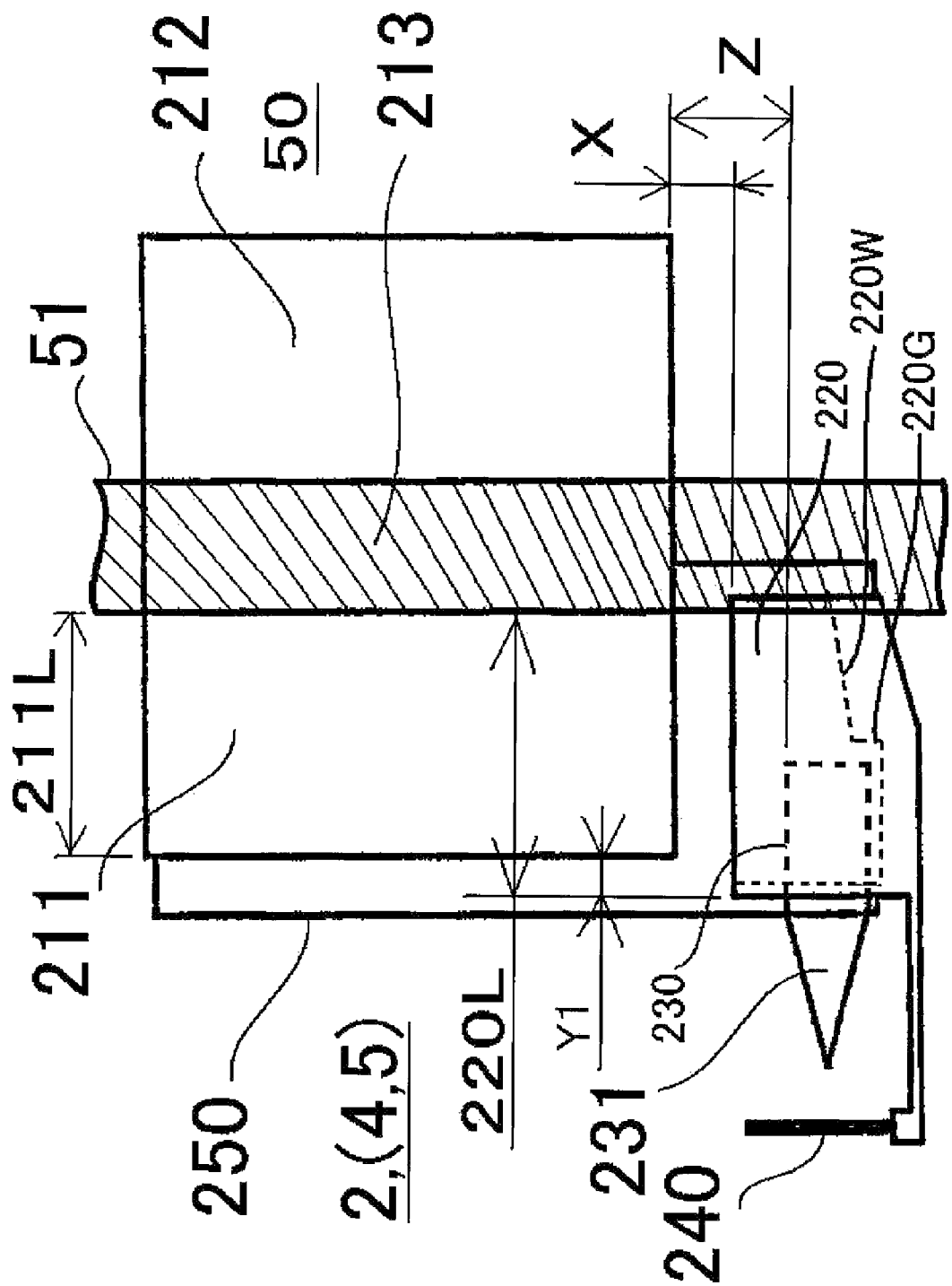
FIG. 11 is a side view of inside the cover, viewed from a side, of the electrostatic atomizing apparatus 200 that is installed in the refrigerator 1 describing the present embodiment.

Further, as shown in FIG. 11, by forming a slant part 220W and a water concentration part 220G also in the shape of the container of the electrode holding part 220, dew condensation water can be concentrated at a predetermined area (for example, at the position of the discharge electrode 230) in the container even when the amount of the dew condensation water is small, and mist can be sprayed without lack of the dew condensation water. FIG. 11 is a side view of inside the cover, viewed from the side, of the electrostatic atomizing apparatus 200 that is installed in the refrigerator 1 describing the embodiment. In the diagram, the electrode holding part 220 consists of the slant part 220W that is inclined downward, and the water concentration part 220G that is adjacently installed on the lower side (in the lower part) of the slant part 220W, forming a concave portion. The discharge electrode 230 is allocated inside the water concentration part 220G of the electrode holding part 220. By forming the container shape of the electrode holding part 220 in this way, dew condensation water is collected at the water concentration part 220G when the dew condensation water generated at the heat absorbing fin part 211 drops inside the electrode holding part 220, since the dew condensation water dropping in the slant part 220W flows in the water concentration part 220G along the inclination.

Therefore, since the dropping dew condensation water flowing along the slant part 220W flows into and concentrates in the water concentration part 220G, there is no lack of the dew condensation water in the discharge electrode 230 allocated in the water concentration part 220G, and the discharge electrode 230 continues to be submerged in the dew condensation water at any time, hence the dew condensation water can be efficiently collected in the water concentration part 220G wherein the discharge electrode 230 is allocated even when the dew condensation water is small in amount, and mist can be stably sprayed without lack of the dew condensation water. Further, since the dew condensation water concentrates in the water concentration part 220G, the discharge electrode 230 can be shortened in accordance with the size of the water concentration part 220G since the dew condensation water concentrates in the water concentration part 220G without making the length of the discharge electrode 230 long and having the discharge electrode 230 absorb as much dew condensation water as possible. Thus, the electrostatic atomizing apparatus 200 and refrigerator 1 that are compact in size and low in cost can be obtained. Further, since the length of the discharge electrode 230 can be shortened, the length to the protrusion part 231 (a tip section) in the discharge electrode 230 can be also shortened. Additionally, the dew condensation water can be delivered inside the discharge electrode 230 formed of the foam metal, etc. to the protrusion part 231 (the tip section) by capillary action in a short time as the length of the discharge electrode 230 is short, and the time until nano-size fine mist is sprayed by the electrostatic atomizing apparatus 200, which is the mist spraying apparatus, can be shortened substantially.

However, if an electric discharge occurs between the discharge electrode 230 and the heat absorbing fin part 211, which is the water supply means, when a voltage is applied to between the discharge electrode 230 and the counter electrode 240 in a state where water is accumulated in the water concentration part 220G and water is attached to the discharge electrode 230, a water discharge spout should be formed in the water concentration part 220G so that water is not accumulated. In this way, even when the water discharge spout is formed in the water concentration part 220G so that water is not accumulated, water can be supplied to the protrusion part 231 (the tip section) by capillary action, by making the discharge electrode 230 directly contact with the water from the slant part 220W or the dew condensation water from the heat absorbing fin part 211; therefore, there is no possibility of lack of water in the protrusion part 231, and mist can be sprayed stably.

Further, the heat conducting part 213 of the cooling plate 210 as described in FIG. 6 includes plural heat conducting plates 213a, 213b, 213c and 213d, and plural void parts 214 (the void parts 214a, 214b and 214c) between the heat conducting plates, wherein the plural void parts 214 have structures that heat insulation materials can be filled or inserted therein; therefore, it is configured such that heat is not transferred too much to the heat absorbing fin part 211 even when the heat dissipating fin part 212 is cooled too much, and even when the heat dissipating fin part 212 on the side of the cooling air trunk 50 is cooled too much by cool air that is flowing through the cooling air trunk 50 and is blown from the cooler compartment 131, the heat absorbing fin part 211 on the storage compartment (for example, the refrigerating compartment 2) side is less likely to freeze. Since the dew condensation water cannot be generated when the heat absorbing fin part 212 freezes, the heat absorbing fin part 212 is made to be less likely to freeze with a structure wherein heat can be conducted but is difficult to be conducted. This effect is achieved by forming at least one of the void parts 214.

That is, in the present embodiment, since at least one of the void parts 214 is formed in the heat conducting part 213 of the cooling plate 210, by adjusting the length of the heat conducting part 213 (for example, as shown in FIG. 6 to FIG. 11, the length between the heat dissipating fin part 212 and the heat absorbing fin part 211 (the length of the heat conducting part 213 in the length direction of the refrigerator) when the cooling plate 210 is arranged in an order of the heat absorbing fin part 211, the heat conducting part 213, and the heat dissipating fin part 212 in a direction from the front side to the back of the refrigerator 1), the size of the void parts 214 (the width-direction length, the length-direction length, the height-direction length, the size of the opening dimension, and the volume, etc. of the heat conducting part 213), the type, the material and so on of the gas such as air, liquid, a heat insulating material, etc. that is filled or inserted in the void parts 214 so as to obtain a prescribed cooling performance and temperature characteristic, it is possible to set the heat absorbing fin part 211 on the storage compartment (for example, the refrigerating compartment 2) side so as not to be frozen even when the heat dissipating fin part 212 on the cooling air trunk 50 side is cooled too much by the cool air that is blown from the cooler compartment 131 and flowing through the cooling air trunk 50. Therefore, a temperature control means such as a heater that performs temperature control over the cooling plate 210 is unnecessary, and a low-cost and simply structured electrostatic atomizing apparatus 200 and refrigerator 1 equipped with the electrostatic atomizing apparatus 200 can be provided. Meanwhile, even when the cooling plate 210 has a structure less likely to be frozen in reverse, by selecting the shape and the thickness of the plural heat conducting plates of the heat conducting part 213, the type, the material and so on of a filling material or a heat insulating material that is sealed in the void parts 214 so as to obtain a prescribed cooling performance and temperature characteristic, the cooling plate 210 can be adjusted to obtain the prescribed cooling performance.

The temperature of the heat absorbing fin part 211 should be adjusted by controlling the temperature or the air volume of cool air in the cooling air trunk 50, which may be performed by control of opening and closing the refrigerating compartment damper 55 installed in the cooling air trunk 50 on the upstream side of a storage compartment (for example, the refrigerating compartment 2), or since the plural heat conducting parts 213 are installed, the temperature of the heat absorbing fin part 211 may be moderately adjusted by selecting (altering) the thickness, the shape or the material, etc. of the plural heat conducting parts 213 so as to obtain the prescribed cooling performance and temperature characteristic, or may be performed by combining the temperature control and the air volume control of the cool air, and altering of the shape, thickness or the material of the heat conducting parts 213. Further, the number of the heat conducting parts 213 may be selected (increased or decreased), or the filling rate of the heat insulating material or the type of the heat insulating material (for example, urethane foam or vacuum insulating material, etc.) inserted in the void parts 214 may be selected so as to obtain the prescribed cooling performance and temperature characteristic. In addition, the cooling plates and the heat conducting plates may all have the same thickness, length, or the shape, or may differ in shape, thickness or length individually.

Further, it is also applicable that the cooling plate 210 and a cooling plate insulating material 511 are integrally formed (or the cooling plate 210 and the cooling plate insulating material 511 such as urethane, vacuum insulating material, etc. are formed together) as a kit component 512 to be a separate component by foaming and filling urethane or vacuum insulating material, etc. in the void parts 214 formed in the heat conducting parts 213 in the cooling plate 210, or by sealing gas such as air, etc., liquid or heat insulating material, etc. in the void parts 214. The cooling plate insulating material 511 and the kit component 512 will be described below (in the description for FIG. 18 through FIG. 20).

In this case, by using a seated organic fiber aggregate with a layered structure as a core material for the vacuum insulating material, an affect on a human body by dust at the time of dismantlement or recycling is reduced compared to a case where glass fibers are used as the core material. Furthermore, in a case wherein the core material is cut to a prescribed length or a prescribed width, inserted in an external casing material with gas barrier performance, depressurized to an approximate vacuum state, and sealed as an approximately sealed structure, if short fibers shorter than the seat in the length direction or in the width direction are used for the organic fiber assembly, the length of the fibers is shortened correspondingly as the fibers are cut when an end surface or a hole drilling portion of the core material is cut; therefore, if the original length of the fibers is short, there is a possibility that left fibers that are left in the sheet by cutting become extremely short, in which case the left fibers cannot twine about other organic fibers in the sheet, sticking out from or flying from the cut surface (end surface) of the core material, that the left fibers of the core material are interleaved between the seal surface of the external casing material whereby seal failure is caused and the approximate vacuum state cannot be kept, and that in the end, heat insulation performance as the vacuum insulating material is impaired. Further, if the extremely short left fibers stick out from or fly from the cut surface (end surface) of the core material, the left fibers may be taken in a vacuum pump when vacuuming is performed by the vacuum pump, which may cause the vacuum pump to malfunction.

However, by using long fibers (for example, fibers with a prescribed consecutive length of equal to or longer than the sheet in the length direction or in the width direction) longer than the length in the length direction or the width direction of the sheet for the organic fiber aggregate making up the core material, left fibers that are left in the sheet do not become extremely short even when the end surface is cut; therefore, the left fibers twine about other organic fibers in the sheet and do not stick out from or fly from the cut surface of the core material, and there is no possibility that the left fibers of the core material are interleaved by the seal surface of the external casing material, that seal failure is caused and that the approximate vacuum state cannot be kept. Further, there is no possibility that the vacuum pump is damaged. Therefore, it is possible to obtain the heat insulation material, the electrostatic atomizing apparatus 200 and the refrigerator 1 having high recyclability, high insulation property without occurrence of seal failure, etc., being highly reliable, and using less energy.

Furthermore, using long fibers (for example, fibers with a prescribed consecutive length of equal to or longer than the length direction or the width direction of the sheet) longer than the length in the length direction or the width direction of the sheet for the organic fiber aggregate forming the core material is also effective in a case wherein a vacuum insulating material with a hole is desired to be obtained by performing hole drilling in the core material, and it is applicable to use a vacuum insulating material using long fibers for the core material with a hole approximately the same as the electrostatic atomizing apparatus 200 or larger than the electrostatic atomizing apparatus 200 in size for the partition wall 51 of a storage compartment, and to house the electrostatic atomizing apparatus 200 inside the hole. In this way, a refrigerator having high heat insulation property and antibacterial property, capable of bacterial eradication and preventing from drying can be obtained. Similarly, it is also applicable to house the other functional components other than the electrostatic atomizing apparatus 200 in the hole of the vacuum insulating material. Further, since there is no possibility in the vacuum insulating material using the long fibers for the core material that the vacuum insulating material cannot keep an approximately vacuum state due to seal failure as mentioned above, the vacuum insulating material should be used not only for the electrostatic atomizing apparatus 200, and by using the vacuum insulating material as a heat insulation material for performing heat insulation of the refrigerator 1, it is possible to provide the refrigerator 1 having high recyclability, high insulation property without the occurrence of seal failure, and using less energy.

In this case, the cooling plate insulating material 511 should be set to have a predetermined size approximately equivalent to or larger than the size (for example, the width-direction length and the height-direction length) of the heat conducting part 213 in the cooling plate 210, and the cooling plate insulating material 511 should be installed by being embedded in the partition wall 51 of a storage compartment (for example, the refrigerating compartment 2) and fixed, and so on. The cooling plate insulating material 511 here should be embedded in the partition wall 51 of the storage compartment by forming a through hole with a size approximately the same as or larger than the size of the cooling plate insulating material 511 in the rear wall of the storage compartment (for example, the refrigerating compartment 2), and so on.

(Making the Electrostatic Atomizing Apparatus 200 into a Kit)

As shown above, the cooling plate insulating material 511 (for example, urethane foam or a vacuum insulating material, etc.) with the predetermined size including also the circumference of the heat conducting parts 213 in the cooling plate 210, and the cooling plate 210 are integrally formed (or formed together), or the like, into the kit component 512 as the separate component, and detachably installed in the rear wall of the storage compartment, thereby assembling efficiency at the time of embedding and fixing the kit component 512 in and to the rear of the storage compartment (for example, the refrigerating compartment 2) can be increased. Now, it is also applicable that only the cooling plate 210 is integrally formed into a kit component by foaming and filling urethane or sealing a vacuum insulating material, gas such as air, liquid, a heat insulating material, etc. in the void parts 214 formed in the heat conducting parts 213 in the cooling plate 210, and so on, and it is also applicable that the heat absorbing fin part 211 and the heat dissipating fin part 212 are separately composed, and formed together to be the kit component 512 as the separate component by intervening a heat insulating material or a Peltier element between the heat absorbing fin part 211 and the heat dissipating fin part 212, which is installed in a detachable manner. By performing heat transfer forcibly using the Peltier element as described, the kit component can be easily applied and mist can be sprayed without performing special processing, etc. in a home electrical appliance such as an air conditioner, a humidifier and an air purifier.

Further, by forming components other than the cooling plate 210, for example, the electrode holding part 220, the discharge electrode 230, the counter electrode 240, and a high-voltage power supply part 250, etc. as needed together with the cooling plate insulating material 511 into the kit component 512, assembling efficiency of the electrostatic atomizing apparatus 200 is increased. Additionally, when a performance failure occurs in or at a time of breakdown of the electrostatic atomizing apparatus 200, only the kit component 512 made up of the components separate from the partition wall 51 can be detached from the rear wall of the storage compartment, hence it becomes easy to replace or repair the components. Further, the kit component 512 can be easily detached at a time of dismantling and recycle of the refrigerator 1, and the recycling efficiency is improved. Now, it is applicable to use a vacuum insulating material using long fibers for the core material with a hole, which is approximately the same as the cooling plate insulating material 511 wherein the kit component 512 is formed, or larger in size than the cooling plate insulating material 511 for the partition wall 51 of a storage compartment, and to house the kit component 512 or the cooling plate insulating material 511 wherein the kit component 512 is formed inside the hole. In this way, the refrigerator 1 having high heat insulation property, good assembling, dismantling and recycling efficiency, and antibacterial property, capable of bacterial eradication and preventing from drying, and further, using less energy can be obtained.

The high-voltage power supply part 250 (see FIG. 8) which may be broken due to dew condensation or freezing, etc. when installed inside the storage compartment should be located as a separate component at a place where dew condensation or freezing, etc. does not occur and, for example, should be connected by a thermally insulated wire lead, etc. For instance, it is applicable that the high-voltage power supply part 250 is integrated with the control device 30 installed in the upper back surface of the refrigerator 1 or is located inside a control device housing compartment wherein the control device 30 is housed, and is connected with the electrostatic atomizing apparatus 200 by a connecting wire such as a wire lead via a connector so that the connection can be simply released. The located place of the high-voltage power supply part 250 is not limited to the housing compartment of the control device 30, and may be any place where dew condensation or freezing, etc. does not occur, for example, a place which is on contact with an inside of a storage compartment through an insulated wall. Further, by making the high-voltage power supply part 250 have waterproof property, or low temperature resistance, the high-voltage power supply part 250 can be installed in any storage compartments inside the refrigerator 1.

In the above, it is described that the cooling plate 210 and the cooling plate insulating material 511 are integrally formed (or the cooling plate 210 and the cooling plate insulating material 511 such as urethane, a vacuum insulating material, etc. are formed together) into the kit component 512 to be the separate component, and detachably installed by foaming and filling urethane or a vacuum insulating material, etc. or by enclosing gas such as air, liquid, a heat insulating material, etc. in the void parts 214 formed in the heat conducting parts 213 of the cooling plate 210; however, it is also applicable that the cooling air trunk 50 (a part of the cooling air trunk 50) located at the back surface of the cooling plate insulating material 511 is also included in and made into the kit component to be detachably installed. In this way, the assembling is easy, and by embedding in the cooling air trunk in the area that is made into the kit (for example, an approximately the same size as the cooling plate insulating material 511) a functional component that performs a predetermined operation such as a damper device, a deodorizing device, a bacterial eradication device, etc. or a component needing replacement, such as a filter device, a bacterial eradication device, etc. that becomes ineffective due to clogging and as time passes, the kit component 512 can be detached at the time of breakdown or servicing, and services such as inspection, repair, replacement, etc. can be easily performed; therefore, the service performance is enhanced, and further, the recycling efficiency is also improved.

Figure 18:
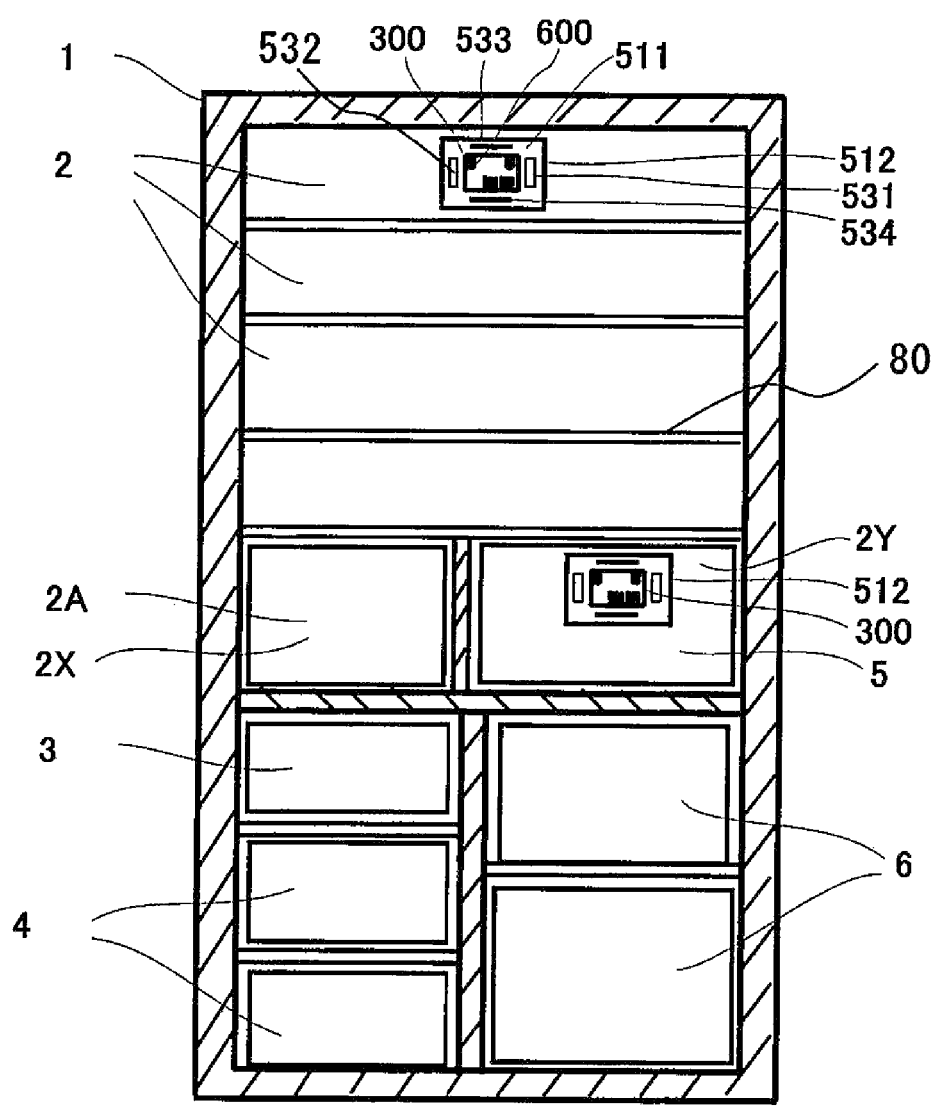
FIG. 18 is a front view of the refrigerator in a state where the door is opened, describing the embodiment of the present invention.
Figure 19:
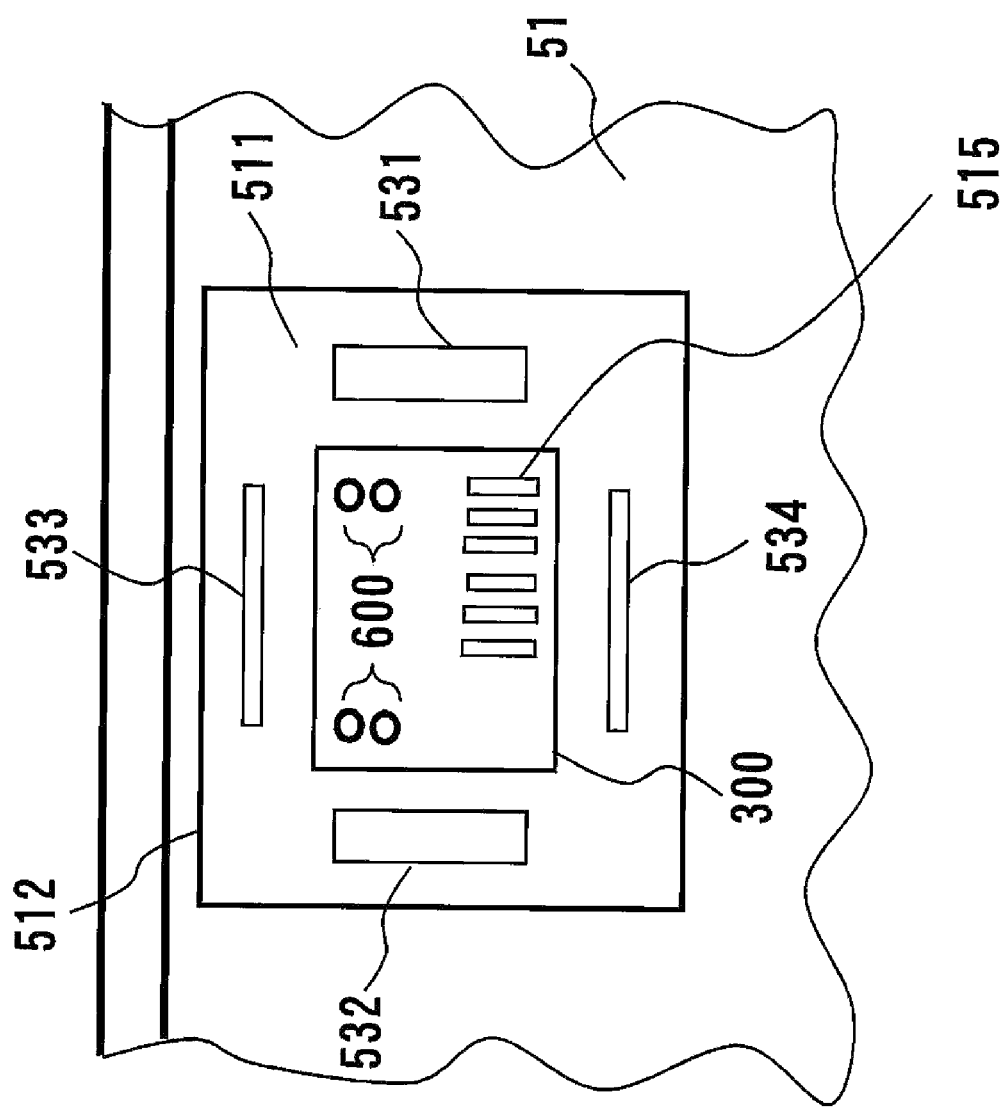
FIG. 19 is a front view of the electrostatic atomizing apparatus 200 in a state of being attached the cover, which is installed in the refrigerator 1 describing the embodiment of the present invention.
Figure 20:
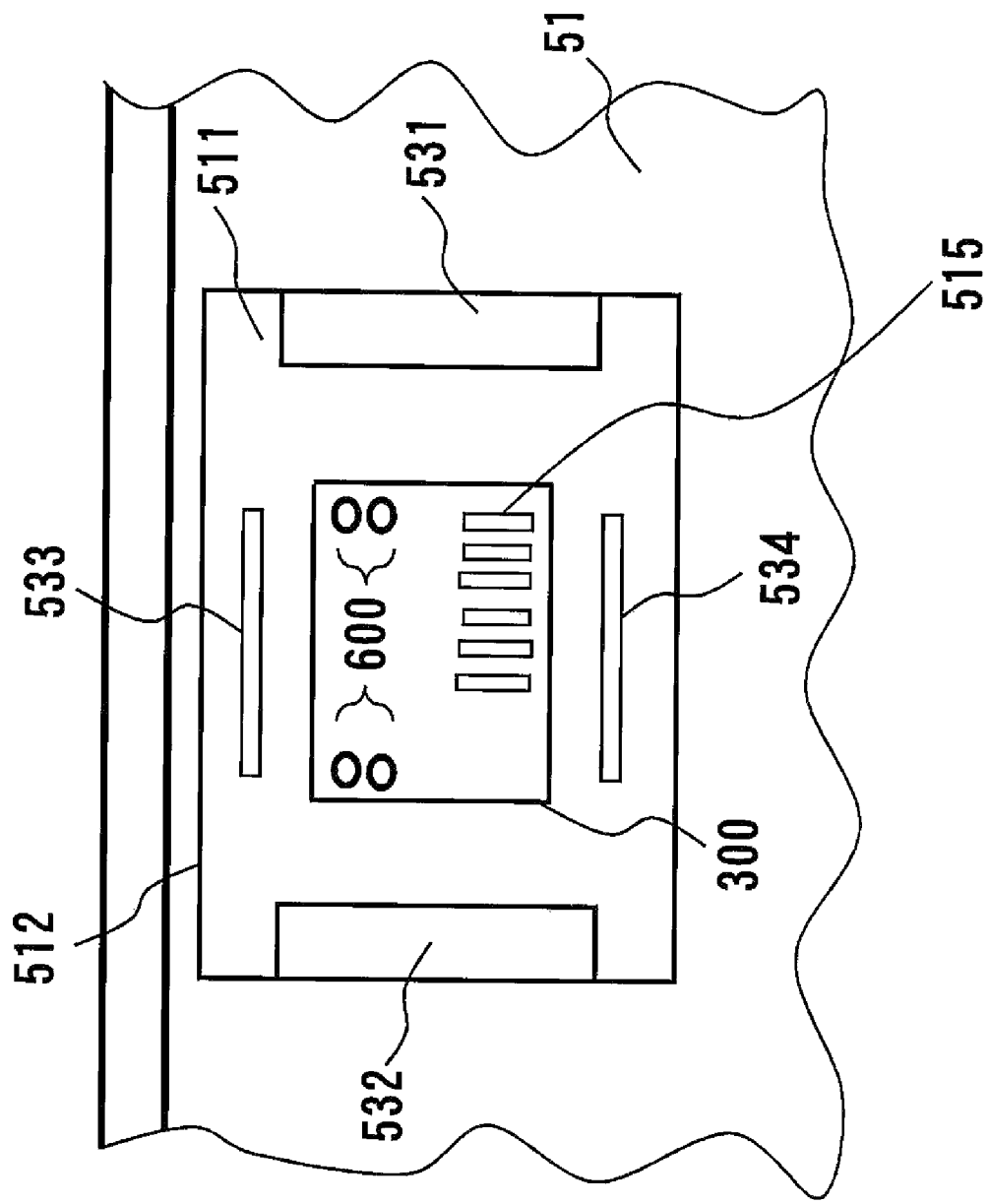
FIG. 20 is a front view of the electrostatic atomizing apparatus 200 in a state of being attached the cover, which is installed in the refrigerator 1 describing the embodiment of the present invention.

Now, it is applicable to form a cool air outlet that blows cool air into a storage compartment (for example, the refrigerating compartment 2) in the kit component 512. FIG. 18 is a front view of the refrigerator in a state where the door is opened, which describes the embodiment of the present invention, and FIG. 19 and FIG. 20 are front views of the electrostatic atomizing apparatus 200 in a state of being attached the cover, which is installed in the refrigerator 1 describing the embodiment of the present invention.

In the kit component 512, at least one upper cool air outlet 533 or lower cool air outlet 534 is formed in the cooling plate insulating material 511 in the lateral direction or in the vertical direction of a cover 300 of the electrostatic atomizing apparatus 200. Furthermore, there may be one or plural side cool air outlets 531 and 532, upper cool air outlets 533 and lower cool air outlets 534, respectively.

As described above, since at least one cool air outlet (the side cool air outlets 531 and 532, the upper cool air outlet 533 and the lower cool air outlet 534) that cools a storage compartment (for example, the refrigerating compartment 2) is formed in the kit component 512, the cool air outlet that blows cool air for cooling inside of the storage compartment can be formed only by installing the kit component 512 wherein the electrostatic atomizing apparatus 200 is provided in the partition wall 51; therefore, it is unnecessary to separately form a cool air outlet in the partition wall 51 of the storage compartment, production of an inner case is simplified and the refrigerator 1 that is low in cost can be obtained.

In a case wherein a temperature control over the cooling air trunk 50 is influenced by a temperature control over the storage compartment (when the temperature control over the storage compartment is given higher priority) when the cooling air trunk for the electrostatic atomizing apparatus 200 is shared with the cooling air trunk for cooling the storage compartment, it is applicable to form a dedicated cooling air trunk for the electrostatic atomizing apparatus 200 in addition to the cooling air trunk 50 for the storage compartment. Since the dedicated cooling air trunk for the electrostatic atomizing apparatus 200 has only to cool the heat dissipating fin part 212, a flow volume of cool air can be small, and a cross-section area of the cooling air trunk is such as to provide an air volume sufficient for cooling the heat dissipating fin part 212 to a prescribed temperature (approximately the temperature where the heat absorbing fin part 211 does not freeze, and the temperature of the heat absorbing fin part 211 becomes lower than the temperature of the storage compartment, and moisture in the air inside the storage compartment can be condensed at the heat absorbing fin part 211) and can be approximately equal to or smaller than a half of that of the storage compartment cooling air trunk 50. Furthermore, when the temperature control over the heat dissipating fin part 212 in the cooling plate 210 provided inside the cooling air trunk is unnecessary, the damper device is also unnecessary; therefore, the electrostatic atomizing apparatus 200 and the refrigerator 1 that are low in cost and easy to control can be provided.

Now, the counter electrode 240 (a counter grounded electrode) formed of an electrically-conductive material (for example, a conductive resin or a conductive metal, etc. that is resistant to decay and the like) is installed in a place opposed to the discharge electrode 230 via a predetermined clearance (a predetermined clearance F in FIG. 8, which is set a clearance of approximately 1 to 10 mm, for example, so that a voltage can be efficiently applied), and a power supply 251 that energizes the discharge electrode 230 and the counter electrode 240 to generate nano-size mist is installed adjacent to (adjacent to the side surface or adjacent to the top or bottom of) the electrostatic atomizing apparatus 200 inside a high-voltage power supply part 250. In the counter electrode 240, a counter electrode opening part 241 (for example, a through hole) for spraying mist is formed in a position opposed to the protrusion part 231 (the tip section) in the discharge electrode 230. In the diagram, plural counter electrode opening parts 241b, 241c and 241d are formed in the counter electrode 240 at the positions opposed to the plural discharge electrodes 231b, 231c and 231d, respectively (see FIG. 6).

In the present embodiment, the discharge electrode 230 is formed into an approximately circular cylindrical shape made of foam metal with a three-dimensional net structure, such as titanium with pore diameters of approximately 10 to 800 µm (pore diameters of 50 to 300 µm preferably, and 50 to 150 µm, more preferably) and a voidage of approximately 60 to 90% (preferably 70 to 80%), and the protrusion part 231 has a shape (for example, an approximately conical shape that tapers gradually toward the counter electrode 240) in which the end tapers (becomes small) gradually or in a phased manner toward the counter electrode 240, wherein the amount of water absorption is large and capillary force is large, and which are shaped so that electricity can be efficiently applied to water as conductive material, and an electrical current can be easily discharged compared to a conventional ceramic porous material or a conventional metallic rod; therefore, water reaches sufficiently to the end of the protrusion part 231 in a short time, the length of time it takes until nano-size mist is generated can be shortened, and nano-size mist can be generated and sprayed instantly after a voltage is applied. Further, since the voltage can be efficiently applied, the amount of nano-size mist generated can be increased, which can sufficiently moisturize inside the storage compartment, a room, etc., and has an advantage that bacterial eradication and deodorizing can also be performed.

Furthermore, in the present embodiment, since the discharge electrode 230 and the heat absorbing fin part 211 of the cooling plate 210 is separated from each other, and the discharge electrode 230 and the heat absorbing fin part 211 of the cooling plate 210 are installed via the predetermined clearance Z, the degree of freedom of the shape and the location of the cooling plate 210 or the discharge electrode 230 is increased, the shapes and the locations of the discharge electrode 230, the counter electrode 240 and the cooling plate 210 can be freely set in accordance with a structure of each home electrical appliance, such as the refrigerator 1, an air conditioner, or an air purifier, and it is possible to obtain the electrostatic atomizing apparatus 200 that is compact in size and efficient in accordance with the home electrical appliance. Now, as for the clearance Z between the lower end surface 211Y of the heat absorbing fin part 211 and the top surface of the discharge electrode 230, since an electric current may be discharged between the lower end surface 211Y of the heat absorbing fin part 211 and the discharge electrode 230 when a voltage is applied between the discharge electrode 230 and the counter electrode 240 in a state wherein water droplets are attaching to the surface of the discharge electrode 230, it is necessary to ensure a clearance where an electric current is not discharged even in a state water droplets are attaching to the surface of the discharge electrode 230, and the predetermined clearance Z should be preferably equal to or larger than 4 mm. Further, even in a state water is accumulated over the discharge electrode 230, an electric current is not discharged between the discharge electrode 230 and the heat absorbing fin part 211, which is a water supply means, when 4 mm or larger predetermined clearance is ensured, hence there is no problem; however, since an electric current is less likely to be discharged when water is made not to accumulate over the discharge electrode 230, it is also acceptable to prevent water from accumulating. Further, it is also acceptable to configure the electrode holding part 220 so as not to accumulate water in a part for holding the discharge electrode 230 in the electrode holding part 220 by forming an opening or a notch, etc. so that water does not attach to or accumulate on the surface of the discharge electrode 230 opposed to the heat absorbing fin part 211, as the water supply means, (or it is also acceptable to configure the electrode holding part 220 to be able to discharge extra water from the part for holding the discharge electrode 230 in the electrode holding part 220 even when water is accumulated on the surface of the discharge electrode 230, and to form the water reservoir part for collecting discharged water in a lower part separately so that the water collected in the water reservoir part does not contact with the discharge electrode 230).

Further, it is possible to increase a degree of freedom of a setting range of an applied voltage and the predetermined clearance F (see FIG. 8), and to easily perform generation of nano-size mist with certainty. Furthermore, since the thinner the tip section on the counter electrode side of the protrusion part 231 is, the more stably a voltage can be applied, an electrical current can be stably discharged, and nano-size mist formed into a radical which is stable and whose particles are uniform in size can be continuously sprayed and generated. Here, in the present embodiment, the protrusion part 231 (an end shape) of the discharge electrode 230 is formed into an approximately conical shape, and the counter electrode 240 is formed into an approximately similar shape as the shape of the protrusion part 231 of the discharge electrode 230, having an approximately circular opening (perforated) shape (a counter electrode opening part 241) larger than a cross-sectional shape of the protrusion part 231 of the discharge electrode 230, in which case the predetermined clearance F (distance) is approximately 1 mm to 6 mm, and a voltage can be efficiently applied for generation of nano-size mist. The predetermined clearance F should be approximately 1 mm to 6 mm since a voltage cannot be efficiently applied and the amount of nano-size mist generated is reduced when the predetermined clearance F is too large or small.

Here, the discharge electrode 230 needs not be in an approximately columnar shape, and may be in a tabular shape or a recessed (depressed) shape. Since the discharge electrode 230 can efficiently receive dew condensation water dropping from the heat absorbing fin part 211 when at least only a portion to receive dew condensation water in the discharge electrode 230 is in a tabular shape or a recessed (depressed) shape, it is possible to supply nano-size mist stably using dew condensation water for production of nano-size mist without wasting the dew condensation water. Especially, when the portion that receives dew condensation water in the discharge electrode 230 is in a recessed (depressed) shape, the discharge electrode 230 itself can accumulate the dew condensation water, hence it is possible to resolve lack of dew condensation water, and further the electrode holding part 220 is unnecessary or can be reduced in size, and the electrostatic atomizing apparatus 200 and the refrigerator 1, which are low in cost, highly reliable, and simple in structure, can be provided. Further, in the present embodiment, when a state wherein water is not supplied to the protrusion part 231 by a foreign matter clogging in the discharge electrode 230 occurs, or when it is considered that water supply declines to a state wherein spraying mist cannot be performed, it may be applicable to provide a filter in the discharge electrode 230. Here, in the present embodiment, since foam metal with a three-dimensional net structure, such as titanium with pore diameters of approximately 10 to 800 μm (pore diameters of 50 to 300 μm preferably, and 50 to 150 μm more preferably) and a voidage of approximately 60 to 90% (preferably 70 to 80%) is used for the discharge electrode 230, capillary force and force of supplying water are large, and generally, dew condensation water dropping over the main body part 232 of the discharge electrode 230 does not accumulate in the main body part 232 of the discharge electrode 230 since water is sent to the tip section of the protrusion part 231 in a short time; however, the predetermined clearance Z is formed where an electrical current is not discharged between the discharge electrode 230 and the water supply means so that even if the dew condensation water accumulates in a surface in the tabular shape of the main body of the discharge electrode 230 or the recession shape formed in the main body part 232, an electrical current is not discharged between the discharge electrode 230 and the water supply means when a voltage is applied between the discharge electrode 230 and the counter electrode 240.

Additionally, by controlling an applied voltage in the power supply 251 of the high-voltage power supply part 250, the electrostatic atomizing apparatus 200 can control the generated amount of ozone or radical in mist; therefore, it is possible to reduce ozone or radical to a degree that ozone or radical does not affect the human body, prevent false effect of deterioration, etc. of resin components and so on constituting an inside wall of a storage compartment, and provide the refrigerator 1 that is hygienic, highly-reliable, and that does not affect the human body, which can spray nano-size mist that can offer sterilization and bacterial eradication effect.

The cover 300 is provided in the front surface of the electrostatic atomizing apparatus 200, which prevents a user from direct contact. The front surface cover 300 is attached so as to cover the cooling plate 210, the electrode holding part 220, the discharge electrode 230 and the counter electrode 240, etc., and one or plural openings (for example, a front surface opening part 515, a side surface opening (not shown in the diagrams), an upper surface opening (not shown in the diagrams), or a lower surface opening (not shown in the diagrams)) which are openings with approximate sizes that a user cannot insert a finger therein are formed in the front surface or the both side surfaces in the cover 300, and moisture that is made into nano-size mist is sprayed inside a storage compartment (for example, the refrigerating compartment 2, or may be any storage compartments) through one or plural openings that are formed in the cover 300. Now, by forming one or plural front surface openings with approximate sizes that a user cannot insert a finger therein in the front surface, the upper surface and the lower surface as well of the cover 300, it is possible to spray water droplets that are made into nano-size mist to a needed direction inside the storage compartment (for example, the refrigerating compartment 2) or any directions inside the storage compartment.

Since the electrostatic atomizing apparatus 200 is provided in, for example, a back of a rear side, a side surface or an upper surface of a storage compartment, and further, atomization is performed by applying a high voltage, fine mist that is made into nano-size mist can be sprayed, hence atomization can be performed from the vicinity of the rear (back) to the vicinity of the front surface as well of the refrigerator 1 by a flow of cool air for cooling inside the storage compartment, and further, since the electrostatic atomizing apparatus 200 is provided in an superior section, atomization can be performed from the upper part to the down part inside the storage compartment by the gravity or a flow of cool air for cooling inside the storage compartment, hence mist of nano-size particles can be sprayed in approximately entire area inside of the storage compartment. Further, by providing the electrostatic atomizing apparatus 200 in the back adjacent to the side surface of the superior section in the rear, broader usage of the inner volume of the storage compartment (for example, the refrigerating compartment 2) is made possible.

Since the sides of the back of the upper shelf in the storage compartment (for example, the refrigerating compartment 2) located in the superior section of the refrigerator 1 are considered as places which a user does not use much since the places are difficult for a user to reach, and to see and store a storage item therein, by providing the electrostatic atomizing apparatus 200 in the back of the sides of the superior section in the rear of the storage compartment, the back of the side surfaces in the superior section of the storage compartment, or the back of the upper surface in the superior section of the storage compartment, an ineffective volume (dead volume) unlikely to be used inside the storage compartment can be used effectively; therefore, bacterial eradication and humidification inside the storage compartment can be performed without reducing the inner volume, hence the refrigerator 1 that can keep cleanliness and freshness, and further with a large inner volume can be obtained.

Especially, when the refrigerator 1 is large-size and tall one equal to or larger than approximately 300 L (liter) with a total height of equal to or taller than approximately 165 cm, since the back in the superior section of the rear (especially the sides of the back in the superior section of the rear) in the storage compartment (for example, the refrigerating compartment 2) located in the uppermost part of the refrigerator 1 is difficult for a user (especially a housewife, a child, or an elderly person, etc. who is shorter than approximately 160 cm) to reach and use, and likely to become a void volume; therefore, by providing the electrostatic atomizing apparatus 200 in proximity to the back of the superior section in the upper shelf (for example, the back of the sides or the back of the center in the superior section in the upper shelf) of the storage compartment (for example, the refrigerating compartment 2) in the top shelf, the void volume (dead volume) unlikely to be used inside the storage compartment can be used effectively, bacterial eradication and humidification can be performed inside the storage compartment without reducing the inner volume, and cleanliness and freshness can be kept, hence the refrigerator 1 with a large inner volume wherein freshness is retained, and which is highly reliable and capable of improving the shelf life can be obtained.

Further, by placing the electrostatic atomizing apparatus 200 in the back near the center of the superior section in the rear inside the storage compartment, it is possible to spray mist of nano-size particles efficiently in the whole area inside the refrigerator (inside the storage compartment) only by installing one electrostatic atomizing apparatus 200. Especially, it is possible to spray mist into the refrigerator from the front surface, the lower surface, and the both sides by forming openings that can spray mist in the front surface, the lower surface and the both sides of the cover 300, etc., for example, in the electrostatic atomizing apparatus 200 so that mist of nano-size particles from the electrostatic atomizing apparatus 200 located near the approximate center can be sprayed from the both sides. Additionally, it is possible to spray mist also to the approximate center of the refrigerator by forming the front surface opening part 515 for spraying mist in the front surface (face), the upper surface and the lower surface of the cover 300 of the electrostatic atomizing apparatus 200. Thus, it is possible to provide the refrigerator 1 that can effectively perform bacterial eradication and humidification in the whole area inside of the storage compartment, wherein freshness is retained, and which is capable of improving the shelf life and low in cost can be obtained.

Now, when flammable or semi-flammable refrigerant (for example, hydrocarbon refrigerant (HC refrigerant), etc., and for example, isobutane, etc.) that is flammable and heavier than air is used for refrigerant to be used in a refrigerating cycle, only if the high-voltage power supply part 250, the discharge electrode 230 and the counter electrode 240 of the electrostatic atomizing apparatus 200 are placed in a superior section of a storage compartment (for example, the refrigerating compartment 2) located in the upper part (for example, the superior section of the storage compartment located in the uppermost portion of the refrigerator 1), even when the refrigerant is leaked, the leaked flammable refrigerant does not fill the refrigerator 1 to the electrostatic atomizing apparatus 200 placed in the superior section of the refrigerator 1 or it takes time for the leaked flammable refrigerant to fill the refrigerator 1 to the electrostatic atomizing apparatus 200 placed in the superior section of the refrigerator 1 since the leaked flammable refrigerant is heavier than air, and fills the refrigerator 1 from the lower part; therefore, the refrigerator 1 that is safe and highly reliable, having a low risk of failure occurrence due to ignition by leaked flammable refrigerant, can be obtained.

Further, by forming a recession inside the partition wall 51 (the rear wall or the side walls) in the rear or the sides of the storage compartment, and housing the electrostatic atomizing apparatus 200 inside the recession, the inner volume is increased, and the design is enhanced. In this case, since there often exists a limit to the thickness of the rear wall and the side walls of the storage compartment, there is a need to configure the walls to have thickness as thin as possible. Therefore, in the present embodiment, in order to make the size of the cooling plate 210 in the length direction as small as possible, the length in the depth direction (for example, the depth direction size 211L of the heat absorbing fin part 211 in FIG. 8) is reduced while the size in a vertical direction (the upper and lower length direction in FIG. 8) or a horizontal direction (for example, the width direction size 211K in FIG. 8) of at least one of the heat absorbing fin part 211 and the heat dissipating fin part 212 of the cooling plate 210 is increased.

That is, by making the length (for example, the depth direction size 211L of the heat absorbing fin part 211 in FIG. 8) in the front-back direction (length direction) of at least one of the heat absorbing fin part 211 and the heat dissipating fin part 212 in the cooling plate 210 smaller (thinner) than the length (for example, the size in the vertical length direction in FIG. 8, or the width size 211K in FIG. 9) in the vertical direction (length direction) or the horizontal direction (width direction), the size of the cooling plate 210 in the depth direction is made as small as possible. For example, in a case of the heat absorbing fin part 211, since the depth direction size of the cooling plate 210 can be made small by making the width direction size 211K large and the depth direction size 211L small, the depth direction size of the electrostatic atomizing apparatus 200 can be made small, and the electrostatic atomizing apparatus 200 that is compact and thin can be obtained. Similarly, by making the width direction size large and the depth direction size small also in the heat dissipating fin part 212, the depth direction size can be made small, and the electrostatic atomizing apparatus 200 that is small and thin can be obtained.

When (a part of) the cooling air trunk is provided in the partition wall 51 (heat insulating wall) in the rear surface or the side surfaces of the storage compartment in the refrigerator 1 (in a case wherein such as a recession that houses at least a part of (or whole) the electrostatic atomizing apparatus 200 is formed in the partition wall 51 and (a part of) the cooling air trunk is provided in the side of the recession), by placing at least a part of (or whole) the electrostatic atomizing apparatus 200 so as to be housed in the recession in the partition wall 51 that is placed lateral to the recession, locating the heat dissipating fin part 212 of the cooling plate 210 inside the cooling air trunk lateral to the recession, and locating the heat absorbing fin part 211 inside the recession or inside the storage compartment, it is only necessary to provide the cooling plate 210 of the electrostatic atomizing apparatus 200 in the cooling air trunk in the direction lateral to the recession wherein the electrostatic atomizing apparatus 200 is housed, and there is no need to provide the heat dissipating fin part 212 in a manner to penetrate the partition wall 51 in the rear of the storage compartment in the depth direction, hence assembly and installation, etc. can be easily performed. In this case, the heat conducting part 213 should be provided in a manner to penetrate a heat insulating partition between the recession and the cooling air trunk, and the heat absorbing fin part 211 and the heat dissipating fin part 212 should be installed so as not to line in the depth direction of the refrigerator 1, but to line in the width direction (right and left direction) of the refrigerator, in which case, the heat absorbing fin plate (the heat absorbing fin part 211), the heat dissipating fin plate (the heat dissipating fin part 212), and the heat conducting part 213 can be installed by making the lengths in the vertical direction (the flow direction of the cool air in the air trunk) long so as to increase the heat transmission area, and by making the lengths in the depth direction (for example, the width direction size 211K direction of the heat absorbing fin part 211) short.

The above is described for the case of applying the electrostatic atomizing apparatus 200 to the refrigerator 1, whereas the electrostatic atomizing apparatus 200 of the present invention can be applied not only to the refrigerator 1 but also to a home electrical appliance and an appliance, etc. such as an air conditioner, an air purifier, a humidifier, etc.

(Second Electrostatic Atomizing Apparatus)

Figure 12:
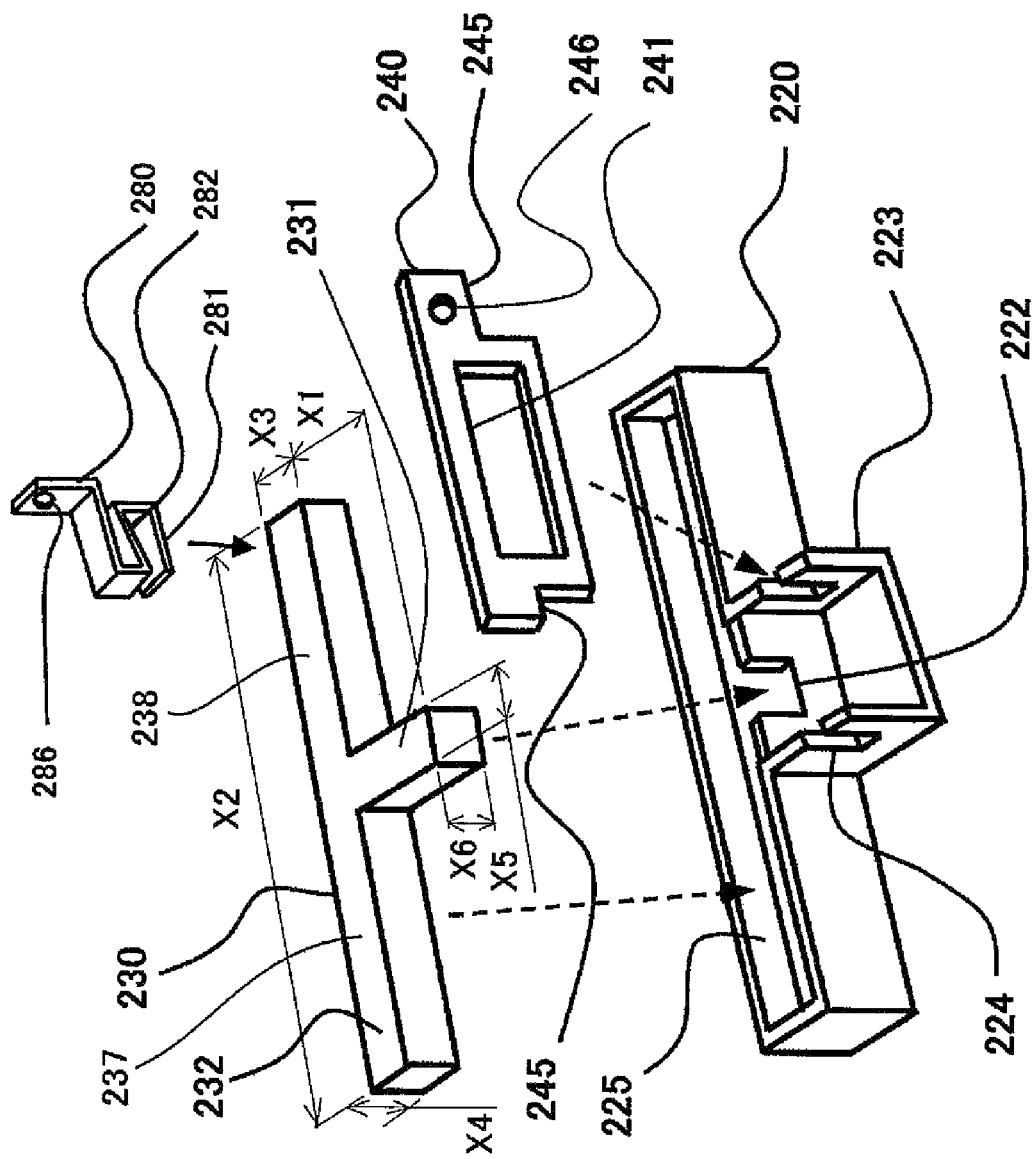
FIG. 12 is an exploded perspective view of an alternative electrostatic atomizing apparatus 200 describing the embodiment of the present invention.
Figure 13:
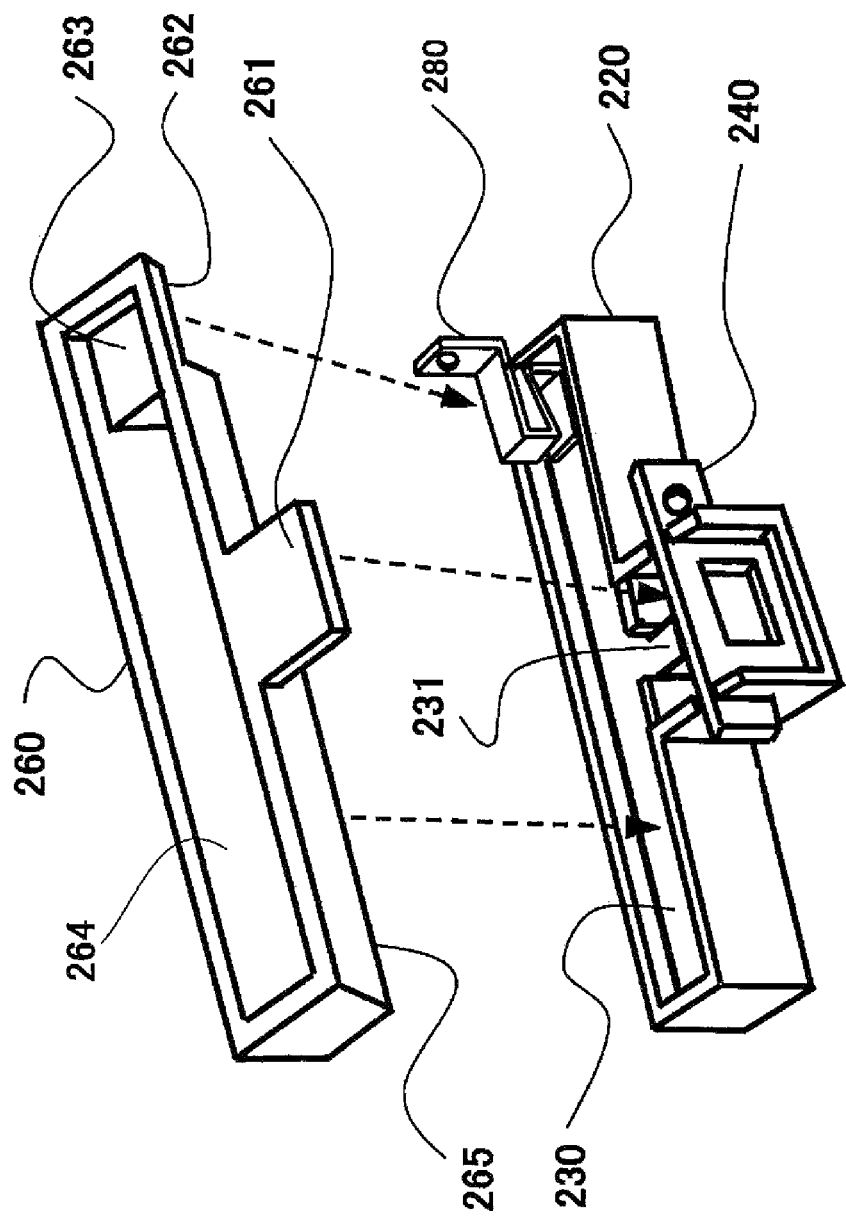
FIG. 13 is a perspective view illustrating an assembly method of the alternative electrostatic atomizing apparatus 200 describing the embodiment of the present invention.
Figure 14:
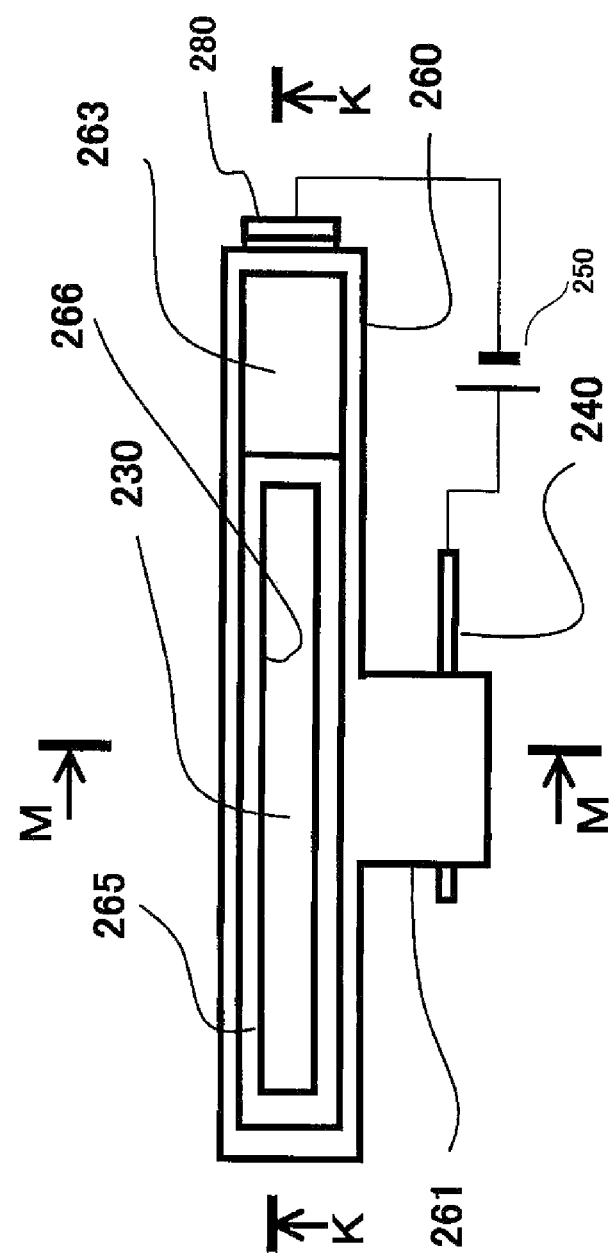
FIG. 14 is a top view of the alternative electrostatic atomizing apparatus 200 describing the embodiment of the present invention.
Figure 15:
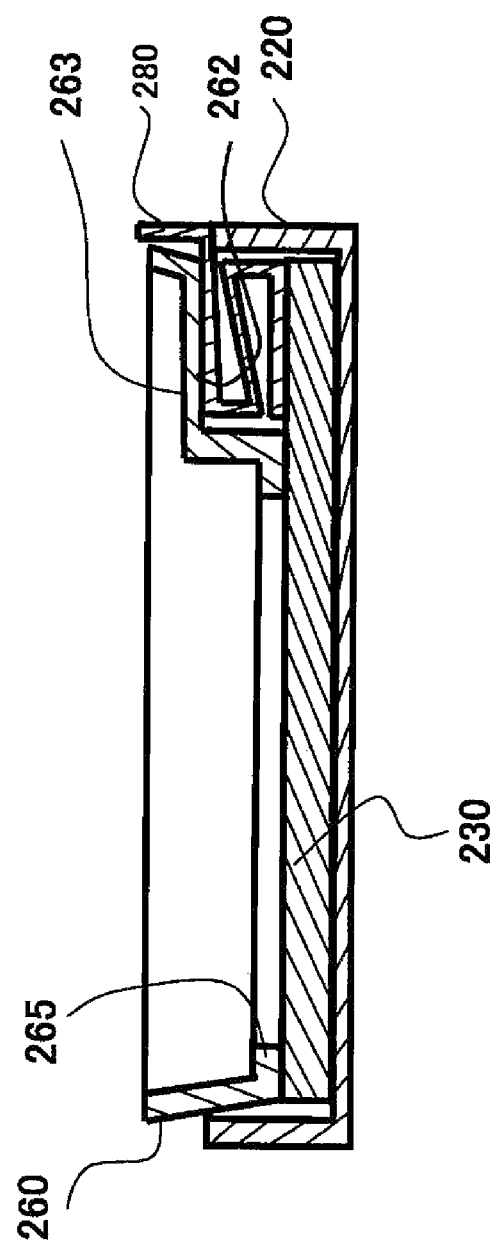
FIG. 15 is a sectional view of the electrostatic atomizing apparatus 200 which illustrates a cross-section K-K of the electrostatic atomizing apparatus 200 as shown in FIG. 14, describing the embodiment of the present invention.
Figure 16:
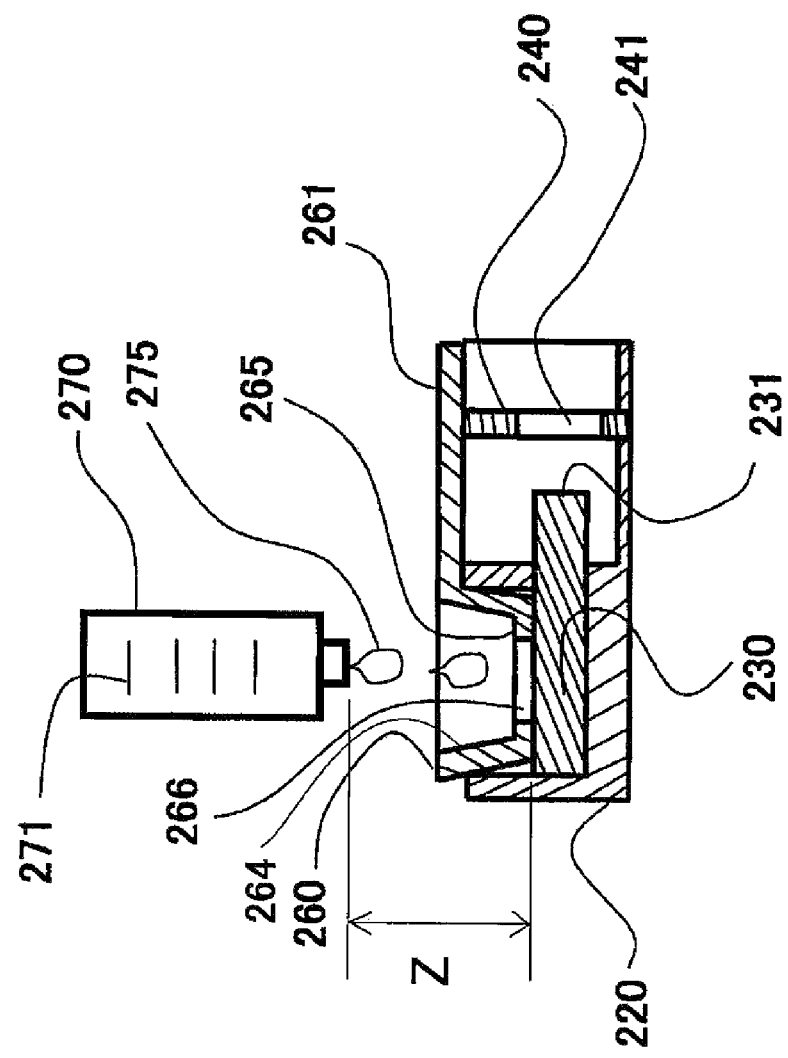
FIG. 16 is a sectional view of the electrostatic atomizing apparatus 200 which illustrates a cross-section M-M of the electrostatic atomizing apparatus 200 as shown in FIG. 14, describing the embodiment of the present invention.
Figure 17:
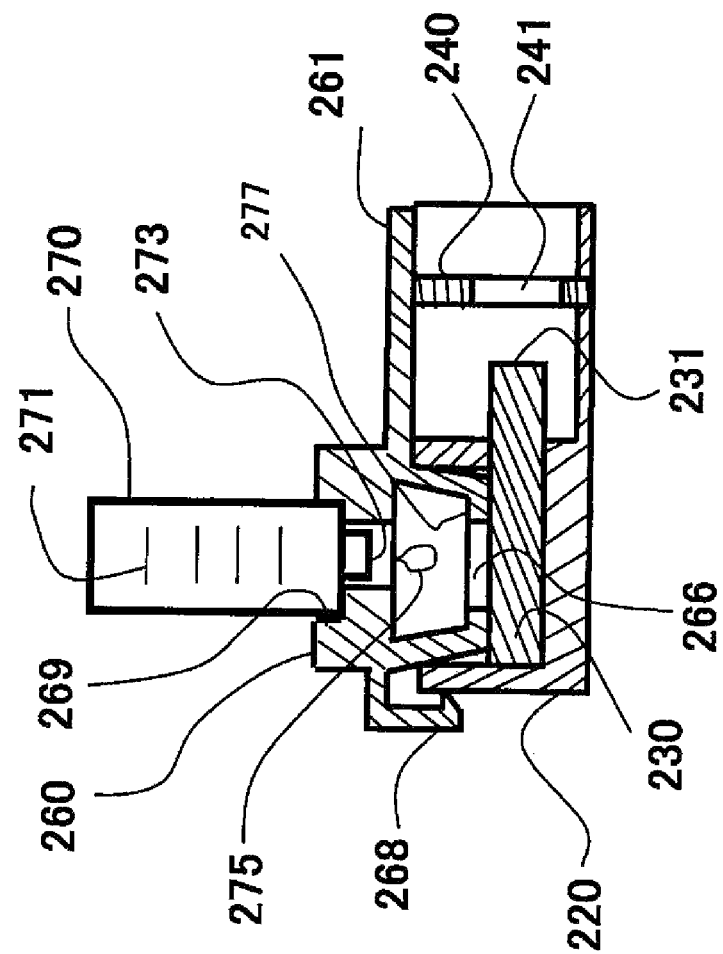
FIG. 17 is a diagram for describing a state where the feed-water means is provided in the electrostatic atomizing apparatus 200, describing the embodiment of the present invention.

Now, an alternative configuration example of the electrostatic atomizing apparatus 200 will be described. FIG. 12 is an exploded perspective view of an alternative electrostatic atomizing apparatus 200 describing the embodiment of the present invention, FIG. 13 is a perspective view illustrating an assembly method of the alternative electrostatic atomizing apparatus 200 describing the embodiment of the present invention, FIG. 14 is a top view of the alternative electrostatic atomizing apparatus 200 describing the embodiment of the present invention, FIG. 15 is a sectional view of the electrostatic atomizing apparatus 200 which illustrates a cross-section K-K of the electrostatic atomizing apparatus 200 as shown in FIG. 14, describing the embodiment of the present invention, FIG. 16 is a sectional view of the electrostatic atomizing apparatus 200 which illustrates a cross-section M-M of the electrostatic atomizing apparatus 200 as shown in FIG. 14, describing the embodiment of the present invention, and FIG. 17 is a diagram for describing a state where a feed-water means is provided in the electrostatic atomizing apparatus 200, describing the embodiment of the present invention. The same signs are assigned to the similar parts as in FIG. 1 through FIG. 11, whereof the explanations are omitted.

In the diagrams, the electrostatic atomizing apparatus 200 consists of the discharge electrode 230, the counter electrode 240 and the electrode holding part 220, and the discharge electrode 230 and the counter electrode 240 are housed and installed in the electrode holding part 220 so as to form a predetermined clearance (the clearance similar to the clearance F in FIG. 8). The discharge electrode 230 in an approximately T-shape is formed together by the main body part 232 in a parallelepiped (quadrangular prism) shape with an elongated shape in an axial direction of a cross-section surface of an approximately rectangle (or an approximately quadrangle), and the protrusion part 231 in a parallelepiped shape (or a pyramid shape) having a cross-section surface in an approximately rectangle (or an approximately quadrangle), which is provided from a middle of the main body part 232 in the axial direction in a manner to protrude at an approximately right angle with respect to the axial direction, and is formed of foam metal such as titanium. The main body part 232 of the discharge electrode 230 may be in a columnar shape in an elongated shape (a long shape in the axial direction) with an approximately circular cross-section, and the protrusion part 231 has only to be provided from the middle of the main body part 232 in the axial direction in a manner to protrude at the approximately right angle with respect to the axial direction, and may be in a columnar shape (or a conical shape) with a cross-section surface in an approximately circular shape (or an approximately circular shape). That is, the protrusion part 231 may be formed in a conical shape or a pyramid shape, which gets thinner toward the direction of the counter electrode 240. Additionally, one or plural protrusion parts 231 may be provided.

Here, as shown in FIG. 12, the main body part 232 of the discharge electrode 230 has a length in an axial direction of X2, a width of X3 and a thickness of X4. Further, the protrusion part 231 has a protrusion length of X1, a width of X5 and a thickness of X6. The length X2 of the main body part 232 is longer than the length X1 of the protrusion part 231, and the ratio of X2 divided by X1 (the ratio of X2 against X1) is preferable when the ratio is equal to or larger than 4 but equal to or smaller than 20 since it is readily processable, and further, an amount of water supply from the main body part 232 to the protrusion part 231 is large, and a time for water supply can be shortened (desirably, the ratio of X2 against X1 should be equal to or larger than 6 and equal to or smaller than 15 since it is well balanced in consideration of processing efficiency, intensity, the amount of water supply, and the time for water supply. If the ratio is too large, the intensity gets too low). Further, it is preferable that the thickness X4 of the main body part 232 and X6 of the protrusion part 231 are within a range of approximately 1.5 to 4 mm since water can be supplied to the protrusion part 231 in a short time by capillary action due to better processing efficiency, a high water absorption rate and better moisture-retaining property. For the above reasons, in the present embodiment, it is approximately set that X1 is 3 to 7 mm, X2 is 30 to 80 mm, X3 is 4 to 7 mm, X4 is 1.5 to 4 mm, X5 is 3 to 7 mm, and X6 is 1.5 to 4 mm. The discharge electrode 230 in the approximately T-shape can be produced by cutting seated foam metal such as titanium, etc. with a thickness of approximately 1.5 to 4 mm by a press working or a laser processing, etc.

As shown above, the discharge electrode 230 is formed of foam metal having a three-dimensional net structure, consisting of the main body part 232 in the approximately parallelepiped shape or the approximately columnar shape which is elongated in the axial direction, and the protrusion part 231 in the approximately parallelepiped shape or the approximately conical shape which protrudes from the middle of the main body part 232 in the axial direction toward the approximately right angle to the axial direction of the main body part 232, and which is shorter than the length of the main body part 232 in the axial direction, and is integrally formed with the main body part 232, whereto water attaching to the surface of the main body part 232 is supplied by capillary action. Thus, it is possible to increase the surface area of the main body part 232, and much water can be supplied to the protrusion part 231 by capillary action from water attaching to the surface of the main body part 232.

Further, when water is supplied by capillary action from the main body part 232 to the tip section of the protrusion part 231 in the opposite direction to the counter electrode 240, since the protrusion part 231 is provided from the middle in the axial direction (an approximate center in the axial direction) of the main body part 232, the main body part is divided into two (for example, the first main body part 237 and the second main body part 238) with respect to a protrusion position of the protrusion part 231, water can be supplied by capillary action to the protrusion part 231 from two parts (both sides of the protrusion part 231) of the first main body part 237 and the second main body part 238; therefore, it is possible to supply much water to the protrusion part 231, increase the amount of spraying mist, and spray mist stably. Furthermore, even when either (for example, the first main body part 237) of the first main body part 237 or the second main body part 238 does not function due to clogging and so on, the other part (the other) (for example, the second main body part 238) can supply water to the protrusion part 231, hence it is possible to supply water stably to the protrusion part 231 over long periods, and to obtain the electrostatic atomizing apparatus 200 (the mist spraying apparatus) which is capable of stably spraying mist over long periods and highly reliable.

Further, the electrostatic atomizing apparatus 200 includes a fixing means 260 (a pressing means) whereby the discharge electrode 230 or the counter electrode 240 that is housed in the electrode holding part 220 is secured to and held by the electrode holding part 220, and at least the electrode holding part 220, the discharge electrode 230, the counter electrode 240 and the fixing means 260 are integrally formed to be a kit component, which is installed in a wall surface (for example, the side walls, the rear wall or the partition wall 51, etc.) of a storage compartment in the case of the refrigerator 1. Further, in an appliance such as an air conditioner, since the electrostatic atomizing apparatus 200 is provided inside a chassis (on a downstream side, etc. of a filter with respect to air flow) of an indoor unit, etc. installed inside a room, easy and compact assembly of the electrostatic atomizing apparatus 200 (the kit component) is achieved, and easy installation of the electrostatic atomizing apparatus 200 (the kit component) to the wall surface or the chassis is possible.

Now, in the present embodiment, the discharge electrode 230 (for example, both of the main body part 232 and the protrusion part 231, or only the main body part 232) is formed of foam metal having a three-dimensional net structure, including the main body part 232 in the approximately parallelepiped shape or the approximately columnar shape which is elongated in the axial direction, and the protrusion part 231 in the approximately parallelepiped shape, the approximately columnar shape, the approximately pyramid shape or the approximately conical shape which protrudes from the middle of the main body part 232 in the axial direction toward the approximately right angle to the axial direction, and which is shorter than the length of the main body part 232 in the axial direction, and is integrally formed with the main body part 232, whereto water attaching to the surface of the main body part 232 is supplied by capillary action through the inside of the main body part 232, wherein the axial direction length X2 of the main body part 232 is within the range of equal to or larger than 4 but equal to or smaller than 20 times the length X1 of the protrusion part. When the axial direction length X2 of the main body part 232 is too long with respect to the length X1 of the protrusion part, the main body part 232 becomes too narrow and poorly balanced, the processing accuracy of which is worsened, and further, can be damaged during processing or at the time of assembly, etc.; therefore, it is recognized that the axial direction length X2 of the main body part 232 should preferably be equal to or smaller than approximate 20 times (desirably equal to or smaller than approximate 15 times) the length X1 of the protrusion part. Additionally, when the axial direction length X2 of the main body part 232 is too short with respect to the length X1 of the protrusion part, the amount of water supplied from the main body part 232 is too small, or the time it takes for water to be supplied to the tip section of the protrusion part is too long, and it takes too much time to spray mist; therefore, the axial direction length X2 of the main body part 232 is preferably be approximately equal to or larger than 4 times the length X1 of the protrusion part.

It is better when the main body part 232 is in a parallelepiped shape since a mounting surface on the electrode holding part 220 is level and the position is settled at the time of installation, and further, it is better when the axial direction length X2 of the main body part 232 is sufficiently greater than the protrusion length X1 of the protrusion part 231. Since it is preferable that the main body part 232 receives water dropping from the straight above feed-water means by the upper surface efficiently and supplies water attaching to the upper surface through the inner part by capillary action to the tip section of the protrusion part 231 as much as possible, it is preferable to increase the axial direction length so as to increase the upper surface area as much as possible, hence the width X3 is made greater than the thickness X4 so that the upper surface area is large. Further, since it is preferable that the protrusion part 231 supplies water to the tip section opposed to the counter electrode in a time as short as possible, the shorter the protrusion part 231 is, the better, and it is preferable that the protrusion part 231 is equal to or smaller than approximately 7 mm. Additionally, when the protrusion part 231 is too short, a voltage may be applied to between the main body part 232 and the counter electrode 240, and the processing becomes difficult, hence it is recognized that the protrusion part 231 should preferably be approximately equal to or smaller than 7 mm.

Further, the tip section of the protrusion part 231 should preferably narrow and sharpen toward the counter electrode 240 since ozone at a level that does not affect a human body can be generated by applying a voltage to the tip section even in a state without water (non-water supply state), and bacterial eradication and deodorizing effect can be obtained, and should preferably be in a pyramid shape or a conical shape. Now, when the protrusion part is formed in a pyramid shape or a conical shape, and the tip section of the protrusion part 231 is in a shape that narrows and sharpens toward the counter electrode 240, by applying a voltage to between the discharge electrode 230 and the counter electrode 240 all the time during operation of an appliance irrespective of with or without water in the tip section of the protrusion part 231, the refrigerator 1 or a home electrical appliance such as an air conditioner that can perform deodorizing and bacterial eradication can be obtained since mist or ozone can be sprayed even in a case of lack of water supplied from the feed-water means.

In the present embodiment, in a case wherein the sizes (widths or thicknesses, etc.) or the cross-section areas of the external shapes of the main body part 232 and the protrusion part 231 are approximately the same, when the axial direction length of the main body part 232 is within the range of equal to or larger than 4 but equal to or smaller than 20 times the length of the protrusion part 231, the processing efficiency is better, an amount of water supply from the main body part 232 to the protrusion part 231 is great, and time for water supply can be shortened. Now, in a case of 21 times, which is larger than 20 times, the main body part 232 is too long in the axial direction, hence the main body part 232 can be damaged during processing or damaged at the time of assembly, and has poor reliability. In addition, when it is 3.5 times, which is smaller than 4 times, since the upper surface area of the main body part 232 in the discharge electrode 230 is small, the amount of water supply to the protrusion part 231 is small and a case wherein water lacks occurs, and mist cannot be stably sprayed; therefore, the axial direction length of the main body part 232 should preferably be equal to or larger than 4 times but equal to or smaller than 20 times the length of the protrusion part 231. Desirably, it is preferable when it is within the range of equal to or larger than 6 times but equal to or smaller than 15 times, since intensity of the discharge electrode 230 can be obtained, and much water can be supplied to the protrusion part 231 in a short time, water can be stably supplied to the protrusion part 231, and a sprayed amount of nano-size mist can be increased in a case of applying a voltage to the discharge electrode 230 and the counter electrode 240.

In the present embodiment, since foam metal such as titanium, etc. is used for the discharge electrode 230, which is a metallic porous body having a three-dimensional net structure like a sponge, the amount of water absorption inside the metal is approximately 2 to 5 times larger than that of what is not foam metal, capillary force is larger than that in sintered metal, electrical resistance is approximately $(0.4 \text{ to } 2) \times 10^{-7}$ $\Omega \cdot m$ and small so that electricity can be efficiently applied to water as a conductive material; therefore, the foam metal can conduct electricity far more readily than a ceramic with large electrical resistance (the electrical resistance is approximately $10^{12}$ $\Omega \cdot m$ and large), etc., and can generate a large amount of mist, wherein setting, etc. of an applied voltage is easy and the applied voltage can be made small, and it is possible to generate nano-size mist surely and easily. A material with electrical resistance of approximately $10^{-8}$ to $10^{-4}$ Ω·m can readily conduct electricity, can generate a large amount of mist, and can perform generation of nano-size mist stably. Further, since the electrical resistance is small and electricity can be readily conducted, a low-power electrostatic atomizing apparatus whereto a high voltage can be readily applied can be obtained.

Here, in the present embodiment, the foam metal such as titanium with pore diameters of between 10 and 800 μm, and a voidage of between 60 and 90%, etc. is used for the discharge electrode 230. The foam metal has dramatically larger clogging resistance against foreign matter than a ceramic, etc. with small pore diameters of 0.1 to 3 μm, which is not foam metal, hence water can be stably supplied to the protrusion part 231 from the main body part 232 over long periods of time. Since the risk that clogging occurs is increased when the pore diameters are smaller than 10 μm, the pore diameters should preferably be equal to or larger than 10 μm. Further, since water droplets get large and an amount of generated nano-size mist is reduced when the pore diameters are too much larger than 800 μm, the pore diameters should preferably be equal to or smaller than 800 μm. In addition, since the larger the voidage (porosity) is, the more water it can retain inside, it is preferable that the voidage is large in a case of using in the electrostatic atomizing apparatus 200. Since the foam metal of metallic porous body with a three-dimensional net structure such as titanium with a high voidage of between approximately 60 and 90%, etc. is used in the present embodiment, different from a conventional ceramic or sintered metal, etc. with a voidage of equal to or smaller than 50%, more water can be retained inside the foam metal compared to the conventional ceramic or sintered metal, etc. Thus, a large amount of nano-size mist can be generated efficiently.

It is better that the foam metal used for the discharge electrode 230 has large capillary force, less variation in the pore diameters and stable, and further has high clogging resistance, and preferably, foam metal with pore diameters of between approximately 50 and 300 μm, and a voidage of higher than 70% but equal or lower than 80% is desirable. Further, since stiffness and intensity of the discharge electrode 230 increase by using foam metal of titanium for the discharge electrode 230, electrical wear, etc. due to application of a voltage can be reduced, attrition resistance against fine vibration during operation of the refrigerator 1 or an air conditioner can be increased, a long period of use is made possible, and reliability is enhanced. Furthermore, by using titanium for the discharge electrode 230, the amount of generated ozone by corona discharge at the time of voltage application can be reduced by resolving the ozone by reduction action; therefore, adverse effect on a human body due to too large amount of generated ozone can be reduced in comparison with a case of using a ceramic material for an electrode, and the electrostatic atomizing apparatus 200 that is safety and capable of generating an appropriate amount of ozone can be provided. Additionally, in a case of using titanium as foam metal for the discharge electrode 230, by performing oxidation treatment, hydrophilia is increased, water on the surface of the main body part 232 can be readily absorbed by capillary action, and water can be stably supplied to the protrusion part 231, which makes it possible to spray nano-size mist stably for a long period of time.

The counter electrode 240 is placed with the predetermined clearance F from the tip section of the protrusion part 231 of the discharge electrode 230 (similarly as in FIG. 8), and the counter electrode opening part 241 as an approximately quadrangular through hole is formed in the position opposed to the tip section of the protrusion part 231 in the discharge electrode 230. Now, the cross-section shape of the tip section of the protrusion part 231 in the discharge electrode 230 is in an approximately quadrangular shape, and the counter electrode opening part 241 in the counter electrode 230 is an opening in an approximately quadrangular shape larger than the approximately quadrangular shape of the tip section of the protrusion part 231 in the discharge electrode 230. The cross-sectional shape of the tip section of the protrusion part 231 in the discharge electrode 230 may be in an approximately circular shape, and the opening shape of the counter electrode opening part 241 in the counter electrode 240 may be in an approximately the similar shape as the cross-sectional shape (or an outside diameter shape) of the tip section of the protrusion part 231 in the discharge electrode 230, in which case the opening shape may be an opening in a shape larger than the cross-sectional shape (or the outside diameter shape) of the tip section of the protrusion part 231 in the discharge electrode 230; or the opening shape of the counter electrode opening part 241 in the counter electrode 240 may be different from the cross-sectional shape (or the outside diameter shape) of the tip section of the protrusion part 231 in the discharge electrode 230, in which case the tip section of the protrusion part 231 in the discharge electrode 230 may be in a pyramid shape (the cross-sectional shape (or the outside diameter shape) is the approximately quadrangle), and the opening shape of the counter electrode opening part 241 in the counter electrode 240 may be an opening in a circular shape larger than the cross-sectional shape of the protrusion part.

The electrode holding part 220 consists of the electrode housing part 225 that houses, holds and secures the main body part 232 of the discharge electrode 230, and a counter electrode housing part 223 provided so as to protrude from a middle (an approximate center) of the electrode housing part 225 in the axial direction (longitudinal direction) and that houses and holds the counter electrode 240. The discharge electrode 230 is provided so that the protrusion part 231 protruding from the main body part 232 in the discharge electrode 230 housed in the electrode housing part 225 protrudes into the counter electrode housing part 223 via a notch part 222 such as an opening hole or a notch formed in a partition wall between the electrode housing part 225 and the counter electrode housing part 223. Now, if the cooling plate 210 is the feed-water means, there is a possibility that an electrical current is discharged between the heat absorbing fin part 211 and the main body part 232 of the discharge electrode 230 when the main body part 232 is held in a state water droplets are attached to the upper surface of the main body part 232 in the discharge electrode 230; therefore, in this case, it is necessary to form an opening or a notch, etc. (not shown in the diagrams) in a bottom surface or side surfaces in the electrode holding part 220 to prevent water supplied from the feed-water means from accumulating inside the electrode holding part 220.

That is, by forming a notch or an opening in the electrode holding part 220 or the fixing means 260 (the pressing means or the pressing member), and preventing dew condensation water dropping from the heat absorbing part (the heat absorbing fin part 211) from accumulating in the electrode holding part 220 or the main body part 232 of the discharge electrode 230 in the state the main body part 232 of the discharge electrode 230 is held by the electrode holding part 220, even when a voltage is applied to between the discharge electrode 230 and the counter electrode 240, it is possible to prevent water from accumulating in the main body part 232 in the discharge electrode 230 held by the electrode holding part 220, and prevent an electrical current from being discharged from the discharge electrode 230 to the heat absorbing part (the heat absorbing fin part 211) in the cooling plate 210.

Here, as for the clearance Z between the lower end surface 211Y of the heat absorbing fin part 211, which is the water supply means, and the discharge electrode 230 (the upper surface of the main body part 232), there is a possibility that an electrical current is discharged between the lower end surface 211Y of the heat absorbing fin part 211 and the discharge electrode 230 in a case wherein a voltage is applied to between the discharge electrode 230 and the counter electrode 240 if water droplets are in a state of being attached to the surface of the discharge electrode 230; therefore, it is necessary to maintain a clearance wherein electric discharge does not occur, and the predetermined clearance Z should preferably be equal to or larger than 4 mm.

Further, the counter electrode holding part 224 such as a notch, a concave portion, etc. that holds a step portion 245 of the counter electrode 240 is formed in the counter electrode housing part 225. Additionally, a counter electrode conducting part 246 consisting of a hole and so on whereto a power wire or a wire lead is connected to apply current is formed in the counter electrode 240, and the counter electrode conducting part 246 is connected to the high-voltage power supply part 250 (FIG. 11, etc.) by a power wire or a wire lead, etc.

In the discharge electrode 230, the main body part 232 is pressed against and secured to the electrode housing part 225 by the fixing means 260 (the pressing means) via a conducting member 280 in a state where the main body part 232 is housed in and held by the electrode housing part 225, and the protrusion part 231 is housed in the counter electrode housing part 223. In the conducting member 280 (an electrode conducting means), the pressing part 281 that contacts with and presses the main body part 232, a spring part 282 that is elastically deformed and presses the pressing part 281 against the main body part 232 when it is pressed by the fixing means 260 (the pressing means, or the pressing member), an electrode conducting means conducting part 286 consisting of a hole, whereto a power wire or a wire lead is connected with the high-voltage power supply part 250 to apply an electrical current, and so on, are provided. The electrode conducting means conducting part 286 applies an electrical current to the discharge electrode 230 by the high-voltage power supply part 250 via the power wire or the wire lead, etc. Here, the conducting member 280 needs not be configured so as to be pressed and held by the fixing means 260 (the pressing means), and it is acceptable that the conducting member 280 has a spring property and is in such a shape that a voltage can be applied to the discharge electrode 230 by interleaving the main body part 232 by a spring force from a side (in a width direction).

The fixing means 260 (the pressing means, or the pressing member) is in a container shape, consisting of an opening portion 266 (see FIG. 14) formed in a bottom surface (or a side surface), an electrode pressing portion 265 formed in the bottom surface (or a side surface) that presses the discharge electrode 230 against the side of the electrode holding part 220 from above and holds the discharge electrode 230, or that prevents the discharge electrode 230 from moving upward, a slant part 264 (see FIG. 13) that slants toward a center direction from the outside so as to receive water supplied from the water supply means provided above (directly above) and supply water to the main body part 232 of the discharge electrode 230 efficiently, a conducting member pressing part 262 (see FIG. 13) formed in the bottom surface (or the side surface) that presses to the side of the electrode holding part 220 and secures the main body part 232 of the discharge electrode 230 housed in the electrode housing part 225 of the electrode holding part 220 via the conducting member 280 formed of elastic body, and a counter electrode cover part 261 that is provided so as to protrude toward approximately the same direction as the direction of the protrusion part 231 in the discharge electrode 230 from vicinity of an approximate center in an axial direction of a side wall of the fixing means 260 (the pressing means), which covers from above at least the part of the opening part 241 of the counter electrode 240 (the step portion 245 of the counter electrode 240 is inserted and housed in the notch 224 of the counter electrode housing part 223 in the electrode holding part 220) housed in the counter electrode housing part 223 of the electrode holding part 220, and prevents dust or foreign particles, etc. from attaching to the opening part 241 of the counter electrode 240. Here, the conducting member pressing part 262 is in a step shape which is concave by an approximately equivalent thickness as the thickness of the conducting member 280 with respect to the electrode pressing portion 265, and at least a part of the conducting member 280 is housed in the electrode pressing portion 265 in a state the discharge electrode 230 is pressed by the fixing means 260 (the pressing means) via the conducting member 280 (it is desirable that the almost entire conducting member 265 except the electrode conducting means conducting part 286 is housed).

Thus, the discharge electrode 230 and the counter electrode 240 are pressed against and secured to the electrode holding part 220 by the fixing means 260 (the pressing member) via the conducting member 280. In a state the discharge electrode 230 and the counter electrode 240 are secured to the electrode holding part 220, the predetermined clearance F is provided between the tip section with an approximately quadrangular surface of the protrusion part 231 in the discharge electrode 230 and the opening part 241 of the counter electrode 240. The predetermined clearance F is set within the range of between 1 mm and 8 mm so that high output is achieved when an electrical current is conducted and that a large amount of nano-size mist can be discharged.

The conducting member pressing part 262 has a step with a thickness (the thickness that is a thickness of shrinkage due to elastic deformation being subtracted from the thickness) that can maintain elastic force when the conducting member 280 is pressed with respect to the discharge electrode pressing portion 265 formed in the bottom surface of the fixing means 260 (the pressing means, or the pressing member), and by housing the conducting member 280 in the step portion and pressing the conducting member 280 from above by the discharge electrode pressing portion 265, the main body part 232 of the discharge electrode 230 is pressed to the electrode holding part 220 and secured by elastic force of the conducting member 280.

Further, a step part 263 (a raised step portion) wherein a part is concave so as to house the conducting member 280 is formed in a surface on the opposite side (a surface on the upper opening side of the fixing means 260) of the conducting member pressing part 262, at which part the cooling plate 210 is positioned, and which also doubles as a positioning part so as to keep a clearance (a distance between the discharge electrode 230 and the lower end surface 211Y of the heat absorbing fin part 211 in the cooling plate 210 (for example, a distance (the predetermined clearance Z) between the lower end surface 211Y of the heat absorbing fin part 211 and the discharge electrode 230 as shown in FIG. 9)) between the lower end surface 211Y of the heat absorbing fin part 211 and the main body part 232 of the discharge electrode 230, and which can be set to obtain a required predetermined clearance.

The fixing means 260 (the pressing means) secures the side wall, etc. of the electrode holding part 220 in a state wherein the discharge electrode 230 is housed in and held by the electrode housing part 225 of the electrode holding part 220, and in a state wherein the discharge electrode 230 is pressed against the electrode holding part 220 via the conducting member 280 from the upper surface opening side of the electrode holding part 220. Also in this case, the clearance Z between the lower end surface of the water supply means (for example, the lower end surface 211Y of the heat absorbing fin part 211) and the discharge electrode 230 (the upper surface) should preferably be small so as to limit dropping velocity of water dropping from the water supply means (for example, the heat absorbing fin part 211) to the discharge electrode 230 or the electrode holding part 220 directly below via a space, cushion an impact at the time of dropping to the discharge electrode 230 or the electrode holding part 220 and prevent splashing and flying out of the container and so on, and preferably be approximately 1 to 30 mm; however, when in a state in which water droplets are attaching to the surface of the discharge electrode 230, when a voltage is applied to between the discharge electrode 230 and the counter electrode 240, there is a possibility that an electrical current may be discharged between the lower end surface 211Y of the heat absorbing fin part 211 and the discharge electrode 230; therefore, the predetermined clearance Z between the water supply means (for example, the lower end surface 211Y of the heat absorbing fin part 211) and the discharge electrode 230 should preferably be equal to or larger than 4 mm where electrical discharge does not occur.

(Water Storage Tank Structure)

Further, as shown in FIG. 16 and FIG. 17, instead of providing the cooling plate 210, it is also applicable to configure a feed-water means such as a water storage tank 270 to be detachably held by the fixing means 260 (the pressing means). Graduation marks 271 are provided in the water storage tank 270, and since the water storage tank 270 is installed in such a manner that a user can see the graduation marks 271 in the state the water storage tank 270 is installed in the refrigerator 1, it is possible to confirm visually a time to refill water to be supplied to the discharge electrode 230. In this case, by setting a required distance (a predetermined clearance) between a water discharge spout 277 (a feed opening to feed water inside the water storage tank 270 to the discharge electrode 230) and the discharge electrode 230 approximately equivalent to the distance (the required predetermined clearance Z) between the discharge electrode 230 and the lower end surface of the heat absorbing fin part 211 in the cooling plate 210, the equivalent effect can be obtained.

As shown in FIG. 17, in a case of using the water storage tank 270 instead of the cooling plate 210, by forming a feed-water means cover part 269 in the fixing means 260 (the pressing means) and by performing positioning, holding and fixing of the water storage tank 270, the electrostatic atomizing apparatus 200 simple in structure and low in cost can be obtained. Further, since a water droplet 275 dropping from the water storage tank 270 is covered so as to be in an approximate closed state or at least a part of the water droplet 275 is covered by the feed-water means cover part 269 of the fixing means 260 (the pressing means), the water droplet 275 dropping inside the electrode housing part 225 of the electrode holding part 220 is insusceptible to foreign matter such as dust, molds, etc. in the surrounding air wherein the electrode holding part 220 and the fixing means 260 (the pressing means) are installed, hence it is possible to obtain the electrostatic atomizing apparatus 200 wherein a water droplet inside the electrode holding part 220 is less likely to get dirty, and is clean and hygienic. Furthermore, since the water droplet 275 dropping from the water discharge spout 277 of the water storage tank 270 is covered so as to be in an approximate closed state or at least a part of the water droplet 275 is covered by the feed-water means cover part 269 of the fixing means 260 (the pressing means), the water droplet 275 dropping inside the electrode housing part 225 of the electrode holding part 220 is insusceptible to the surrounding (influence of air flow or temperature, etc.) wherein the electrode holding part 220 and the fixing means 260 (the pressing means) are installed, hence it is unlikely that the water droplet 275 spatters somewhere due to air or a flow of cool air, etc., or water inside the water storage tank 270 or the water droplet 275 freezes, and the electrostatic atomizing apparatus 200 that is highly reliable can be obtained.

That is, according to the present embodiment, in the electrostatic atomizing apparatus 200, since the feed-water means cover pat 269 is provided to the fixing means 260 that covers at least a part of a pathway of dropping water between a feed-water means and the electrode holding part 220 so that water fed by dropping from the feed-water means (the cooling plate 210 or the water storage tank 270, etc.) formed directly above the discharge electrode 230 or the electrode holding part 220 to the discharge electrode 230 or the electrode holding part 220 is not directly influenced by the air or flow surrounding the dropping water, the water droplet 275 that is dropping is insusceptible to foreign matter such as dust, molds, etc. in the surrounding air wherein the electrode holding part 220 and the fixing means 260 (the pressing means) are installed, a water droplet attaching to the discharge electrode 230 or a water droplet inside the electrode holding part 220 is less likely to get dirty, clogging in the discharge electrode 230 can be prevented, and the electrostatic atomizing apparatus 200 that is highly reliable, clean and hygienic can be obtained.

Now, in a case of using a water storage tank 270 (the feed-water means) made of resin, which is not electrically conductive, for the water supply means, an electrical current is not discharged from the discharge electrode 230 to the water storage tank 270 even when water is in a state of attaching to the upper surface of the main body part 232 of the discharge electrode 230, in comparison to a case of using the cooling plate 210 for the feed-water means; therefore, it is also applicable to configure the electrode holding part 220 in a container shape to accumulate water. In this way, it is possible to maintain a state that water is constantly accumulated in the main body part 232 of the discharge electrode 230, and stably supply water to the protrusion part 231, hence mist can be stably sprayed. Further, also in a case of installing the cooling plate 210 in the fixing means 260 (the pressing means), by configuring the water droplet 275 (dew condensation water) dropping from the heat absorbing fin part 211 to be covered in an approximate closed state by the fixing means 260 (the pressing means), etc., the equivalent effect can be obtained.

Additionally, as shown in FIG. 17, by forming a fixing nail part 268 that protrudes toward the outside direction in the fixing means 260 from the side wall, and forming at least one fixing depression such as a depression, a notch, etc. in the side wall of the electrode holding part 220 in a position opposed to the fixing nail part 268 so as to form a fitting structure wherein the fixing nail part 268 of the fixing means 260 (the pressing means) is fit into or caught in the fixing depression formed in the side wall of the electrode holding part 20 by pressing the fixing means 260 in the direction of the electrode holding part 220, it is possible to integrally secure and hold the fixing means 260, the conducting member 280, the discharge electrode 230, the counter electrode 240, and the electrode holding part 220 by a simple operation, which can be made into a kit component, only by lightly pressing the fixing means 260

(the pressing means) to the side of the electrode holding part 220, and attachment or incorporation of the kit component to a home electrical appliance such as the refrigerator 1, an air conditioner, etc. or an appliance can be performed easily.

According to the present embodiment, since the distance between the water discharge spout 277 (the feed opening that feeds water inside the water storage tank 270 to the discharge electrode 230) of the water storage tank 270 (the feed-water means) and the discharge electrode 230 is set to have the predetermined clearance Z in a range wherein it does not occur that water dropping from the water discharge spout 277 is not fed to the discharge electrode 230 or into the electrode holding part 220 due to influence of the surrounding air or a flow of cool air, a feed-water means or a water passage that conveys water supplied from the feed-water means is unnecessary compared to a case wherein the feed-water means (for example, the water storage tank 270, etc.) is installed in a separate place distant from the electrostatic atomizing apparatus 200 and water is conveyed from the feed-water means to the electrostatic atomizing apparatus 200 via a water passage by a water conveying means such as a pump; therefore, a home electrical appliance such as the refrigerator 1 or an air conditioner, or an appliance simple in structure and low in cost can be obtained.

Further, by placing the discharge electrode 230 to form the predetermined clearance Z directly below the water discharge spout 277 of the water storage tank 270, and by integrating the water storage tank 270 in a detachable manner with the fixing means 260, the conducting member 280, the discharge electrode 230, the counter electrode 240 and the electrode holding part 220 into a kit component in a state wherein they are positioned so as to form the predetermined clearance Z, water droplets dropping from the water storage tank 270 can be directly dropped to the discharge electrode simple in structure, and further, assembly efficiency and installing efficiency are improved. In addition, in a case of using the cooling plate 210 in place of the water storage tank 270, the cooling plate 210 can also be secured to the fixing means 260 (the pressing means) in a manner that the discharge electrode 230 is positioned directly below the heat absorbing fin part 211 so that dew condensation water that is condensed in at least the heat absorbing fin part 211 of the cooling plate 210 falls to the discharge electrode 230 directly. In this case, the distance between the water storage tank 270 or the heat absorbing fin part 211 and the discharge electrode 230 should be set to be the predetermined clearance Z. Setting of the predetermined clearance Z is as described above.

Here, since the main body part 232 of the discharge electrode 230 has an elongated shape in the axial direction, and a short shape in the depth direction (the length at right angle to the axial direction, or the thickness direction), the electrostatic atomizing apparatus 200 according to the present embodiment can be installed in a thin wall surface such as the ceiling wall forming a top surface of the storage compartments, side walls forming side surfaces of the storage compartments, and the partition wall 51 (a partition plate) that separates between the storage compartments in the refrigerator 1, or a small part in the depth direction in an air conditioner, etc., and a home electrical appliance such as the refrigerator 1, the air conditioner, etc. or an appliance can come down in thickness. Further, since the main body part 232 is elongated and the surface area is made large, water such as dew condensation water, supplied water, etc. can be received by a sufficient area, a sufficient amount of water such as dew condensation water, supplied water, etc. can be supplied to the protrusion part 231 by capillary action, and further, since the main body part 232 is elongated and the surface area is made large, even when a slight foreign matter exists in water and is attached to the surface of the main body part 232, water passes through a void inside the main body part 232 by capillary action and is supplied to the protrusion part 231 without any problem; thus, a filter, etc. that removes foreign matter in the dew condensation water or the supplied water is unnecessary, and the electrostatic atomizing apparatus 200 and a home electrical appliance that are capable of discharging nano-size mist within a warranty period (for example, duration of use of 10 years), low in cost and highly reliable can be obtained. In this case, the length in the axial direction and the cross-sectional shape of the main body part 232 in the discharge electrode 230 should be set to such a degree that the size of the surface area capable of supplying water to the protrusion part 231 can be ensured by supposing foreign matter in water in the warranty period (for example, about 10 years) of a product.

Further, in respect of installation of the electrostatic atomizing apparatus 200, since the main body part 232 is made to have an elongated shape and is small in thickness in the depth direction, even when the protrusion part 231 is arranged to protrude in the lateral direction (for example, an approximate horizontal direction) from the main body part 232, it is possible to obtain the electrostatic atomizing apparatus 200 that is compact with a small thickness, which can be installed in the side walls, the ceiling wall, the partition wall or an installation place small in depth, etc.; however, the thickness in the depth direction can be made smaller when the protrusion part 231 is arranged to protrude in an approximate upper direction or an approximate lower direction from the main body part 232, in which case, it is possible to obtain the electrostatic atomizing apparatus 200 that is compact with a small thickness, which can be installed in the side walls, the ceiling wall, the partition wall or an installation place small in depth, etc.

In the above, the water storage tank 270 is used for the water supply means, and the electrode holding part 220 that secures or houses the discharge electrode 230 is made to be in the container shape so as to be able to collect water; however by forming the main body part 232 of the discharge electrode 230 in a rectangular parallelepiped shape or a planar shape with a width (in the present embodiment, as shown in FIG. 12, a rectangular parallelepiped having an approximately square shape, or a square, with a width X3 and a length X2), and by installing the main body part 232 so that the upper surface with a width is set to be approximate horizontal (it is also acceptable that the main body part 232 slightly slants, and the slant is equal to or lower than 5 degrees, for example) at the time of installation, the electrode holding part 220 needs not be formed in a container shape that is capable of accumulating water, and it is only necessary that the electrode holding part 220 is in a shape (a discharge electrode fixing part) capable of fixing the discharge electrode 230 (for example, the main body part 232).

In the present embodiment, the discharge electrode 230 consisting of the main body part 232 formed of foam metal having a three-dimensional net structure, and the protrusion part 231 whereto water attaching to the surface of the main body part 232 is supplied by capillary action, the electrode holding part 220 that holds the discharge electrode 230, the counter electrode 240 placed in the electrode holding part 220 so as to be opposed to the protrusion part 231, and the water supply means (for example, the heat absorbing fin part 211 or the water storage tank 270) that is placed directly above the main body part 232 of the discharge electrode 230 to supply water to the discharge electrode 230 are included, wherein the main body part 232 is in the approximately rectangular parallelepiped shape elongated in the axial direction, in which the dimension of the upper surface having the planar shape is made large by making the width larger than the thickness, and further, the dimension that receives water can be increased in size by installing the main body part 232 so that the upper surface that receives water is set to be approximate horizontal.

That is, although the water droplet 275 supplied from the water storage tank 270 falls into the main body part 232 of the discharge electrode 230 directly below, the upper surface of the main body part 232 is in the shape having the surface in the approximately square shape with the width X3 and the length X2, and is installed to be approximate horizontal, hence the dropping water can be directly received by the upper surface of the main body part 232 in the planar shape, and the water falling to the upper surface is immediately absorbed inside the main body part 232 from the surface by capillary action, and is supplied to the protrusion part 231. Therefore, in this case, the shape of the electrode holding part 220 needs not be in the container shape since the electrode holding part 220 needs not accumulate water, and since the electrode holding part 220 has only to secure or hold the main body part 232 of the discharge electrode 230, when the amount of water dropping from the water storage tank 270 is too large and cannot be absorbed inside the main body part 232, it is applicable to form the water discharge spout whereby water can be discharged, such as the notch, the opening, etc., in the electrode holding part 220, and to separately form a discharging means in a lower part or a side of the water discharge spout of the electrode holding part 220, and so on, thereby water can be discharged to a lower part from the upper surface of the main body part 220 so that water is discharged outside of the electrostatic atomizing apparatus 200. For instance, in a case of an indoor unit of an air conditioner, the water can be discharged along with drain water, and in a case of a refrigerator, the water can be discharged outside along with defrosted water.

(Use of Defrosted Water)

Here, in a case in which the cooler compartment 131 wherein the cooler 13 is housed is arranged in the vicinity of the rear surface of the storage compartment (for example, the refrigerating compartment 2) wherein the electrostatic atomizing apparatus 200 is installed, as shown in FIG. 2, by providing a defrosting electrode holding part 152 in a shape capable of accumulating defrosted water, such as by forming the heater roof 151 provided below the cooler 13 into a container shape (a part in a shape (for example, a container) capable of accumulating water separately from the heater roof 151), and supplying the defrosted water accumulating inside the defrosting electrode holding part 152 to the electrostatic atomizing apparatus 200 via a defrosted water conveying part formed of a filter or felt, etc., using capillary action, etc., the defrosting electrode holding part 152 can also serve as the electrode holding part 220 inside the storage compartment; therefore, there is no need to provide the electrode holding part 220 inside the storage compartment, and further, the cooling plate 210 is unnecessary, hence the refrigerator 1 low in cost and simple in structure can be obtained.

Here, the heater roof 151 is provided to cover the above of the defrosting heater 150 so that defrosted water falling from the cooler 13 does not drop over the defrosting heater 150 directly; however, the size or the volume of the defrosting electrode holding part 152 has only to be a size or a volume at a degree capable of acquiring an amount of defrosted water required for mist atomization, hence the size or the volume should be determined in consideration of the number of defrosting or defrosting time, etc. Further, since it is only necessary for the defrosting electrode holding part 152 to have a size or a volume at a degree capable of acquiring the amount of defrosted water required for mist atomization, the defrosting electrode holding part 152 needs not be provided in the whole area of the heater roof 151, but has only to be provided in at least a part of the heater roof 151. The defrosting electrode holding part 152 is provided above the heater roof 151, and there is no problem even when too much defrosted water accumulates and overflows, since the defrosted water is discharged outside from a defrosted water discharge spout provided below, hence a response at the time when the defrosted water overflows from the defrosting electrode holding part 152 is unnecessary, and the refrigerator 1 low in cost and simple in structure can be obtained. Here, in the present embodiment, since the defrosting electrode holding part 152 that receives defrosted water (that often drops in a state of frost) dropping from the cooler 13 is used for the electrode holding part in the electrostatic atomizing apparatus 200, the defrosted water is often collected by the defrosting electrode holding part 152 in a state of frost, and since the frost gradually melts, the defrosting electrode holding part 152 can keep the defrosted water for a long time. Therefore, even when a defrosting operation is performed once a day, defrosted water can be kept in the defrosting electrode holding part 152 for a long time, and it is possible to stably spray mist.

Especially, by using a heater of a black medium such as a carbon heater, etc. for the defrosting heater 150, which is a defrosting means, since frost on the cooler 13 can be efficiently melted from the surface or the inner surface by radiation heat transfer, the rate at which the frost attaching to the cooler 13 drops in a state of frost gets lower; therefore, there is no possibility that defrosted water drops to the defrosting electrode holding part 152 only in a state of frost and does not drop in a state of water, and cannot be used for electrostatic atomization. Furthermore, since the defrosted water drops also in a state of frost moderately, the frost gradually melts, the defrosted water can be kept in the defrosting electrode holding pat 152 for a long time, and mist can be stably sprayed for a long time. In addition, by using a fitting type heater that is integrally provided with the cooler 13 together for the defrosting means, since heating from the side of the cooler 13 is also possible, the frost attaching to the cooler 13 can be heated from the inner side (the fitting heater) and the outer side (the carbon heater, which is the defrosting heater, etc.), and the ratio of water and frost which are falling to the defrosting electrode holding part can be set as needed. For example, in this case, by a user setting by a switch, etc. provided on the control panel 60, or by the control device 30 setting beforehand and controlling an applied voltage and a timing of voltage application, etc. of each of the fitting heater and the defrosting heater, predetermined defrosted water that is required for mist atomization and moderate can be kept in the defrosting electrode holding part 152 continuously for a long time, and an effect that mist can be sprayed more stably is obtained.

Further, it is also acceptable to include a hot gas defrost circuit that directly passes a high temperature refrigerant in a refrigerating cycle in the cooler 13 and performs defrosting of the cooler 13 without using the defrosting heater 150, etc. as a defrosting means.

In this case, it is acceptable to make up a refrigerating cycle by connecting in series the compressor 12 that compresses a refrigerant, a switch valve (not shown in the diagrams), a condenser that condenses the refrigerant compressed by the compressor 12 (not shown in the diagrams), a decompression device that decompresses the refrigerant condensed by the condenser (not shown in the diagrams), and the cooler 13 that generates cool air to cool the storage compartments by evaporating the refrigerant decompressed by the decompression device, and to attach the hot gas defrost circuit that performs defrosting of the cooler 13 by bypassing high temperature refrigerant gas compressed by the compressor 12 to the cooler 13 via the switch valve, and passing the high temperature refrigerant gas compressed by the compressor 12 to the cooler 13.

When the hot gas defrost circuit (the bypass circuit) is included in this manner, in a case of performing defrosting, by switching the switch valve and passing high-temperature and high-voltage refrigerant compressed by the compressor 12 directly to the cooler 13 in the hot gas defrost circuit without passing the high-temperature and high-voltage refrigerant to the condenser, it is possible to melt frost from inside of the frost by heating frost attaching to the cooler 13 from the surface of the cooler 13 by high-temperature refrigerant, and perform defrosting efficiently in a short time.

Additionally, by using a heater of black medium (a glass tube heater, etc.) such as a carbon heater capable of using radiant heat transmission as the second defrosting means together with the hot gas defrost circuit (the bypass circuit) as the second defrosting means, it is possible to melt frost more efficiently. In this case, by using the defrosting heater 150, which is the second defrosting means, also as a heating means that heats frost or defrosted water inside the defrosting electrode holding part 152, it is unnecessary to provide a heating means separately, and the refrigerator 1 low in cost and simple in structure can be obtained. Here, it is also acceptable to use a bypass piping in the hot gas defrost circuit (the bypass circuit), which is the first defrosting means, for a heating means to heat frost or defrosted water inside the defrosting electrode holding part 152. In this way, it is unnecessary to provide a heating means separately, and the refrigerator 1 that is inexpensive and capable of collecting defrosted water efficiently, and further, spraying mist stably can be obtained.

Here, as for energization control of a heating means, a mist spray switch 60*e* for actuating the electrostatic atomizing apparatus 200 is formed in the control panel 60 installed in a front surface of an opening and closing door (for example, the refrigerating compartment door 7) that is provided so as to cover an opening of a front surface of a storage compartment (for example, the refrigerating compartment 2) in the refrigerator 1, and the heating means can be actuated by controlling the mist spray switch 60*e*. It is applicable that the electrostatic atomizing apparatus 200 is energized only for a predetermined time when the mist spray switch 60*e* is controlled, or only for a set time by configuring in such a manner that a user can arbitrary set an operation time within a range of a predetermined time. Further, it is also applicable that the heating means is operated only for a predetermined time in conjunction with opening or closing of the opening and closing door of the storage compartment wherein the electrostatic atomizing apparatus 200 is installed. Also in this case, it is applicable that an energization time of the heating means may be set by an experiment, etc. beforehand, or a user may arbitrary set the time by oneself within the range of the predetermined time that is set beforehand.

In this case, an end of the defrosted water conveying part formed of felt, etc. is allocated in the defrosting electrode holding part 152 via a filter, and the other end of the defrosted water conveying part may be directly connected to the electrode holding part 220, or may be allocated inside the electrode holding part 220 when the electrode holding part 220 is provided in the storage compartment. Additionally, by setting that defrosting of the cooler 13 is performed periodically (for example, at least once or more times per a day), lack of water supply to the electrostatic atomizing apparatus 200 does not occur, and water droplets made into nano-size mist can be stably supplied inside the storage compartment (inside the refrigerator). Now, even when the cooler compartment 131 or the cooler 13 is apart from the storage compartment wherein the electrostatic atomizing apparatus 200 is installed (for example, in a case in which the storage compartment wherein the electrostatic atomizing apparatus 200 is installed is placed in an upper part, and the cooler compartment 131 or the cooler 13 is placed in a rear surface of a storage compartment in a lower part, or in a case in which the storage compartment wherein the electrostatic atomizing apparatus 200 is installed is placed in a lower part of the refrigerator 1 and the cooler compartment 131 or the cooler 13 is placed in a rear surface of a storage compartment in an upper part of the refrigerator 1), by making the defrosted water conveying part to have a structure capable of making use of capillary action, or to use a material, etc. capable of making use of capillary action, water can be stably supplied to the electrostatic atomizing apparatus 200 without any difficulty. Further, when there is a possibility that water inside the defrosted water conveying part freezes, it is applicable to insulate the surrounding of the defrosted water conveying part at least in an area where freeze may occur by providing a heat insulating material in the surrounding, or to place the defrosted water conveying part by burying the defrosted water conveying part in a heat insulating material of the partition wall and so on.

Especially in a case wherein the refrigerating compartment 2 and the vegetable compartment 5 are placed in the upper part of the refrigerator 1, a cooler for the refrigerating compartment and a cooler for the vegetable compartment are also placed in the upper part of the refrigerator 1 aside from the cooler 13 for the freezing compartment 6, and the cooler for the refrigerating compartment and the cooler for the vegetable compartment are allocated in a back side of the refrigerating compartment 2 and the vegetable compartment 5, since the defrosting electrode holding part 152 is provided in the upper rear surface of the refrigerator 1 (the cooler for the refrigerating compartment and the cooler for the vegetable compartment are allocated in the back side of the refrigerating compartment 2 and the vegetable compartment 5), when the electrostatic atomizing apparatus 200 is installed in the refrigerating compartment 2 or the vegetable compartment 5, the length or arrangement of the defrosted water conveying part can be shortened and simplified, and the refrigerator 1 low in cost, simple in structure, without problem even when defrosted water overflows can be obtained.

As for the electrostatic atomizing apparatus 200, a mist spray switch 60*e* for actuating the electrostatic atomizing apparatus 200 is formed in the control panel 60 installed in the front surface of an opening and closing door (for example, the refrigerating compartment door 7) that is provided so as to cover the opening of the front surface of a storage compartment (for example, the refrigerating compartment 2) in the refrigerator 1, and the electrostatic atomizing apparatus 200 can be actuated by controlling the mist spray switch 60*e*. It is applicable that the electrostatic atomizing apparatus 200 is energized only for a predetermined time when the mist spray switch 60*e* is controlled, or the electrostatic atomizing apparatus 200 is operated only for a set time by configuring that a user can arbitrary set an operation time within a range of a predetermined time. Further, it is also applicable that the electrostatic atomizing apparatus 200 is operated only for a predetermined time in conjunction with opening or closing of the opening and closing door of the storage compartment wherein the electrostatic atomizing apparatus 200 is installed. Also in this case, it is applicable that an energization time of the electrostatic atomizing apparatus 200 may be set by an experiment, etc. beforehand, or a user may arbitrary set the time by oneself within the range of the predetermined time that is set beforehand.

Additionally, in a case of using defrosted water for the electrostatic atomizing apparatus 200, by making the electrostatic atomizing apparatus 200 operate following the end of defrosting, lack of water does not occur inside a defrosted water collecting part, and electrostatic atomization can be performed certainly. In this case, if the end of defrosting is considered to be taking too much time, the electrostatic atomizing apparatus 200 may be made to operate not after the end of defrosting, but immediately after defrosting starts, or after a predetermined time passes after defrosting starts. Further, in a case of performing a defrosting operation at night, it is applicable to set the electrostatic atomization apparatus 200 to be able to operate at any time after the end of defrosting (or the start of defrosting, or during defrosting) and before the next defrosting operation starts. In this case, since defrosted water can be used without waiting for the start of defrosting or the end of defrosting, the electrostatic atomizing apparatus 200 can be operated when needed. Thus, water supply needs not be fed for spraying mist, and the electrostatic atomizing apparatus 200 that is maintenance free can be obtained. Here, it is also acceptable that water is fed to the electrostatic atomizing apparatus 200 from a feed-water tank that feeds water for making ice via a supply water conveying part (not shown in the diagrams) without using defrosted water in the defrosting electrode holding part 152. Further, as a water feeding means to the electrostatic atomizing apparatus 200, at least two of supplying dew condensation water by the cooling plate 210, supplying defrosted water by the defrosting electrode holding part 152, water supply from the feed-water tank, and other means, etc. can be used in combination.

(Application to an Approximate Closed Space in the Refrigerator)

Next, an explanation will be provided of a case wherein, as shown in FIG. 18, approximately closed containers 2X and 2Y are placed inside storage compartments such as the refrigerating compartment 2, etc., and the electrostatic atomizing apparatus 200 is allocated in the approximately closed containers 2X and 2Y. In the present embodiment, inside of the approximately closed container 2X is a chilled compartment 2A that is temperature-controlled to be in a chilled temperature zone approximately from −3° to +3° C., and inside of the approximately closed container 2Y is used as a vegetable reserving container or the vegetable compartment 5 that is controlled to be in a vegetable compartment temperature zone approximately from +3° to +5° C. Here, temperature control of inside of the approximately closed containers 2X and 2Y is performed by the cooling plate 210 of the electrostatic atomizing apparatus 200 in the present embodiment. That is, since the cooling plate 210 of the electrostatic atomizing apparatus 200 consists of the heat dissipating fin part 212 placed in the side of the cooling air trunk 50, and the heat absorbing fin part 211 placed in the approximately closed containers 2X and 2Y (inside the storage compartments), the cooling plate 210 has a structure to cool inside of the approximately closed containers 2X and 2Y in a direct cooling method by the heat absorbing fin part 211. When temperature control is difficult due to increase in temperature, etc. inside the approximately closed containers 2X and 2Y only by direct cooling by the cooling plate 210, an indirect cooling method to cool outside of the approximately closed containers 2X and 2Y indirectly by cool air can be combined.

Now, as for the structures of the approximately closed containers 2X and 2Y, by forming detachable lids to upper openings of the containers having the upper openings whose upper surfaces are opening, the containers having approximately closed structures can be formed. The lid may be provided in the container side, or in an inside refrigerator shelf 80, or a partition wall placed in the upper part of the container, and the shelf or the partition wall in the upper part of the container itself can be used as a lid as well. Further, in the present embodiment, an opening (a notch or an opening) enough for inserting at least a part of the electrostatic atomizing apparatus 200 (for example, the cover 300) is formed in the rear surface of the container, and a predetermined gap between the electrostatic atomizing apparatus 200 (for example, the cover 300), and the opening in the container is set as small as possible, i.e., approximately 0.5 mm to 2 mm in a state wherein at least a part of the electrostatic atomizing apparatus 200 is inserted in the approximately closed containers 2X and 2Y from the opening (the notch or the opening), and the containers are configured to be insusceptible to the outside temperature, and have approximately closed structures; therefore, inside of the approximately closed containers 2X and 2Y are insusceptible to temperatures outside the containers, temperature hunting inside the approximately closed containers 2X and 2Y lessens, and controllability of temperatures inside the approximately closed containers 2X and 2Y increases. In this case, by configuring the predetermined gaps between the electrostatic atomizing apparatus 200 and the openings of the approximately closed containers 2X and 2Y to be blocked or sealed in a state wherein the approximately closed containers 2X and 2Y are inserted and installed inside the storage compartment in the refrigerator 1, the predetermined gap can be made smaller and approximately closed, hence the containers become more unsusceptible to the outside temperature, and controllability of temperatures inside the approximately closed containers 2X and 2Y increases further. Additionally, since the insides of the containers are approximately closed, humidity retention effect is obtained inside the containers due to effect of moisture in the nano-size mist sprayed in the containers, and due to ozone effect and radical effect in the mist, antibacterial, deodorizing, antifouling and bacterial eradication effects inside the containers can be attained, and these effects increase more than in a case in which an approximately closed structure is not formed.

(Application to a Supercooling Compartment)

Next, in the present embodiment, an explanation will be provide of a case in which the electrostatic atomizing apparatus 200 is installed inside a storage compartment, for example, the switching compartment 4, and the switching compartment 4 is set a supercooling freezing (instant freezing) setting. First, the instant freezing switch 60c (supercooling freezing) is provided in the control panel 60, hence it will be briefly explained from a flow of supercooling freezing. It is assumed that the switching compartment 4, which is a storage compartment, in the refrigerator 1 is cooled to a freezing temperature (for example, approximately −7° C.). An air temperature in the switching compartment 4 is detected by the switching compartment thermistor 19, and by opening and closing the switching compartment damper 15, temperature fluctuation is suppressed to approximately ±1K. After inserting a stored product in the switching compartment 4 that performs supercooling freezing, a user presses a switch on the control panel 60 (the instant freezing switch 60c of compartment selection switch 60a to the mist spray switch 60e) (here, instant freezing is supercooling freezing (in order to prevent "supercooling" being falsely recognized as "cooling too much," "instant freezing" is used as another expression to represent freezing instantly)). When the instant freezing switch 60c is pressed, a detected temperature processing (estimation processing of a surface temperature) of the thermopile 22 is started by the control device 30. When an estimated temperature T1 reaches around −2 to 1° C. by repeatedly calculating and estimating a surface temperature of the stored product inside the switching compartment 4 on a periodic basis (at every predetermined time interval), lowering of a set temperature in the switching compartment 4 is started so that the switching compartment 4 is gradually cooled to a lower temperature. When cooling proceeds, a supercooled state is released at a certain timing, and moisture inside the stored product freezes immediately. After the moisture freezes, instant freezing is performed by blowing cool air rapidly into the switching compartment 4, or by lowering the set temperature further in order to freeze the parts other than the moisture as soon as possible, and when the parts other than the moisture is frozen, supercooling freezing is completed. While the user is manipulating the controlling panel 60, pressing the instant freezing switch 60c, and performing control of "instant freezing (supercooling freezing)," it is displayed on the control panel 60 that it is during "instant freezing."

The above describes an example wherein temperature detection in the switching compartment 4 is performed by the switching compartment thermistor 19, and temperature detection of the stored product 25 that is put in is performed by the thermopile 22; however, it is also acceptable that, for example, the temperature in the switching compartment 4 is detected by the thermopile 22, and by opening and closing the switching compartment damper 15, the temperature in the switching compartment 4 is controlled. That is, it is also applicable to have both temperature detection of the air temperature inside the storage compartment and temperature detection of the surface temperature of the stored product performed only by the thermopile 22, which is a temperature detecting means.

It is also applicable that the temperature T1 of the stored product during a supercooling freezing process is directly displayed in numerical value on the control panel 60. It becomes possible for the user to see the surface temperature T1 of the stored product, and check a progress status of supercooling freezing, and normal freezing, etc.

Now, supercooling freezing (supercooled freeze) will be described in more detail. The refrigerator 1 according to the embodiment of the present invention maintains a stable temperature environment that is necessary for realizing supercooling stably, including a control mechanism that controls a temperature and cool air, such as a temperature, a wind speed, an air volume, a timing, etc. of direct blowing of cool air to a food item, a structure of a casing, etc. that houses the food item, a device or a control mechanism that determines completion of supercooling necessary for realizing releasing of supercooling certainly, and a device or a control mechanism that provides a stimulus which is considered necessary for releasing of supercooling. Further, the refrigerator 1 also includes a function of cooling and reserving for maintaining freezing of good quality after releasing of supercooling.

Here, supercooling freezing is divided into five states as follows according to a food item temperature.

(1) Unfrozen state: The food item temperature is equal to or higher than a freezing point of the food item.

(2) Supercooling state: The food item temperature is equal to or lower than the freezing point of the food item, and the food item is not frozen. It is recognized to be in the supercooling state since the food item temperature keeps on declining.

(3) Releasing of supercooling: The food item temperature returns to the freezing point from a temperature equal to or low than the freezing point.

(4) Start of freezing to freezing completion state: A state wherein the food item reaches the freezing point, a phase transition occurs (if it is water, liquid water is transformed into a solid ice), and the food item remains at a certain temperature.

(5) Freezing completion and freezing reserve state: A state wherein the food item is frozen after undergoing the process of (4).

Now, freezing points of major food items will be described. The freezing point is −1.7° C. for beef or pork; −1.3° C. for tuna; −1.7° C. for potatoes; −1.2° C. for strawberries; and −2.0° C. for apples (book for reference: Sougo-syokuryo-kogyo, 1975, p. 922).

There is a condition necessary for entering supercooling (to make a food item reach a temperature equal to or lower than a freezing point in an unfrozen state) and a condition for promoting supercooling (lowering a temperature that is reached in a supercooling state) in the states (1) to (2), a condition for releasing the supercooling state and starting freezing in (3), and conditions for keeping quality of the food item that is supercooled frozen in (4) and (5). When a sufficiently increased supercooling degree (temperature difference between the freezing point of the food item and a temperature reached by supercooling) is obtained by controlling (1) to (3), the effect does not disappear by (4) and (5). However, in a case wherein a supercooling state is maintained, when the door is opened for a long time because of moving a food item in and out, or a set temperature is equal to or higher than the freezing point, and a temperature inside a supercooling compartment becomes, for example, equal to or higher than 0° C. and the supercooling state is released, the process is started again from the state (1) once again.

Next, the processes of (1) to (3) will be described.

First, an explanation will be provided based on an examination result at the time a slice of beef with a thickness of 15 mm and a weight of 150 g is inserted as a food item. A condition for supercooling in a supercooling compartment (the same as a supercooling space) in the refrigerator 1 in the present invention will be described. The points to be noted at the time of setting the condition for supercooling are a cooling speed, and a difference between a lowest mark (a temperature that is reached in a supercooling state) of a core temperature of the food item to be cooled and a freezing point, etc. If the cooling speed is too fast, the food item is cooled in an uneven state of temperatures in the entire food item, hence, a frozen part and an unfrozen part are generated (the difference between the surface temperature and the core temperature of the food item is large). Since an ice crystal grows from an ice nucleus as a center, even when only a part of the food item is frozen, the ice crystal grows from the ice nucleus by introducing moisture in an unfrozen part. As a result, a large acicular ice crystal is produced. The acicular ice crystal or a large ice crystal generated between cells, etc. leads to outflow of moisture or destruction of cells, and causes drip loss at the time of thawing of the food item.

The result is that original juiciness of the food item is reduced, nutrition such as free amino acid is reduced, and the texture gets worse. Meanwhile, too slow a cooling speed is less of a problem with maintaining of the cooling state, but is a problem with the quality of the food item getting worse by a growth of bacteria and oxidation, etc. because the unfrozen state is lengthened. That is, the unfrozen state is prevented from being long by cooling so as to make the difference between the surface temperature and the core temperature small until the freezing point, and by increasing the cooling speed so that the temperature quickly reaches a lowest mark of the core temperature, and releasing supercooling when the temperature reaches a temperature equal to or lower than the freezing point (in a supercooling state). In this way, temperature control and cool air conditioning until the food item reaches the freezing point, until the food item reaches the supercooling state equal to or lower than the freezing point, and until the food item completely freezes after release of supercooling are respectively performed in a continuous or phased manner. In order to resolve such a problem—, there is also a method to add an antibacterial function to the supercooling space. As the antibacterial function, there is a method of using ultraviolet or ozone, and so on.

In the present embodiment, the electrostatic atomizing apparatus 200 is installed in a storage compartment (for example, the switching compartment 4) that performs supercooling freezing. By installing the electrostatic atomizing apparatus 200, when a supercooling state is maintained, it is possible to spray water droplets that are made into nano-size mist by operating the electrostatic atomizing apparatus 200, and a growth of bacteria and oxidation, etc. can be prevented by ozone, radical, etc. in nano-size mist; therefore, a refrigerator and a food reservation method in the refrigerator is obtained wherein it is possible to prevent that the original juiciness of the food item is reduced, that nutrition such as free amino acid is reduced, and that the texture gets worse even when the unfrozen state is lengthened by making the cooling speed slow and maintaining the supercooling state for a long time at the time of controlling supercooling freezing, and further, since the food item can be preserved in a supercooling state (unfrozen state) for an extended period, it is possible to obtain a preserved food whose thawing is unnecessary, original juiciness can be retained, nutrition such as free amino acid is not reduced, and texture is good.

Further, since it is possible to spray water droplets miniaturized and made into nano-size mist, the water droplets can be sprayed uniformly in the storage compartment, and a stored item is kept fresh and prevented from dryness by the water droplets made into nano-size mist. Therefore, a stored item in a supercooling state, a stored item in a supercooling freezing state, and a stored item in a normal cooling state can be kept fresh and prevented from dryness, the quality of the food item does not get worse, and the refrigerator 1 capable of keeping items fresh, clean, highly reliable and capable of performing cooling, freezing, supercooling and supercooling freezing can be obtained.

In a case of supercooling freezing, a time (a time for which a supercooling state and an unfrozen state can be kept) it remains in an unfrozen and supercooling state in a temperature zone (around −10° C. to −1° C.) including and around a largest ice crystal generation zone (−5° C. to −1° C.) is long (the time of passage is long) compared to normal freezing or instant freezing, etc. However, in a case of a supercooling state, even if the time of passage in the temperature zone (around −10° C. to −1° C.) including the largest ice crystal generation zone (−5° C. to −1° C.) is long, an ice crystal after being frozen does not become large, and approximately uniform fine ice crystals can be produced. In freezing using the temperature zone including and around the largest ice crystal temperature zone, the way of supercooling freezing in the present invention is a new freezing method in that small ice crystals are formed in large numbers, and it is a high quality freezing. Further, in the supercooling freezing in the present invention, it is confirmed that when a supercooling state is released, freezing starts, and an item is completely frozen after undergoing a phase transition state wherein a temperature does not change; however, when the item undergoes the supercooling state, even when a time it takes to pass through the largest ice crystal generation zone is long (even when it remains in the largest ice crystal generation zone for a long time) in a freezing process after that, ice crystals are not enlarged, are fine and approximately evenly formed in the whole food item, and supercooling freezing of good quality can be performed, in which point, the supercooling freezing in the present invention can be said a new freezing method.

There is no problem only if a food item undergoes a supercooling state even if a freezing process after that takes a long time, since it has little effect on an ice crystal condition; however by performing freezing rapidly when the food item enters a freezing process after the supercooling state is released, a possibility for ice crystals to become enlarged gets much lower, and the food item of good quality can be gained. Further, since it is also possible to avoid a lowering factor (for example, bacteria growth, etc.) of the quality of the food item other than the factor related to ice crystals, freezing of better quality can be performed.

In the above, it is described until this point a case wherein a food item that has entered a supercooling state is released from supercooling and is frozen; however, there is no necessity to freeze the food item that has entered the supercooling state. As for an advantage of supercooling preservation to keep the supercooling state without freezing the food item is in that since the food item is not frozen at all and ice crystals are not generated at all even though the food item is preserved at a temperature equal to or lower than a freezing temperature, i.e., a temperature at which the food item is frozen under normal conditions, the food structure rarely undergoes a transition due to ice crystals while being preserved at a low temperature. Preservation at a lower temperature is effective in preserving freshness on the point that various chemical changes of the food item can be prevented, and both advantages of preservation at a low temperature and being unfrozen can be attained by the present invention (supercooling preservation and supercooling freezing). Further, since the food item is in a supercooling state and is in an unfrozen state, there is no need to thaw the food item. However, the supercooling state is an unfrozen state, and when moisture in the food item is unfrozen, the moisture may be used for growing bacteria or various chemical changes, but it is considered that food quality can be maintained in a good state by performing supercooling freezing to have a food item frozen after undergoing a supercooling state as in the present invention. Therefore, preservation in a supercooling state (supercooling preservation) may be inferior in food quality to (require more attention than) that in a frozen state (supercooling freezing); however, preservation in the supercooling state is in a level without problem when it is a short-term preservation (for example, about one to three weeks).

Now, the electrostatic atomizing apparatus 200 installed in a storage compartment (for example, the switching compartment 4) wherein supercooling freezing control is performed may be operated simultaneously with start (for example, control of the instant freezing switch 60c formed in the control panel 60) of supercooling freezing control, and may be operated in the middle of supercooling freezing control. Here, the electrostatic atomizing apparatus 200 should be set to finish its operation at a predetermined temperature (for example, a temperature of a freezing point, i.e., 0° C. in a case of water) at which the heat absorbing fin part 211 of the cooling plate 210 or dew condensation water that has condensed in the heat absorbing fin part 211 does not freeze.

That is, when the instant freezing switch 60c formed in the control panel 60 is operated, the supercooling freezing control is started and the temperature in the storage compartment is gradually decreased, and in the meantime, the electrostatic atomizing apparatus 200 is operated simultaneously with start (for example, manipulation of the instant freezing switch 60*c* formed in the control panel 60) of supercooling freezing control or after a lapse of a predetermined time after start of supercooling freezing control, then at the time a detected temperature of the switching compartment thermistor 19, which is the first temperature detecting means, (or the thermopile 22, which is the second temperature detecting means, can be used as a substitute) installed in the storage compartment (for example, the switching compartment 4) reaches the predetermined temperature, the operation of the electrostatic atomizing apparatus 200 is finished.

Here, it is also applicable that the electrostatic atomizing apparatus 200 is operated in a case wherein the instant freezing switch 60*c* formed in the control panel 60 is operated, and supercooling freezing control is performed after a lapse of a predetermined time. In this way, since dew condensation water can be sprayed in the storage compartment by the electrostatic atomizing apparatus 200 before supercooling freezing control starts, preservation in a supercooling state or preservation in a supercooling freezing state can be performed in a state wherein a stored item is moisturized.

Here, in a case when the high-voltage power supply part 250 of the electrostatic atomizing apparatus 200 may be damaged by dew condensation or freezing, it is applicable to form the high-voltage power supply part 250 of the electrostatic atomizing apparatus 200 as a separate member without forming it integrally with the electrostatic atomizing apparatus 200 as a kit, and to install the high-voltage power supply part 250 as a separate member, not in a storage compartment, but in the control device 30 having no risk of freezing or dew condensation, etc., for instance. Further, in a case in which the electrostatic atomizing apparatus 200 is installed in the storage compartment wherein supercooling freezing or freezing is performed to perform freezing preservation by providing a heating means in a vicinity of the electrostatic atomizing apparatus 200, even when the cooling plate 210, the electrode holding part 220, and the discharge electrode 230, etc. are frozen, they can be unfrozen by applying an electrical current to the heating means, and the electrostatic atomizing apparatus 200 can be used again immediately when the temperature inside the storage compartment rises. The electrostatic atomizing apparatus 200 operates also when the mist spray switch 60*e* formed in the control panel 60 is controlled.

It is also applicable that as an initial setting of the mist spraying apparatus (the electrostatic atomizing apparatus 200), the operation of the mist spraying apparatus (the electrostatic atomizing apparatus 200) is set to operate only when the mist spray switch 60*e* is manipulated, and a setting of a timing (setting the timing of the electrostatic atomizing apparatus 200 to operate, such as whether it operates and stops in conjunction with control of the instant freezing switch 60*c*, whether it operates at predetermined intervals, whether it operates and stops in conjunction with opening and closing of a door, whether it operates and stops in conjunction with an outer air temperature or a temperature inside a storage compartment, whether it operates and stops in conjunction with on and off of the compressor 12 or the cool air circulation fan 14, or whether it operates and stops in conjunction with opening and closing of the damper device, and so on) or an operation time when the mist spraying apparatus (the electrostatic atomizing apparatus 200) operates can be set afterward when a user selects a compartment with the compartment selection switch 60*a*, or performs a temperature setting in a storage compartment with the temperature zone transfer switch 60*b*, in which case the electrostatic atomizing apparatus 200 may be made to operate in conjunction with control of the other control switches, the temperatures in the other storage compartment, opening and closing of the door, or on and off of the compressor 12 or the cool air circulation fan 14, and so on, without need of controlling the mist spray switch 60*e*.

Further, by including both a direct cooling air trunk and an indirect cooling air trunk, and by installing a flow volume control means such as a damper as well in at least one storage compartment, so as to make it possible to switch indirect cooling and direct cooling, it is possible to provide the refrigerator 1 or a storage including a storage compartment wherein instant freezing, normal freezing, supercooling freezing and supercooling reservation are switchable, and capable of spraying nano-size mist by electrostatic atomization. Furthermore, since it is possible to switch (choose using) indirect cooling and direct cooling, a storage compartment (for example, the switching compartment) can be made under high humidity by switching to indirect cooling, and can be used also as a vegetable storage compartment capable of maintaining a high humidity state by spraying nano-size mist, hence it is possible to provide the refrigerator 1 or the storage that is clean and capable of preserving a vegetable fresh. In addition, since the electrostatic atomizing apparatus 200 is allocated in the storage compartment, it is possible to evenly spray fine nano-size mist in the storage compartment, perform bacterial eradication, provide antibacterial effect, preserve freshness, and prevent drying, etc. inside the storage compartment.

Further, since as a high-quality freezing function, a supercooling freezing function is adopted in addition to a conventional instant freezing, and further, the electrostatic atomizing apparatus 200 can be included, there is an effect that high-quality freezing capable of preventing drying using less energy than a conventional one, that is, an energy-saving freezing can be realized as a measure for global environment, can be realized.

Furthermore, by introducing cool air in a space for performing supercooling and by adopting a cooling structure capable of controlling temperatures wherein cooling temperatures can be changed to plural temperatures, there is an effect that supercooling freezing of a food item including edible meat can be realized, and further, since nano-size mist can be sprayed, it is possible to perform bacterial eradication, provide antibacterial effect, and prevent drying, etc. inside the storage compartment with a structure and control of a refrigerator that is not different greatly from the conventional one.

According to the present invention, since an infrared sensor, for example, is used as the temperature detecting means, a surface temperature of a food item can be measured, a temperature (for example, the surface temperature of the food item) closer to the food item can be detected, and thus, success rate of supercooling freezing rises, and freezing preservation (supercooling freezing) of fine food quality can be provided.

According to the present invention, since a supercooling freezing function to perform freezing after the supercooling state is included, it is possible to perform freezing of high quality wherein sizes and shapes of ice crystals generated at the time of freezing are less likely to damage a structure of an original food item. Further, since the ice crystals are small, a state close to an original state can be obtained even the ice crystals are broken, and food quality such as taste, texture, a preservation state, etc. of the food item at the time of defrosting is favorable. Furthermore, since supercooling freezing to perform freezing after the supercooling state is included, ice nuclei are small and fine, and the ice nuclei are approximately uniformly formed all over a refrigerated object, such as a food item, hence the food quality is better than that in a case of normal freezing or instant freezing. Additionally, since miniaturized nano-size mist can be uniformly sprayed in a storage compartment, there is an effect that it is possible to perform bacterial eradication, provide antibacterial effect, and prevent drying prevention as well.

Further, in a food item whereto supercooling freezing is performed in the refrigerator 1 of the present invention, since a cooling speed at the time of creating a supercooling state is slow, ice crystals begin to grow at a time after the temperature declines uniformly to the inside of the food item, and there is no possibility that ice crystals partly generated unevenly grow, and the size of the ice crystals generated inside the food item are small and approximately even; therefore, food quality can be maintained, and further by installing the electrostatic atomizing apparatus 200, it is possible to prevent drying of the food item, perform bacterial eradication, and provide antibacterial effect, etc. in a storage compartment, hence food quality is less likely to deteriorate even though a stored item is preserved for a long time in the supercooling state.

The refrigerator 1 in the present invention includes the freezing compartment 6 capable of adjusting temperatures of a housed food item continuously or in a phased manner from 0° C. to a temperature in a freezing temperature zone by cooling air circulating from the cooler 13, the cooling compartment which is allocated inside the freezing compartment 6, and which maintains a food item in the supercooling state wherein the food item is not frozen even at a temperature equal to or lower than a freezing point by taking in cool air that is blown from the cool air outlet of the freezing compartment 6 and is absorbed in the cooler 13, a temperature setting means which sets a temperature in the freezing compartment 6 equal to or lower than −2° C. but equal to or higher than −15° C. so that the food item stored in the cooling compartment achieves a supercooling state, a cool air conditioning means which conditions the cool air blown into the freezing compartment 6 and taken in the cooling compartment so as to prevent air speed surrounding the food item housed in the cooling compartment, and to maintain the stored food item in the cooling compartment to be in the supercooling state, a supercooling release means which releases the supercooling state by changing the air speed or the temperature, etc. surrounding the food item housed in the cooling compartment, and a freezing temperature setting means which performs freezing preservation at a set temperature lower than 0° C. whereby the food item is cooled rapidly by increasing the air speed surrounding the food item or lowering the temperature surrounding the food item after supercooling is released, and is capable of realizing energy-saving and high-quality freezing.

Here, the storage compartment which can perform supercooling cooling, supercooling freezing and instant freezing may be other than the switching compartment 4, and also the other storage compartments such as the freezing compartment 6, the vegetable compartment 5, etc. being configured to include a direct cooling air trunk and an indirect cooling air trunk, and be capable of switching air trunks may be made to perform supercooling freezing and instant freezing. In this way, any storage compartments can be used, and a user can set a preferred storage compartment to a preferred temperature zone or supercooling freezing at choice, and the refrigerator or the storage that is easy to use for a user can be provided. Furthermore, the electrostatic atomizing apparatus 200 can be installed in any storage compartments (for example, the refrigerating compartment 2, the switching compartment 4, the vegetable compartment 5, and the freezing compartment 6, etc.) if only a heating means is installed depending on temperature zones wherein the inside of the storage compartments are controlled.

(Display During Operation of the Electrostatic Atomizing Apparatus)

Next, it will be described a visual confirmation means with an example of the refrigerator 1 in a case wherein the visual confirmation means is installed in the cover 300 of the electrostatic atomizing apparatus 200 so that a user can visually confirm whether the electrostatic atomizing apparatus 200 is operating. In the present embodiment, as shown in FIG. 4, FIG. 5, FIGS. 18 to 20, at least one electrostatic atomizing apparatus light 600 of an LED, for example, is installed inside the cover 300 or on the cover 300 itself of the electrostatic atomizing apparatus 200 so that the user can visually confirm whether the electrostatic atomizing apparatus 200 is operating. The electrostatic atomizing apparatus light 600 is made to light up at the time the electrostatic atomizing apparatus 200 is operating, which is capable of lighting up or flashing when the electrostatic atomizing apparatus 200 is operating at the time the opening and closing door (the door) of the storage compartment is opened, which can be confirmed by a user visually. Here, when the electrostatic atomizing apparatus 200 is not operating at the time the opening and closing door (the door) of the storage compartment is opened, the electrostatic atomizing apparatus light 600 should preferably be used as a light inside the refrigerator, and lit up continuously in a color (for example, white) which can be used as the light inside the refrigerator. When the electrostatic atomizing apparatus 200 is operating at the time the opening and closing door (the door) of the storage compartment is opened, the electrostatic atomizing apparatus light 600 should preferably be made to flash or be turned off and so on, which can be visually confirmed by the user by a lighting method different from that in a case wherein the electrostatic atomizing apparatus light 600 is used as the light inside the refrigerator at the time the electrostatic atomizing apparatus 200 is not operating.

In a case wherein the electrostatic atomizing apparatus light 600 is installed inside the cover 300, when one or plural openings (for example, the front surface opening part 515, the side surface opening (not shown in the diagrams), the upper surface opening (not shown in the diagrams), or the lower surface opening (not shown in the diagrams)) which are openings with approximate sizes that a user cannot insert a finger therein are formed in the front surface or the both side surfaces, it is possible to notify that the electrostatic atomizing apparatus 200 is operating without any special devisal by placing the electrostatic atomizing apparatus light 600 at a position where the light from the electrostatic atomizing apparatus light 600 (for example, an LED or a lamp, etc.) leaks into the storage compartment from the openings as apertures. Further, also in the case wherein the electrostatic atomizing apparatus light 600 also serves as the light inside the refrigerator, it is possible to irradiate inside of the storage compartment without providing a light inside the refrigerator separately, and sufficient luminance can be ensured. On the other hand, by setting the position and the numbers of the openings as apertures in the cover 300 so that inside the storage compartment can be evenly irradiated with sufficient luminance, since the inside of the storage compartment can be irradiated during operation of the electrostatic atomizing apparatus 200, it is possible to notify that the electrostatic atomizing apparatus 200 is operating without any special devisal. In addition, even when the electrostatic atomizing apparatus light 600 serves also as the light inside the refrigerator, since the electrostatic atomizing apparatus light 600 can irradiate evenly inside the storage compartment without providing a light inside the refrigerator separately, the electrostatic atomizing apparatus light 600 can replace the light inside the refrigerator.

Here, by using a dual-color emission LED or two or more LEDs emitting different colors for the electrostatic atomizing apparatus light 600, it is possible to use the LED(s) separately in such a manner that an LED in white is used as a light inside the refrigerator that lights up at the time the door of the storage compartment is open, and an LED in blue, green or red is used as a light for the electrostatic atomizing apparatus that lights up at the time the electrostatic atomizing apparatus 200 is operating. Further, as a means that notifies a user visually that the electrostatic atomizing apparatus 200 is operating, a display such as "the electrostatic atomizing apparatus light is on" and so on is presented on the control panel 60 provided in the door of the storage compartment (for example, the refrigerating compartment 2), or a light (an LED, etc.) dedicated for indicating that the electrostatic atomizing apparatus is during the operation is provided and so on, so as to be able to notify the user by emitting a light in blue, green or red.

Further, by expressing an amount of sprayed mist or a degree of bacterial eradication (strength of bacterial eradication) inside a storage compartment by a strength (for example, quantity of an applied voltage or a sprayed amount of mist atomization, etc.) of the operation of the electrostatic atomizing apparatus 200 as a display of small, medium and large, or a size of a graph, such as a bar graph, or as a size or the number of a mark or a figure (for example, a figure such as a leaf mark, or a figure in a simple shape such as a square or a circle, etc.), a user can visually confirm the amount of sprayed mist or the degree of bacterial eradication, etc. immediately. Furthermore, in a case of displaying an amount of used electricity, electricity expense, and an amount of carbon dioxide emission, etc. in a figure such as a leaf mark, etc., it is also applicable that the figure is divided into multiple parts, the colors are changed in accordance with the number of division, and the amount of sprayed mist or the degree of bacterial eradication, etc. is displayed by the number of the divided parts whose colors are changed. In this way, it is possible to display the amount of sprayed mist, the degree of bacterial eradication, etc. also in a graphic display of the amount of used electricity, the electricity expense, and the amount of carbon dioxide emission, etc.; therefore, a display section is reduced in size, and further, a liquid crystal, etc. for display is small and can be controlled easily, hence a display device and a refrigerator moderate in price and small in size can be obtained. Further, since the amount of sprayed mist and the degree of bacterial eradication, etc. together with the amount of used electricity, the electricity expense, and the amount of carbon dioxide emission, etc. can be immediately confirmed by the user only by looking a display part in one place without need of looking at several parts, the refrigerator 1 that is user-friendly can be obtained.

Here, at least a part of the cover 300 may be formed of a resin material in color through which an inner light can transmit, such as transparent, white, milky white, yellow, light blue, etc., small in thickness, or a resin material etc. that is transparent or translucence and small in thickness so that the inner light can be visually confirmed from outside (for example, a thin resin in whitish colors, yellowish colors, bluish colors, or greenish colors, etc.), and by providing at least one (preferably plural) electrostatic atomizing apparatus light 600 inside the cover 300, the whole cover 300 may be made to emit light in color (for example, red, orange, blue, purple, etc.) from the inside of the cover 300. The cover 300 may be made to emit light in the color of the cover 300, or in the emission color of the electrostatic atomizing apparatus light 600. In this case, by not forming an opening or a slit, etc. in the front surface of the cover 300 so as not to leak light inside of the cover 300, but by forming an opening or a slit in the side surfaces or the upper and lower surfaces of the cover 300, etc. to let cool air and nano-size mist pass, and further by setting the electrostatic atomizing apparatus light 600 provided in the cover 300 to be an LED, etc. to emit light (for example, ultraviolet light at a level having less affect on the human body, etc.) of a wavelength having bacterial eradication, antibacterial effect, and deodorizing effect, light does not leak from the front surface of the cover 300 and a user is not illuminated with light directly; therefore, there is no influence on the human body, and bacterial eradication and deodorizing effects can be obtained by the electrostatic atomizing apparatus light 600, and bacterial eradication and deodorizing effects by spraying nano-size mist are improved.

By providing the electrostatic atomizing apparatus light 600 inside the cover 300 as just described, since the cover 300 can emit light in a wide range (for example, the whole cover 300, or at least a part of the cover 300), even when stored items such as food items, etc. are housed around the electrostatic atomizing apparatus 200, such as in the front of the electrostatic atomizing apparatus 200, it is possible to visually confirm at once that the cover 300 is emitting light from between the stored items. Further, it is also applicable to display directly on the cover 300 that the electrostatic atomizing apparatus 200 (the mist spraying apparatus) is operating, such as "during mist spray operation."

(Use of the Light Inside the Refrigerator for Display that the Electrostatic Atomizing Apparatus is During Operation)

Here, it is described in the above an example wherein the electrostatic atomizing apparatus light 600 is installed in the electrostatic atomizing apparatus 200 and it is visually confirmed that the electrostatic atomizing apparatus 200 is during operation; however, it is also applicable that the electrostatic atomizing apparatus 200 is during operation is visually confirmed by using a lighting device 900 in a storage compartment (inside a refrigerator) inside the refrigerating compartment 2, which is a storage compartment, for example. That is, it is also applicable to have the lighting device 900 inside the storage compartment also display that the electrostatic atomizing apparatus 200 is during operation.

Figure 21:
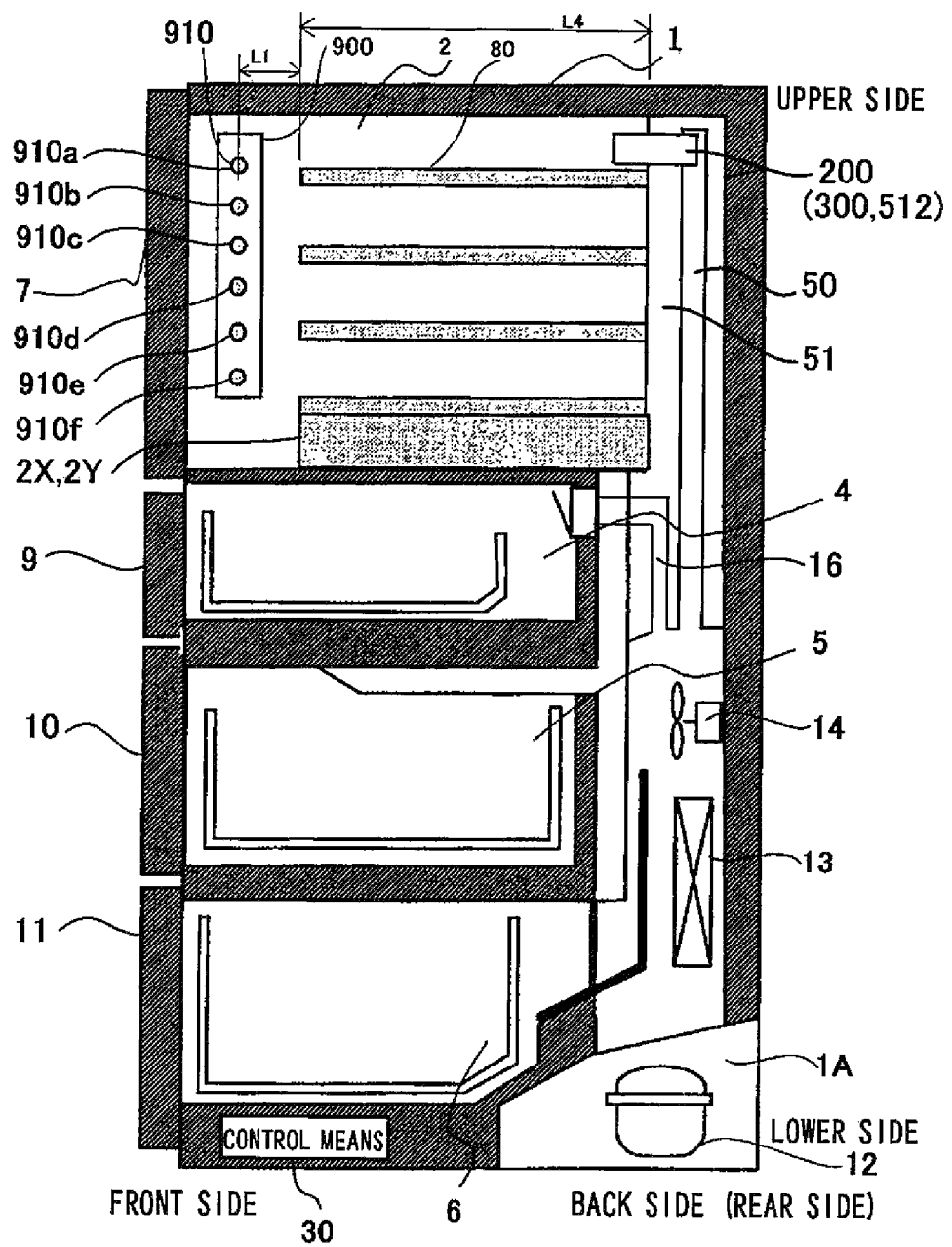
FIG. 21 is a schematic sectional side view of the refrigerator 1 describing the embodiment of the present invention.

FIG. 21 is a schematic sectional side view of the refrigerator 1 describing the embodiment of the present invention. The refrigerator 1 in the present embodiment includes plural storage compartments such as the refrigerating compartment 2, the ice making compartment 3 (not shown in the diagrams), the switching compartment 4, the vegetable compartment, and the freezing compartment 6 that include spaces to house stored items (food items, etc.). Further, the refrigerator 1 includes the hinged refrigerating compartment door 7, the slide-out ice making compartment door 8 (not shown in the diagrams), the switching compartment door 9, the vegetable compartment door 10, and the freezing compartment door 11, each of which opens and shields a space between inside and outside the compartment. A plural inside refrigerator shelves 80 (loading shelves) are provided in the refrigerating compartment 2, which is the storage compartment placed in the uppermost part of the refrigerator 1, and the approximately closed containers 2X and 2Y are placed below the inside refrigerator shelf 80 provided in the undermost level, which may be used as a chilled compartment that is temperature controlled in a chilled temperature zone of approximately −3° C. to +3° C., or may be used as a vegetable compartment or a vegetable preservation container that is controlled in a vegetable compartment temperature zone of approximately +3°

C. to +5° C. The switching compartment 4 is provided below the refrigerating compartment 2, and the vegetable compartment 5 is provided below the switching compartment 4. Further, the freezing compartment 6 is provided below the vegetable compartment 5 in the lowermost part of the refrigerator 1. Hereinafter, the refrigerating compartment 2 having the refrigerating compartment door 7 and the inside refrigerator shelves 80 (the loading shelves), etc. will be described; however, the refrigerating compartment 2 is not limited to this.

Here, the refrigerator 1 is in an approximately rectangular parallelepiped shape as shown in FIG. 21, and based on the installation direction of the refrigerator 1, a surface on the front side having the door is referred to as a front surface, and a surface on the back side with respect to the front surface is referred to as a back surface. Further, the upper side (the ceiling side) in FIG. 21 is referred to as a top surface, the lower side (the floor side) is referred to as a bottom surface, and the other two sides are referred to as side surfaces (here, from an anterior view, the left side is a left side surface, and the right side is a right side surface). Additionally, in the refrigerating compartment 2 which is opened and closed by the refrigerating compartment door 7, the plural inside refrigerator shelves 80 (the loading shelves) for loading stored items are plurally arranged in parallel so as to be approximately parallel to the top surface (or the bottom surface), thereby inside of the refrigerating compartment 2 is divided and storage efficiency of the stored items is improved.

Further, in the present embodiment, the control device 30 is provided in a bottom surface wall of the refrigerator 1 below the storage compartment (for example, the freezing compartment 6) provided in the undermost level of the refrigerator 1, which controls each means constituting the refrigerator 1. Of course, the control device 30 (the control means) may be provided in an upper part of the rear surface of the storage compartment (for example, the refrigerating compartment 2) provided in the uppermost level of the refrigerator 1. The control device 30 performs control for plural LEDs 910 (an LED 910*a*, an LED 910*b*, an LED 910*c*, an LED 910*d*, an LED 910*e*, and an LED 910*f*) included in the lighting device 900 mainly for illuminating inside of the refrigerating compartment 2.

Figure 22:
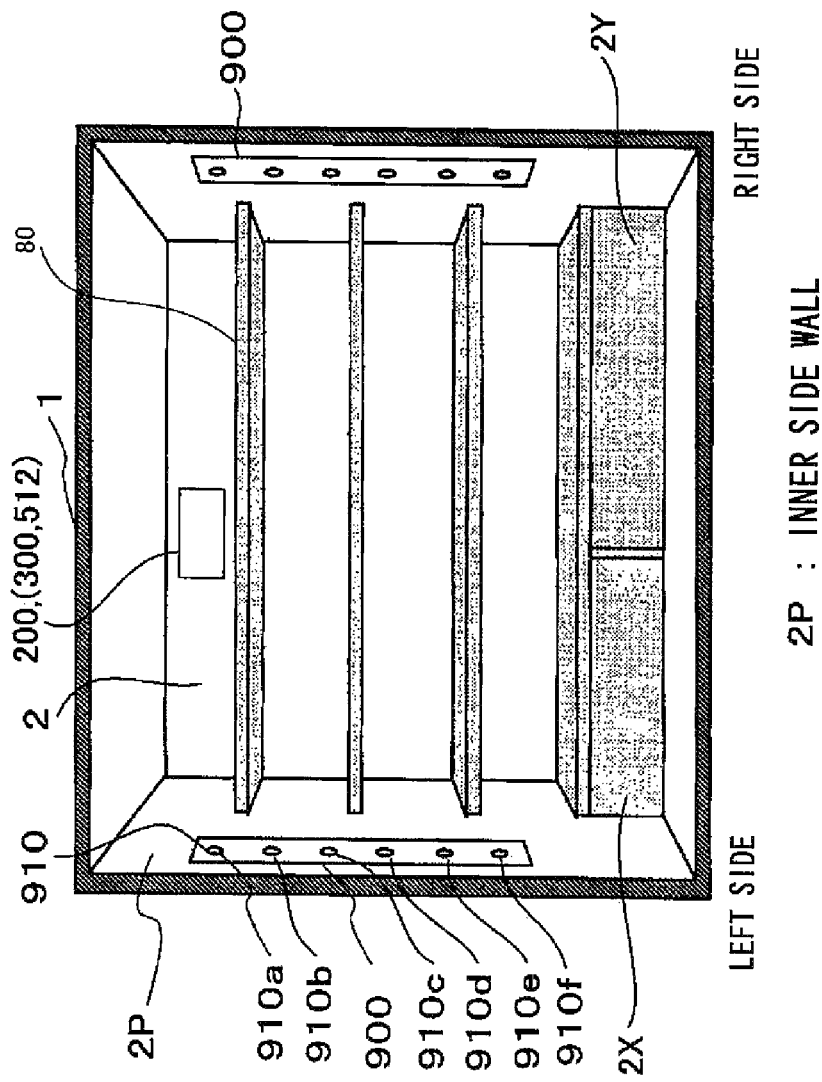
FIG. 22 is a front perspective view of a refrigerating compartment of the refrigerator describing the embodiment of the present invention.

FIG. 22 is a front perspective view of the refrigerator 1 describing the embodiment of the present invention. As shown in FIG. 22, the lighting device 900 using as a light source the plural LEDs 910 that emit visible light for making it possible for a user to visually confirm stored items, for example, white light, etc. is provided in the side portion (hereinafter referred to as an inner side wall 2P) of the inner wall of the refrigerating compartment 2. In the present embodiment, the lighting device 900 is provided in a position forward (nearer to the refrigerating compartment door 7) of the anterior edges of the inside refrigerator shelves 80 in the inner side wall 2P so that lights emitted by the LEDs 910 in the lighting device 900 are not hidden by a stored item even in a case wherein the stored item is housed on the inside refrigerator shelve 80. Further, as for the vertical direction, the plural LEDs 910 included in the lighting device 900 are allocated so as to be placed approximately in between two inside refrigerator shelves 80 next to each other among the plural inside refrigerator shelves 80 so that the lights emitted by the LEDs 910 in the lighting device 900 are less subject to the inside refrigerator shelves 80.

Figure 23:
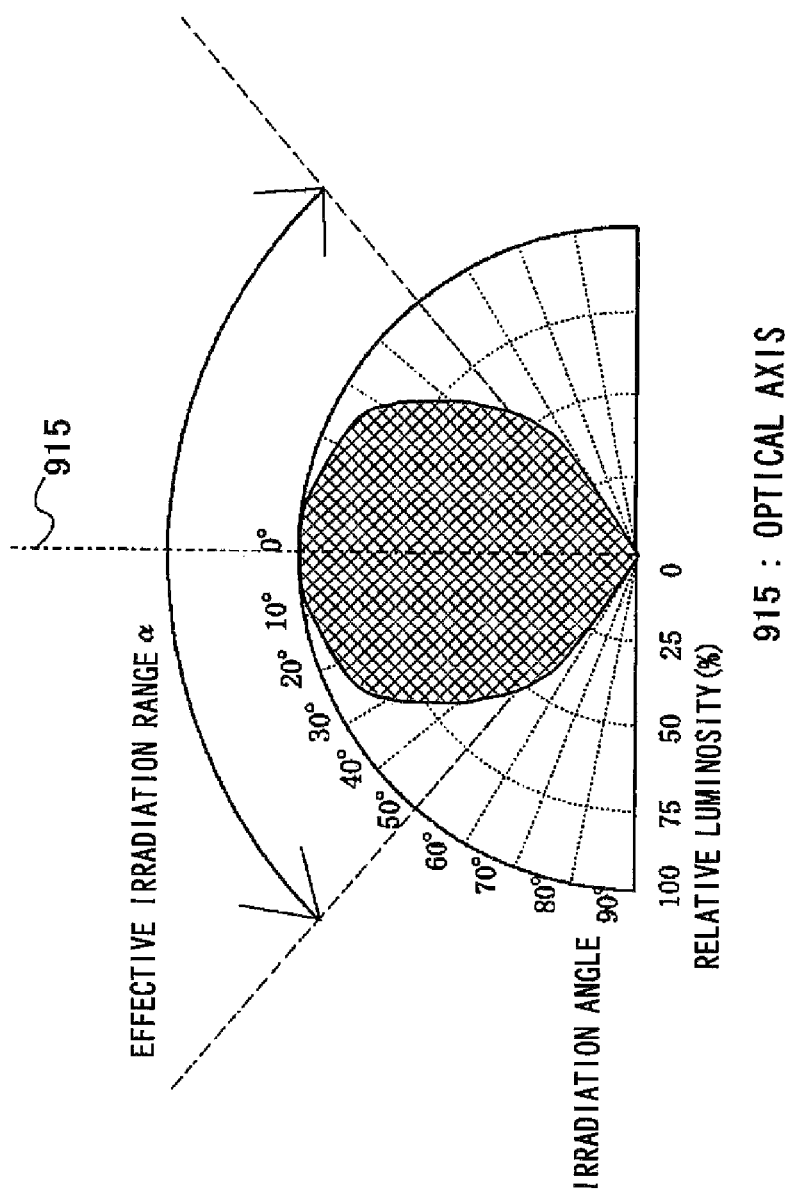
FIG. 23 is a diagram describing a light-emitting characteristic of a general LED 910.

FIG. 23 is a diagram describing a light-emitting characteristic of the general LEDs 910. As shown in the diagram, the LEDs 910 generally have strong light directivity regarding luminescence. Therefore, luminosity is the highest in a direction of an optical axis 915 perpendicular to a light-emitting plane of the LEDs 910, and luminosity decreases with distance from the optical axis 915. Here, for example, a range where light is radiated with luminosity equal to or more than 50% of the luminosity at the optical axis 915 is referred to as an effective irradiation range α (however, it does not mean that light cannot be radiated at all to a part other than in the effective irradiation range α by the lights emitted by the LEDs 910, but it means a range that predetermined luminosity cannot be obtained other than in the range of the effective irradiation range α by the lights emitted by the LEDs 910). In the diagram, it is described a case wherein when the optical axis 915 is set 0°, α=100° (approximately) ±50° is included in the effective irradiation range α. Further, if not otherwise specified, the directions of lights regarding luminescence of the LEDs 910 are to be described hereinafter as directions in a plane parallel to the inside refrigerator shelves 80 (this does not especially limit light in vertical direction).

In the present embodiment, at least one of the plural LEDs 910 (the LED 910*a*, the LED 910*b*, the LED 910*c*, the LED 910*d*, the LED 910*e* and the LED 910*f*) is used as the electrostatic atomizing apparatus light 600 for the electrostatic atomizing apparatus 200. For example, when the refrigerating compartment door 7 is open, since the plural LEDs 910 in the lighting device 900 are all used as the lighting inside the refrigerator, the plural LEDs 910 may be lighted in white, for instance, and when the electrostatic atomizing apparatus 200 operates during opening of the refrigerating compartment door 7, at least one LED (for example, the 910*a*) of the plural LEDs in the inside lighting device 900 may be made to flash or light off.

Of course, it is also applicable that a color (for example, blue, red, orange, or yellow, etc.) of an LED that is lit up during operation of the electrostatic atomizing apparatus 200 and a color (for example, white) of an LED that is lit up for lighting inside the refrigerator are different colors, which can be simply recognized by a user visually. Further, it is also applicable to change the color of the LED to be used for the lighting inside the refrigerator and have the LED flashes. Additionally, it is also applicable to have the plural LEDs lit during operation of the electrostatic atomizing apparatus 200, and have the colors of the plural LEDs changed, or to have the LEDs with different colors flash alternately, in order to notify the user immediately.

Here, when the color of the LED that is lit up during operation of the electrostatic atomizing apparatus 200 and the color of the LED for the lighting inside the refrigerator are different colors, the LED that is lit up during operation of the electrostatic atomizing apparatus 200 is lit up only during operation of the electrostatic atomizing apparatus 200, and is lit off when the electrostatic atomizing apparatus 200 is not operating. Further, it is applicable that by using an LED which can emit lights in two colors (the first color and the second color), a light in white color, for example, as the first color is turned on when the electrostatic atomizing apparatus 200 is not operating, and a light in the second color (for example, a color different from the first color, such as red, blue, green, yellow, orange, etc.) is turned on during operation of the electrostatic atomizing apparatus 200. In this way, since it is possible to use the LED to be lit during operation of the electrostatic atomizing apparatus 200 as the lighting inside the refrigerator even when the electrostatic atomizing apparatus 200 is not operating, when the refrigerating compartment door 7 of the refrigerating compartment 2 is open, all the plural LEDs in the lighting device 900 can be used as the lighting inside the refrigerator, and brightness is not decreased in the refrigerator. Furthermore, since it is possible to have the light lit in the color (the second color, for example, red, blue, green, yellow, or orange, etc.) different from the color (the first color, for example, white) to be used as the lighting inside the refrigerator when the electrostatic atomizing apparatus 200 is operating, anyone can visually confirm that the electrostatic atomizing apparatus 200 is operating, and the design is also improved.

Figure 24:
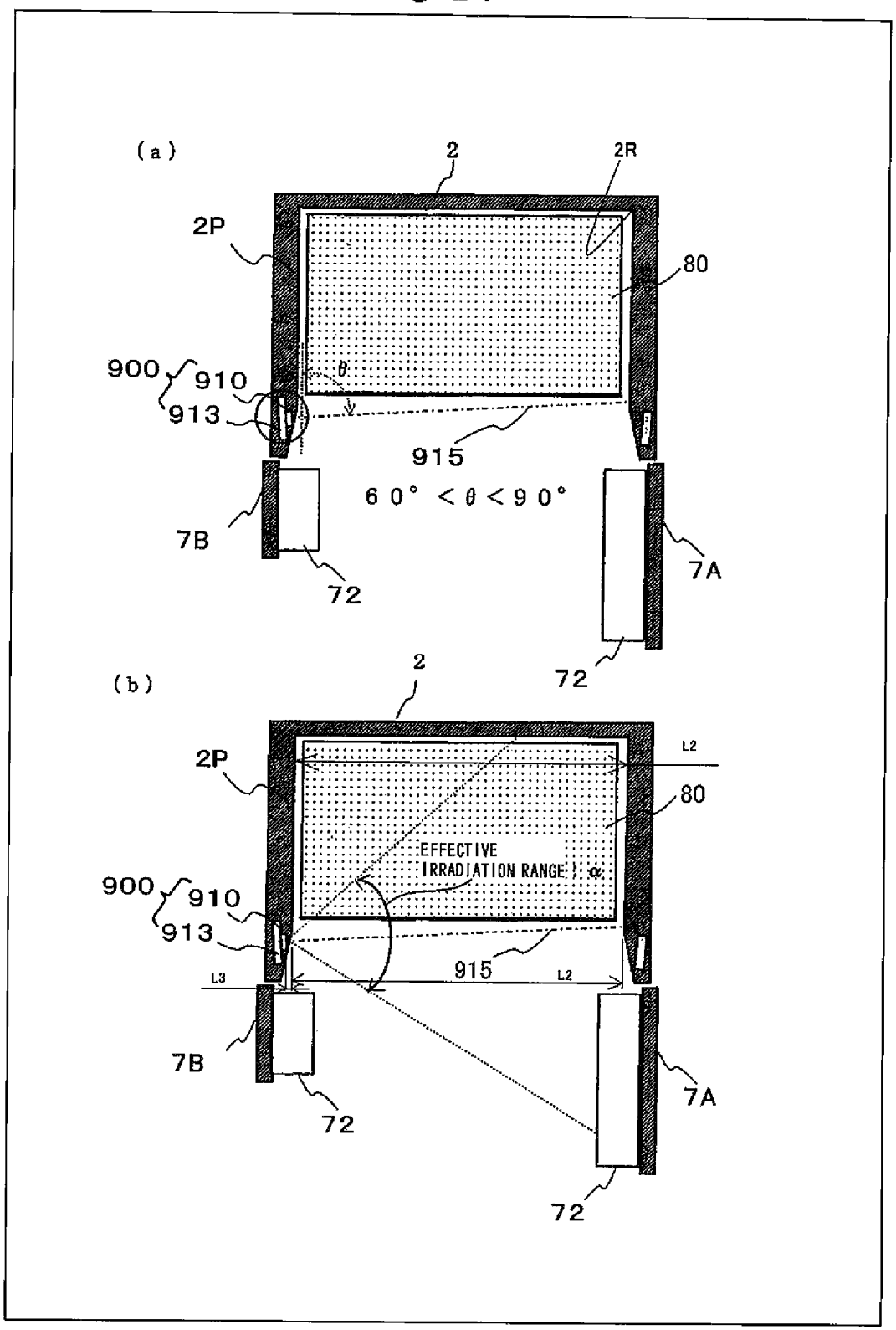
FIG. 24 is a diagram of a refrigerating compartment 2, viewed from a superior view, of the refrigerator 1 describing the embodiment of the present invention.

FIG. 24 is a diagram of the refrigerating compartment 2 of the refrigerator 1 from a superior view describing the embodiment of the present invention. As described above, the refrigerating compartment door 7 is provided in the front surface of the refrigerating compartment 2. In the refrigerator 1 in the present embodiment, the left refrigerating compartment door 7A and the right refrigerating compartment door 7B for opening and shielding the space in the refrigerating compartment 2 to and against the outside by opening and closing in a side-by-side manner, each of which is connected to the main body of the refrigerator 1 with a hinge (not shown in the diagrams), are provided in the front surface of the refrigerating compartment 2. Here, the door on the right side to the refrigerator 1 is the right refrigerating compartment door 7B, and the door on the left side is the left refrigerating compartment door 7A (described as the refrigerating compartment door 7 in a case wherein no particular distinction is necessary).

Further, a door pocket 72 for housing a food item is included inside the refrigerating compartment door 7. Furthermore, the lighting device 900 is formed by attaching the plural LEDs to a printed substrate 913 made of an electrical circuit. However, the part of the printed substrate 913 is made not to be exposed to the inside of the refrigerating compartment 2 so as to present a pleasing appearance, and prevent reduction of the inner volume.

In the present embodiment, by assuming a distance (length) from an approximate center of the LEDs 910 to the anterior edges of the inside refrigerator shelves 80 placed on the storage compartment (for example, the refrigerating compartment 2) as L1 as shown in FIG. 21, and as shown in FIG. 24, by assuming a distance (length) of a horizontal width (in between the inner side walls 2P) of a storage compartment (for example, the refrigerating compartment 2) of the refrigerator 1 as L2, a distance (length) from the approximate center of the LEDs 910 to the inner side wall 2P of the storage compartment (for example, the refrigerating compartment 2) as L3, and a distance from the anterior edge of the placed inside refrigerator shelf 80 to the rear wall of the storage compartment (for example, the refrigerating compartment 2) as L4, in the present embodiment, the LEDs 910 are arranged to form an angle θ between the optical axis 915 of the LEDs 910 and the inner side wall 2P to be $\tan^{-1}((L2+L3)/L1)) < \theta < 90°$, so that the LEDs 910 and the optical axis 915 of the LEDs 910 are arranged in such directions (for example, such directions that the optical axis 915 of the LEDs 910 does not directly fall on the anterior edge portions of the inside refrigerator shelves 80) that lights in the direction of the optical axis 915 of the LEDs 910 do not enter the inside refrigerator shelves 80 (especially, the anterior edge portions) directly, and a user is not subject to glare. Here, $\tan^{-1}$ represents arc tangent.

Now, since it is L2>>L3 (L2 is sufficiently greater than L3), it can be considered that L2+L3≈L2 ((L2+L3) is approximately the same as L2); hence, it is also applicable to arrange the optical axis 915 of the LEDs 910 by assuming $\tan^{-1}((L2+L3)/L1))$ as $\tan^{-1}(L2/L1)$. Therefore, by consideration as mentioned above, it is also applicable to arrange the LEDs 910 and the optical axis 915 of the LEDs 910 in such directions (for example, such directions that the optical axis 915 of the LEDs 910 does not directly fall on the anterior edge portions of the inside refrigerator shelves 80) that lights in the direction of the optical axes 915 of the LEDs 910 do not enter the inside refrigerator shelves 80 (especially the anterior edge portions) directly, by setting the angle θ between the optical axis 915 of the LED 910 and the inner side wall 2P to be $\tan^{-1}(L2/L1)) < \theta < 90°$.

In (a) of FIG. 24, the angle θ formed between the optical axis 915 of the LEDs 910 and the inner side wall 2P is set an angle larger than $\tan^{-1}((L2+L3)/L1))$, for example, θ is set an angle larger than 70 degrees, and the lighting device 900 is attached so that the optical axis 915 of the LEDs 910 is directed to such a direction (for example, such a direction that the optical axis 915 of the LEDs 910 does not directly fall on the anterior edge portions of the inside refrigerator shelves 80) that lights in the direction of the optical axis 915 of the LEDs 910 do not enter the inside refrigerator shelves 80 (especially the anterior edge portions) directly, thereby the lights do not directly fall on the anterior edge portions of the inside refrigerator shelves 80 and a user is not subject to glare by reflected light.

By setting the angle θ larger than $\tan^{-1}((L2+L3)/L1))$, for example, an angle larger than 70 degrees, well-balanced irradiation without ununiformity, etc. can be performed when the entire inside refrigerator shelves 80 are irradiated. Now, for example, if lights in the direction of the optical axis 915 enter the inside refrigerator shelves 80 even when the angle θ is set equal to or larger than 70 degrees, it is desirable to basically treat it as a priority in arrangement that the lights in the direction of the optical axis 915 are directed in a direction not to enter the inside refrigerator shelves 80 directly unless there is a reason that a user is not subject to glare by reflected light and so on. Further, although the upper limit of the angle θ is not limited, since the LEDs 910 are mainly for lighting up inside of the refrigerating compartment 2, the angle θ formed between the optical axis 915 of the LEDs and the inner side wall 2P should preferably be smaller than 90 degrees and directed to the inside of the refrigerator, because if the angle θ is equal to or larger than 90 degrees, the optical axis 915 is not directed to the inside of the refrigerator 1 but to the outside of the refrigerator, and there is a possibility that the optical axis 915 does not irradiate inside the refrigerator 1. That is, the angle θ formed between the optical axis 915 of the LEDs and the inner side wall 2P should preferably be larger than 70 degrees but smaller than 90 degrees (that is, it is preferable that $70° < \theta < 90°$). However, since the LEDs 910 can irradiate the inside of the refrigerator within the range of the effective irradiation range α, when assuming the effective irradiation range α as, for example, α=100 degrees (±50 degrees with respect to the optical axis 915), the inside of the refrigerator can be illuminated, and further, a user is not subject to glare when the arranged angle θ of the optical axis 915 is within the range of $\tan^{-1}((L2+L3)/L1)) < \theta < 90° \pm \alpha/2$.

However, when the installation position of the lighting device 900 to the inner side wall 2P is provided nearer to the inside of the refrigerator than the anterior edges of the inside refrigerator shelves 80 (for example, when L3 is minus), since lights in the direction of the optical axis 915 do not fall on the anterior edges of the inside refrigerator shelves 80 directly even when the angle θ formed between the optical axis 915 of the LEDs and the inner side wall 2P is equal to or lower than $\tan^{-1}((L2+L3)/L1))$, for example, θ is equal to or lower than 70 degrees, there is no possibility that the lights fall on the anterior edges of the inside refrigerator shelves 80 directly and a user is subject to glare by installing the lighting device 900. Therefore, in this case, by setting the optical axis 915 as θ=approximately 70 degrees, and the effective irradiation range a of the LEDs 910 as, for example, approximately 100 degrees (±approximately 50 degrees), the range irradiate by lights of the LEDs 910 in the lighting device 900 is $-\alpha/2+\theta<$irradiation range$<\theta+\alpha/2$ with respect to the inner side wall 2P, and the irradiation range is within a range from 20 degrees to 120 degrees, hence it becomes possible to irradiate evenly almost all the area inside the refrigerator.

Further, it will be described a case wherein the installation position of the lighting device 900 to the inner side wall 2P is on the front side to the anterior edges of the inside refrigerator shelves 80 (for example, when L3 is plus), and further, the angle $\theta$ formed between the optical axis 915 of the LEDs and the inner side wall 2P is equal to or lower than $\text{Tan}^{-1}((L2+L3)/L1))$, for example, is equal to or lower than 70 degrees. FIG. 25 is a top view of the refrigerating compartment 2 of the alternative refrigerator according to the embodiment 1 of the present invention. In the refrigerator 1, it is described a case wherein the angle $\theta$ formed between the optical axis 915 of the LEDs 910 and the inner side wall 2P is equal to or lower than $\text{Tan}^{-1}((L2+L3)/L1))$, and lights in the direction of the optical axis 915 of the LEDs are directed to the direction of the inside refrigerator shelf 80. In the refrigerator 1 as shown in the diagram, since the angle $\theta$ between the LEDs and the inner side wall 2P is set equal to or lower than $\text{Tan}^{-1}((L2+L3)/L1))$, and the lights in the direction of the optical axis 915 of the LEDs are directed to the direction of the inside refrigerator shelf 80, the lights are likely to be radiated to the rear side (the back side) of the refrigerating compartment 2 in a concentrated manner. Therefore, although inside of the refrigerating compartment 2 can be illuminated brightly, the lights in the direction of the optical axis 915 by the LEDs 910 fall on the inside refrigerator shelf 80 directly, which may cause the reflected light by the anterior edge of the inside refrigerator shelf 80 enter the eyes of the user of the refrigerator 1 strongly, and cause the user to be subject to glare.

In this case, it is also applicable that by using a material less likely to reflect light for the anterior edges of the inside refrigerator shelves 80, or by forming a coating film over or forming into a shape the anterior edges of the inside refrigerator shelves 80 that is less likely to reflect light (for example, mattes coating, coating in a color less likely to reflect light, or a shape whereby reflected light is not directed to a front direction but is directed to a lateral direction inside the refrigerator by processing the surface to be indented, etc.), the user is not subject to glare even when the light is reflected. Therefore, in the refrigerator 1 according to the present embodiment, even when the angle $\theta$ between the LEDs 910 and the inner side wall 2P is set equal to or lower than (for example, equal to or lower than 70 degrees) $\text{Tan}^{-1}((L2+L3)/L1))$, the lights emitted in the direction of the optical axis 915 of the LEDs 910 enter the inside refrigerator shelves 80 directly, glare by reflection can be reduced, and almost all the area in the refrigerator can be evenly illuminated brightly, and it is possible to provide the refrigerator 1 which is eye-friendly, having a small effect on the eyes of the user, and a stored item therein can be visually confirmed at once also in the night.

Now, as described above, the LEDs 910, which is light sources of the lighting device 900, has strong directivity, whereby lights are strongly irradiated within the effective irradiation range $\alpha$ centering on the optical axis 915. Here, when the angle $\theta$ the direction of the optical axis 915 of the LEDs 910 forms with respect to the inner side wall 2P is changed, the effective irradiation range $\alpha$ also changes simultaneously. In the refrigerator 1 shown in FIG. 25, since the angle $\theta$ the optical axis 915 of the LEDs 910 forms with respect to the inner side wall 2P is set equal to or lower than (for example, equal to or lower than 70 degrees) $\text{Tan}^{-1}((L2+L3)/L1))$, and inside of the refrigerating compartment 2 is irradiated in a concentrated manner, there is a possibility that the inner side of the opened refrigerating compartment door 7 that is in a state opened approximately 90 degrees from a closed state of the refrigerating compartment door 7 is not included in the effective irradiation range $\alpha$ of the LEDs 910, and hence a few light is irradiated over the door pocket 72 provided inner side of the refrigerating compartment door 7 by the LEDs 910, and the door pocket 72 may be underlit. Since the door pocket 72 is a housing space greatly convenient for housing and taking out a beverage, small items, etc., it is preferable to have the door pocket 72 in the state of the refrigerating compartment door 7 opening approximately 90 degrees illuminated in consideration of convenience of a user in such a case wherein the surrounding part of the refrigerator 1 is dark, especially at night; therefore, the installation angle of the optical axis 915 should preferably be set by considering the effective irradiation range $\alpha$.

Meantime, the angle $\theta$ the optical axis 915 of the LEDs 910 forms should be set at a degree capable of illuminating the door pocket 72 of the refrigerating compartment door 7 in an open state approximately 90 degrees from a closed state, by setting the angle $\theta$ the optical axis 915 of the LEDs 910 forms with respect to the inner side wall 2P larger than $\text{Tan}^{-1}((L2+L3)/L1)$ (for example, equal to or lower than 70 degrees), and so on in consideration of the effective irradiation range $\alpha$.

Therefore, in the refrigerator 1 as shown in FIG. 24, the angle $\theta$ the optical axis 915 of the LEDs 910 forms with respect to the inner side wall 2P is set an angle (for example, approximately 75 degrees) larger than $\text{Tan}^{-1}((L2+L3)/L1)$, and the door pocket 72 in the state wherein the refrigerating compartment door 7 is opened approximately 90 degrees from the closed state is included in (an extension of) the effective irradiation range $\alpha$. Thus, the LEDs 910 can also irradiate the door pocket 72 at the same time while irradiating inside of the refrigerating compartment 2, and the refrigerator 1 which is user-friendly capable of providing both lighting over the inside of the refrigerator 1 and lighting over the door pocket 72 also at night can be obtained. Further, a user can also recognize at once that the electrostatic atomizing apparatus 200 is operating by making the LEDs 910 of the lighting device 900 light and flash.

Here, when the angle $\theta$ the optical axis 915 of the LEDs 910 forms with respect to the inner side wall 2P is $\text{Tan}^{-1}((L2+L3)/!(L1+L4))$, since the optical axis 915 is directed to a direction of a corner part position 2R (a rear side angle position, or a rear side corner position in a storage compartment) where the inner side wall 2P opposed to the inner side wall 2P whereto the LEDs 910 are installed intersects with the rear wall when $\theta$ is approximately 60 degrees in a general refrigerator, it is possible to irradiate all over the inside of the storage compartment the most efficiently when $\theta$ is approximately 60 degrees. Therefore, with respect to lighting inside the refrigerator, a case wherein $\theta$ is $\text{Tan}^{-1}((L2+L3)/(L1+L4))$ (for example, approximately 60 degrees) is preferable.

Here, since it is L4>>L1 (L4 is sufficiently larger than L1), it can be considered that L1+L4$\approx$L4 ((L1+L4) is approximately the same as L4), it is possible to arrange the optical axis 915 of the LEDs 910 by considering $\text{Tan}^{-1}((L2+L3)/(L1+L4))$ as $\text{Tan}^{-1}(L2/L4)$. When $\theta$ is equal to or lower than $\text{Tan}^{-1}((L2+L3)/(L1+L4))$ (for example, equal to or lower than approximately 60 degrees), there is a possibility that the lights emitted from the LEDs 910 are reflected by the anterior edges of the inside refrigerator shelves 80 and a user is subject to glare, as mentioned above, whereas when $\theta$ is approximately not less than 30 degrees and not more than 60 degrees, a direction of the reflection is not in a direction that makes a user who is looking into the refrigerator standing on the front side of the refrigerator 1 be subject to glare, hence it is considered there is a small possibility that the user is subject to glare and feels it difficult to use. In addition, when there is a possibility that the user is subject to glare, it is preferable to provide a member of a material that softens reflected light, or a member that absorbs light and weakens reflected light, etc. in the anterior edges of the inside refrigerator shelves 80.

In this case, the angle θ the optical axis 915 of the LEDs 910 forms with respect to the inner side wall 2P should preferably be approximately $\text{Tan}^{-1}((L2+L3)/(L1+L4))$ in view of the effective irradiation range α of the LEDs 910. However, when the formed angle θ is approximately $\text{Tan}^{-1}((L2+L3)/(L1+L4))$, since there is a possibility that light is reflected by the anterior edges of the inside refrigerator shelves 80 and a user is subject to glare, and further, the door pocket 72 in a state wherein the refrigerating compartment door 7 is opened approximately 90 degrees from the closed state is less likely to be irradiated, it is preferable to set θ within a range of approximately $\text{Tan}^{-1}((L2+L3)/(L1+L4)) < θ < 90$ degrees; however, when θ is close to 90 degrees, in view of the effective irradiation range α, when assuming that θ is approximately 90 degrees, for example, and the effective irradiation range α is 100 degrees (±50 degrees with respect to the optical axis 915), for example, the irradiation range becomes a range between 40 degrees to 150 degrees, and when the irradiation range is 150 degrees, there is a possibility that one who is using the refrigerator 1 (user) is subject to glare; therefore, it is more preferable to set θ to be within a range of approximately $\text{Tan}^{-1}((L2+L3)/(L1+L4)) < θ <$ approximately $\text{Tan}^{-1}((L2+L3)/L1)$, since the user is not subject to glare in view of the effective irradiation range α, and it is possible to irradiate a large area in the refrigerator.

According to the present embodiment as described above, since the LEDs 910 are used for the lighting inside the refrigerator, the refrigerator 1 of low power consumption and energy saving, wherein an amount of heat generation is small can be obtained. Further, since at least one of the plural LEDs 910 used for the lighting inside the refrigerator can be made to flash during operation of the electrostatic atomizing apparatus 200, or to light in another color different from the emitted color used for lighting, it is not necessary to additionally provide a lighting device for the electrostatic atomizing apparatus 200, and further, by making at least one of the plural LEDs 910 light in the other color, the design is improved, and a user can visually confirm that the electrostatic atomizing apparatus 200 is operating at once.

Further, when the LEDs 910 are used for lighting, since the lighting device 900 whereto the plural LEDs 910 are arranged in a vertical direction is provided in a position nearer to the front side (the refrigerating compartment door 7 side) than the anterior edges of the inside refrigerator shelves 80 on each of the right and left inner side walls 2P inside the refrigerating compartment 2 of the refrigerator 1, the angle θ formed between the optical axis 915 of the light emitted by each of the LEDs 910 and the inner side wall 2P is set larger than approximately $\text{Tan}^{-1}(L2+L3)/L1)$ (for example, approximately 70 degrees) and smaller than approximately 90 degrees, and further, lights in the direction of the optical axis 915 are made not to directly enter the inside refrigerator shelves 80, the lights in the direction of the optical axis 915 of the LEDs 910 do not fall on the anterior edges of the inside refrigerator shelves 80 directly, glare that a user is subject to is reduced, and high visibility is ensured in the refrigerating compartment 2. Further, when the angle θ formed between the optical axis 915 of the light emitted by each of the LEDs 910 and the inner side wall 2P is set larger than approximately $\text{Tan}^{-1}(L2+L3)/L1)$ (for example, approximately 70 degrees), and the lighting devices 900 are installed in a manner so as not to be inclined too much to the back (rear side) of the inside of the refrigerating compartment 2, even when the front side of the refrigerating compartment 2, that is, the refrigerating compartment door 7 is in an open state, the door pocket 72 formed in the refrigerator compartment door 7 can also be irradiated; therefore, a lighting device dedicated to lighting of the door pocket 72, for example, needs not be provided, which contributes to cost reduction and energy saving.

Furthermore, even when the angle θ formed between the LEDs 910 and the inner side wall 2P is set equal to or smaller than approximately $\text{Tan}^{-1}(L2+L3)/L1)$ (for example, approximately 70 degrees), and the lights emitted in the direction of the optical axis 915 of the LEDs 910 are made to enter the inside refrigerator shelves 80 directly, in a case wherein reflected light does not directly fall on a user in front of the refrigerator 1 and the user is less likely to be subject to glare due to shallow angle of incident light to the anterior edges of the inside refrigerator shelves 80, the user does not feel glare by the reflected light due to reflection, and further, almost all the area in the refrigerator can be evenly and brightly illuminated; therefore, it is possible to provide the refrigerator 1, which has small influence on the eyes of the user, a stored item in which can be confirmed immediately also at night, and which is eye-friendly.

Further, also in a case wherein the user feels glare when the lights emitted in the direction of the optical axis 915 of the LEDs 910 are made to enter the inside refrigerator shelves 80 directly, by using a material less likely to reflect light over the anterior edges of the inside refrigerator shelves 80, or by forming a coating film over or forming into a shape (for example, mattes coating, coating in a color less likely to reflect light, or a shape whereby reflected light is not directed to a front direction but is directed to a lateral direction inside the refrigerator by processing the surface to be indented) the anterior edges of the inside refrigerator shelves 80 that is less likely to reflect light, glare due to reflection can be lessened similarly, and further, almost all the area in the refrigerator can be evenly and brightly illuminated; therefore, it is possible to provide the refrigerator 1, which has small influence on the eyes of the user, a stored item in which can be confirmed immediately also at night, and which is eye-friendly.

Here, plural LEDs (for example, the LED 910a to the LED 910o) of the lighting device 900 inside the refrigerator are lit up when an opening and closing door (for example, the refrigerating compartment door 7) of a storage compartment (for example, the refrigerating compartment 2) is open, in which case at least one (for example, the LED 910a) of the plural LEDs (for example, the LED 910a to the LED 910f) is used for displaying that the electrostatic atomizing apparatus 200 is operating, it is applicable that at least one LED, for example, the LED 910a, is made to flash or be turned off when the opening and closing door (for example, the refrigerating compartment door 7) of the storage compartment (for example, the refrigerating compartment 2) is open. Alternatively, it is also applicable that at least one LED (for example, the LED 910a) is made up of two or more LEDs in different colors (for example, in white and orange), which is lit up in a same type of color (for example, white) as a lighting color of the inside refrigerator lighting device 900 when the electrostatic atomizing apparatus 200 is not operating, and which is lit up in a different color (for example, in a different type of color, and for example, orange) from the lighting color of the lighting device 900 inside the refrigerator when the electrostatic atomizing apparatus 200 is operating.

Further, it is also applicable that when two or more LEDs (for example, the LED 910a and the LED 910b) are lit up when the electrostatic atomizing apparatus 200 is operating, these two or more LEDs (for example, the LED 910a and the LED 910b) are in different colors (for example, blue, orange, or red, etc.) from the lighting color (for example, white) of the inside refrigerator lighting device 900, wherein at least two or more LEDs (for example, the LED 910a and the LED 910b) are lit up in a same type of colors (for example, white) as a lighting color of the inside refrigerator lighting device 900 when the electrostatic atomizing apparatus 200 is not operating, which are lit up in different colors (for example, in different types of colors, such as blue, orange, red, etc.) from the lighting color of the inside refrigerator lighting device 900 when the electrostatic atomizing apparatus 200 is operating.

Additionally, these at least two or more LEDs may be different colors, and may be the same colors. Further, it is also applicable to have two or more LEDs be lit up and switched off alternately while the electrostatic atomizing apparatus 200 is operating. In this way, design is improved and a user can immediately confirm that the electrostatic atomizing apparatus 200 is operating at the same time, and further, since the LEDs can be also used as the lighting inside the refrigerator, the refrigerator 1 low in cost can be obtained. Furthermore, it is also applicable to use a plural colors emitting LED that is capable of emitting lights in two and more different colors for at least one or more LEDs (for example, the LED 910a, the LED 910b). Additionally, at least one (for example, the LED 910f) of the plural LEDs 910 in the inside refrigerator lighting device 900 can be used as a dedicated LED for representing that the electrostatic atomizing apparatus 200 is operating. In this case, it is also applicable to have the LED not to light up when the electrostatic atomizing apparatus 200 is not operating, and to have the LED light up in a different color (for example, orange, etc.) different from the lighting color (for example, white) of the inside refrigerator lighting device 900 only when the electrostatic atomizing apparatus 200 is operating.

Further, if it often happens that the electrostatic atomizing apparatus 200 is not operating at the time an opening and closing door (for example, the refrigerating compartment door 7) of a storage compartment (for example, the refrigerating compartment 2) is open, it is applicable to perform lighting control representing that the electrostatic atomizing apparatus 200 is operating when the electrostatic atomizing apparatus 200 is actuated within a predetermined time (for example, 60 minutes) after the opening and closing door (for example, the refrigerating compartment door 7) is opened. In this way, a user can recognize that the electrostatic atomizing apparatus 200 is operating even if the electrostatic atomizing apparatus 200 is not operating at the time the refrigerating compartment door 7 is opened. Further, it is also applicable to display also an operation result or an operation schedule (for example, how many minutes before the operation has been performed, how many minutes later the next operation is scheduled, and so on) of the electrostatic atomizing apparatus 200, not only the time the electrostatic atomizing apparatus 200 is operating on the control panel 60. In this way, even when the user does not stay near the refrigerator 1 while the electrostatic atomizing apparatus 200 is operating, the user can visually recognize an operation status of the electrostatic atomizing apparatus 200.

As mentioned above, the angle θ the optical axis 915 of the LEDs 910 forms with respect to the inner side wall 2P whereto the LEDs 910 are provided is set within the range of approximately $\mathrm{Tan}^{-1}((L2+L3)/(L1+L4))<\theta<$approximately $\mathrm{Tan}^{-1}((L2+L3)/L1)$, when the LEDs 910 are used for the lighting device 900 inside a storage compartment, and by assuming the distance from the approximate center of the LEDs 910 to the anterior edge of the inside refrigerator shelf 80 placed in the storage compartment (for example, the refrigerating compartment 2) as L1, the distance (the horizontal width of the storage compartment) in between the inner side wall surfaces (the inner side walls 2P) of the storage compartment as L2, the distance from the approximate center of the LEDs 910 to the inner side wall 2P whereto the LEDs of the storage compartment are provided as L3, and the distance from the anterior edge of the inside refrigerator shelf 80 to the rear wall of the storage compartment as L4, a user is not subject to glare, the inside of the refrigerator can be easily viewed since it is possible to irradiate a wide area inside the refrigerator, and further, by using at least one of the lighting devices 900 in the storage compartment (inside the refrigerator) as the electrostatic atomizing apparatus light 600, it is possible to visually confirm whether the electrostatic atomizing apparatus 200 (the mist spraying apparatus) is operating at once by the lighting device 900 inside the storage compartment (inside the refrigerator). Further, in view of the effective irradiation range α, since it is possible to irradiate the door pocket 72 as well even when the door is opened, a housed item inside the door pocket 72 can be visually confirmed also at night.

Furthermore, even when the angle θ the optical axis 915 of the LEDs 910 forms with respect to the inner side wall 2P whereto the LEDs 910 are provided is set within the range of approximately $\mathrm{Tan}^{-1}((L2+L3)/(L1+L4))<\theta<$approximately 90 degrees, a user is not subject to glare, and in view of the effective irradiation range α, since it is possible to irradiate a wide area inside the refrigerator, the inside of the refrigerator can be easily viewed, and further, by using at least one of the lighting devices 900 in the storage compartment (inside the refrigerator) as the electrostatic atomizing apparatus light 600, it is possible to visually confirm whether the electrostatic atomizing apparatus 200 (the mist spraying apparatus) is operating at once by the lighting device 900 in the storage compartment (inside the refrigerator). Further, since it is possible to irradiate the door pocket 72 as well even when the door is opened, a housed item inside the door pocket 72 can be visually confirmed also at night.

Further, when the angle θ the optical axis 915 of the LEDs 910 forms with respect to the inner side wall 2P whereto the LEDs 910 are provided is set within the range of approximately $\mathrm{Tan}^{-1}((L2+L3)/L1)<\theta<$approximately 90 degrees, since the optical axis 915 of the LEDs 910 does not fall on the anterior edges of the inside refrigerator shelves 80 directly, a user is not subject to glare, and in view of the effective irradiation range α, since it is possible to irradiate a wide area inside the refrigerator, the inside of the refrigerator can be easily viewed, and further, by using at least one of the lighting devices 900 in the storage compartment (inside the refrigerator) as the electrostatic atomizing apparatus light 600, it is possible to visually confirm whether the electrostatic atomizing apparatus 200 (the mist spraying apparatus) is operating at once by the lighting device 900 inside the storage compartment (inside the refrigerator). Further, since it is possible to irradiate the door pocket 72 as well even when the door is opened, a housed item inside the door pocket 72 can be visually confirmed also at night.

(An Alternative Use of the Electrostatic Atomizing Apparatus Light)

Further, by using an LED (for example, the LED 910a) in blue or purple, which emits a light of a wavelength within a range of 360 nm to 400 nm with a peak of 375 nm in the UV-A wavelength range, for example, for an LED (for example, the LED 910*a*) representing that the electrostatic atomizing apparatus light 600, the lighting device 900 inside of the storage compartment (inside the refrigerator), or the electrostatic atomizing apparatus 200 is operating, and by illuminating inside of the refrigerator only for a predetermined time, for example, while the door of the refrigerator 1 is closed, it is possible to increase vitamin in vegetables, etc. without affect on the human body. Additionally, by using an LED in high-intensity orange with warmth, which emits a light of a wavelength within a range of 550 nm to 620 nm with a peak of 590 nm, for example, is used for the LED (for example, the LED 910*a*) representing that the electrostatic atomizing apparatus light 600, the lighting device 900 inside the storage compartment (inside the refrigerator), or the electrostatic atomizing apparatus 200 is operating, and by illuminating inside of the refrigerator only for a predetermined time, for example, while the door of the refrigerator 1 is closed, the LED can be used as the lighting inside the refrigerator with warmth which does not affect the human body, and can be also used for stimulating a self defense function mainly of green and yellow vegetables and for activating biosynthesis of polyphenol, and further, can be used for stimulating biosynthesis of vitamin C by photosynthesis as well. Thus, although the effect can be obtained also in the refrigerating compartment 2 or the switching compartment 4, etc., further effect can be obtained by application to the vegetable compartment 5.

A plant grows basically through photosynthesis, and in addition, photomorphogenesis as a qualitative transformation of the plant such as seed germination, flower bud differentiation, anthesis, cotyledon expansion, chlorophyll synthesis, internode elongation, etc. is performed, and nutrient elements reserved at the time is used as a source of energy. Among them, photomorphogenesis that is inappropriate for vegetable preservation such as germination, anthesis, etc. is apt to be stimulated by blue light at around 470 nm, and red light at around 660 nm. Since the lights cast from the LED of the electrostatic atomizing apparatus light 600 and the LEDs 910 of the lighting device 900 inside the storage compartment (inside the refrigerator) are of wavelengths within a range of 320 to 400 nm which stimulate a self defense function of green and yellow vegetables and activate biosynthesis of polyphenol, the lights do not lower preservation quality of vegetables. Further, as for anthocyanin of a blueberry or a strawberry, etc., nutrient elements are increased by the LEDs 910, which are sources of lights of wavelengths having greenish-yellow color, etc.

Polyphenol is a collective term of chemical compounds whereof the benzene ring is substituted with plural hydroxyl groups or plural methoxy groups, included in a crop such as a vegetable, a fruit, a tea, etc. So-called flavonoids in the polyphenol are included especially in portions of a plant that are exposed to much sunlight. It is considered that this is because the plant synthesizes flavonoids exhibiting a strong maximum absorption in a range of ultraviolet in order for self protection against ultraviolet included in the sunlight. A main physiological effect of polyphenol is antioxidant effect and protein function regulating effect. Thus, aging is deterred by antioxidation, and in addition, cancer, arteriosclerosis, diabetes, cardiovascular disease, Alzheimer's disease, Parkinson's disease, amyloidosis, hepatitis, and cataract, etc. are alleviated.

Ultraviolet light is divided into the UV-A wavelength range (near ultraviolet, 320 to 400 nm), the UV-B wavelength range (middle ultraviolet, 280 to 320 nm), and the UV-C wavelength range (far ultraviolet, 100 to 280 nm). The shorter the wavelength is, the more harmful to the human body the ultraviolet light is, and there is a possibility that genetic fault is occurred when the ultraviolet is equal to or below 320 nm, that is, in the UV-B wavelength and the UV-C wavelength. Therefore, it is desirable to adopt an LED of a wavelength as long as possible in the near-ultraviolet of the UV-A wavelength range for a household refrigerator used by the general public. Of course, safety is improved doubly and triply by making the irradiation amount to an amount that does not affect on the human body, and the ultraviolet light not to be leaked structurally from the opening door.

That is, safety is improved by a simple structure without distinguishing the LED from the other light source, etc. in installation inside of the refrigerator 1 and so on. Of course, it is also possible to use a wavelength of middle ultraviolet range, etc., to irradiate the ultraviolet light only at the time the door of the refrigerator is closed, for example, and to structurally prevent leakage of irradiation to the door direction. In this case, a light of a wavelength that stimulates a self protection function of a plant is freely selected, but it is necessary to have only the light source arranged and constructed specially different from the other light sources. The LED of the electrostatic atomizing apparatus light 600 and the LEDs 910 in the lighting devices 900 inside the storage compartment (inside the refrigerator) stimulate a self defense function mainly of green and yellow vegetables, and activate biosynthesis of polyphenol. The LED of the electrostatic atomizing apparatus light 600 and the LEDs 910 in the lighting devices 900 inside the storage compartment (inside the refrigerator) are super luminosity LEDs emitting lights of wavelengths within a range of 550 nm to 620 nm with a peak of 590 nm, for example, which are used as the lighting inside the refrigerator, and further used for activating biosynthesis of vitamin C by photonic synthesis. These lights of the wavelengths may be used independently, or may be used in combination with a light of the other wavelength range.

(Application to a Return Air Trunk of the Electrostatic Atomizing Apparatus)

The above describes the case wherein the electrostatic atomizing apparatus 200 is installed inside the storage compartment, and condensation is occurred on the heat absorbing fin part 211 of the cooling plate 210 installed inside the storage compartment by temperature difference between the inside of the storage compartment and the inside of the cooling air trunk, thereby mist is sprayed; however, in a case wherein cooling inside the storage compartment (for example, the vegetable compartment 5) is performed by cool air that has cooled inside another storage compartment (for example, the refrigerator compartment 2) via a return air trunk, the electrostatic atomizing apparatus 200 needs not be provided in the storage compartment (for example, the vegetable compartment 5), and may be provided in the return air trunk from the other storage compartment (for example, the refrigerating compartment 2). In this case, a temperature of return cool air flowing inside the return air trunk rises after cooling the other storage compartment, and is higher than cooling cool air inside the cooling air trunk, and by providing the heat absorbing fin part 211 of the cooling plate 210 inside the return air trunk, and providing the heat dissipating fin part 212 inside the cooling air trunk, temperature difference can be used for the cooling plate 210; thus, it is possible to generate dew condensation water on the heat absorbing fin part 211, and mist can be generated inside the return air trunk. Therefore, the miniaturized nano-size mist generated inside the return air trunk reaches inside of the storage compartment (for example, the vegetable compartment 5) after flowing inside the return air trunk, thereby spraying of mist evenly in the storage compartment is possible.

In this way, since the electrostatic atomizing apparatus 200 needs not be installed inside the storage compartment, it is possible to increase the inner volume inside the storage compartment. Further, it is also applicable to make maintenance of the electrostatic atomizing apparatus 200 possible from the front side of the refrigerator 1. Maintenance of the electrostatic atomizing apparatus 200 is made possible by making at least a part of the partition wall 51 (the heat insulation wall) on the rear surface of a storage compartment (for example, the switching compartment 4 or the vegetable compartment 5, etc.) at a section wherein the electrostatic atomizing apparatus 200 is installed among the storage compartments (for example, the switching compartment 4 or the vegetable compartment 5, etc.) whereto the return air trunk from the other storage compartment (for example, the refrigerating compartment 2) to the storage compartment (for example, the vegetable compartment 5) is installed in the back side of the rear surface wall can be detached from the inner side of the storage compartment. Also in this case, maintenance and component replacement of the electrostatic atomizing apparatus 200 are made easy by forming the electrostatic atomizing apparatus 200 into a kit as the kit component 512, and attaching the kit component 512 to the inside of the return air trunk. Further, since the kit component 512 can be separated and collected also at the time of recycling and disassembly, recycle efficiency is improved.

(Use of the Peltier Element)

Furthermore, as mentioned above, in a case wherein it is impossible to provide the heat absorbing fin part 211 of the cooling plate 210 inside the storage compartment or the return air trunk, and to provide the heat dissipating fin part 212 of the cooling plate 210 inside the cooling air trunk, by providing a Peltier element (a plated semiconductor device using Peltier effect to transfer heat from one metal to the other metal by passing an electrical current through junctions between two types of metals, and a means to generate temperature difference between one side surface and the other side surface by occurrence of heat absorption on one side surface, and heat generation on the opposite side surface by passing a direct-current through itself), for example, in place of the heat conducting part 213 between the heat absorbing fin part 211 and the heat dissipating fin part 212, it is possible to make heat absorbed at the heat absorbing fin part 211, and heat dissipated at the heat dissipating fin part 212; therefore, it is applicable that both the heat absorbing fin part 211 and the heat dissipating fin part 212 are installed inside the storage compartment or inside the return air trunk, which makes the structure simple, and the installation and the maintenance, etc. easy. Further, since temperature difference between the heat absorbing fin part 211 and the heat dissipating fin part 212 can be controlled by magnitude of an electrical current, required dew condensation water can be set by a temperature, etc. inside the storage compartment, hence lack of dew condensation water can be prevented and the refrigerator 1 that can stably perform mist atomization can be obtained.

Since it is possible to have heat absorbed at the heat absorbing fin part 211, and heat dissipated at the heat dissipating fin part 212 as seen above, by providing a Peltier element (a plated semiconductor device using Peltier effect to transfer heat from one metal to the other metal by passing an electrical current through junctions between two types of metals, and a means to generate temperature difference between one side surface and the other side surface by occurrence of heat absorption on one side surface, and heat generation on the opposite side surface by passing a direct-current through itself), for example, in place of the heat conducting part 213 between the heat absorbing fin part 211 and the heat dissipating fin part 212, the electrostatic atomizing apparatus 200 can be also used in an air conditioner or a home electrical appliance, etc. wherein cool air at a low temperature, etc. cannot be used. In a case of the refrigerator 1, the electrostatic atomizing apparatus 200 can be installed in a section (the ceiling surface, the side wall surface, or the bottom surface, etc.) whose thickness of the heat insulation wall is desired to be as small as possible, wherein the cool air trunk is not provided so as to increase a volume inside a storage compartment of a storage compartment (for example, the refrigerating compartment 2), or a section wherein the cooling air trunk cannot be used, such as a partition wall or a shelf (for example, the partition wall between the refrigerating compartment 2 and the switching compartment 4, the partition wall between the refrigerating compartment 2 and the approximately closed containers 2X and 2Y, or the shelf, etc.), etc. that partitions between the storage compartments (between a storage compartment and a storage compartment). In this case, by installing the electrostatic atomizing apparatus 200 (the mist spraying apparatus) in the upper surface (the ceiling surface of the refrigerator 1) of the storage compartment provided at the uppermost part of the refrigerator 1, miniaturized nano-size mist can be efficiently sprayed all over the inside of the storage compartment. Further, a cool air trunk through which necessary low-temperature cool air flows, etc. is not included, and it is possible to commonalize the electrostatic atomizing apparatus 200 with an air conditioner or a home electrical appliance, etc., wherein cool air at a low temperature, etc. cannot be used, and to obtain the refrigerator 1, the air conditioner, or the home electrical appliance, which is low in cost and whereby bacterial eradication, deodorizing, and antifouling effects can be attained.

(Application to the Refrigerator Side Wall)

Figure 26:
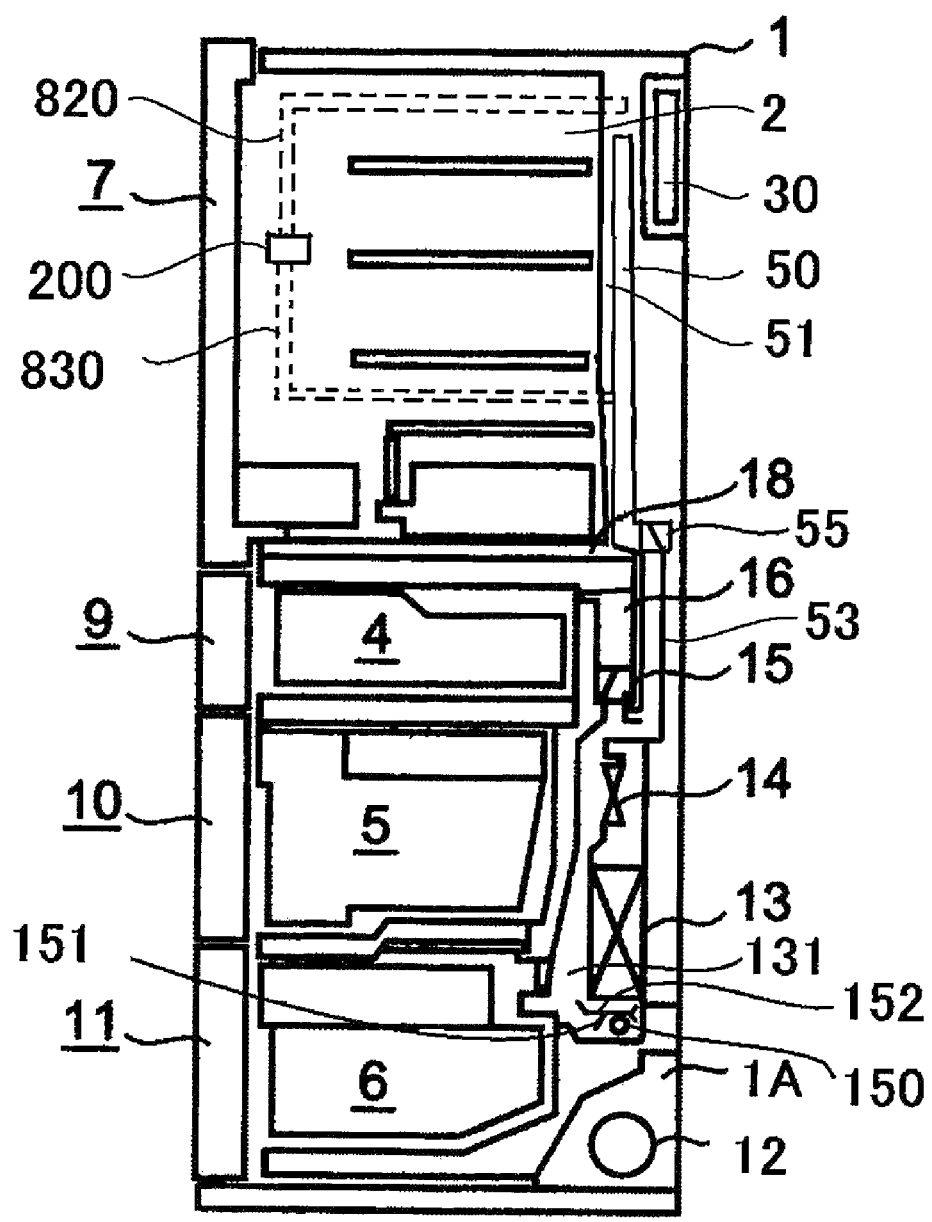
FIG. 26 is a side sectional view of the refrigerator 1 describing the embodiment of the present invention.
Figure 27:
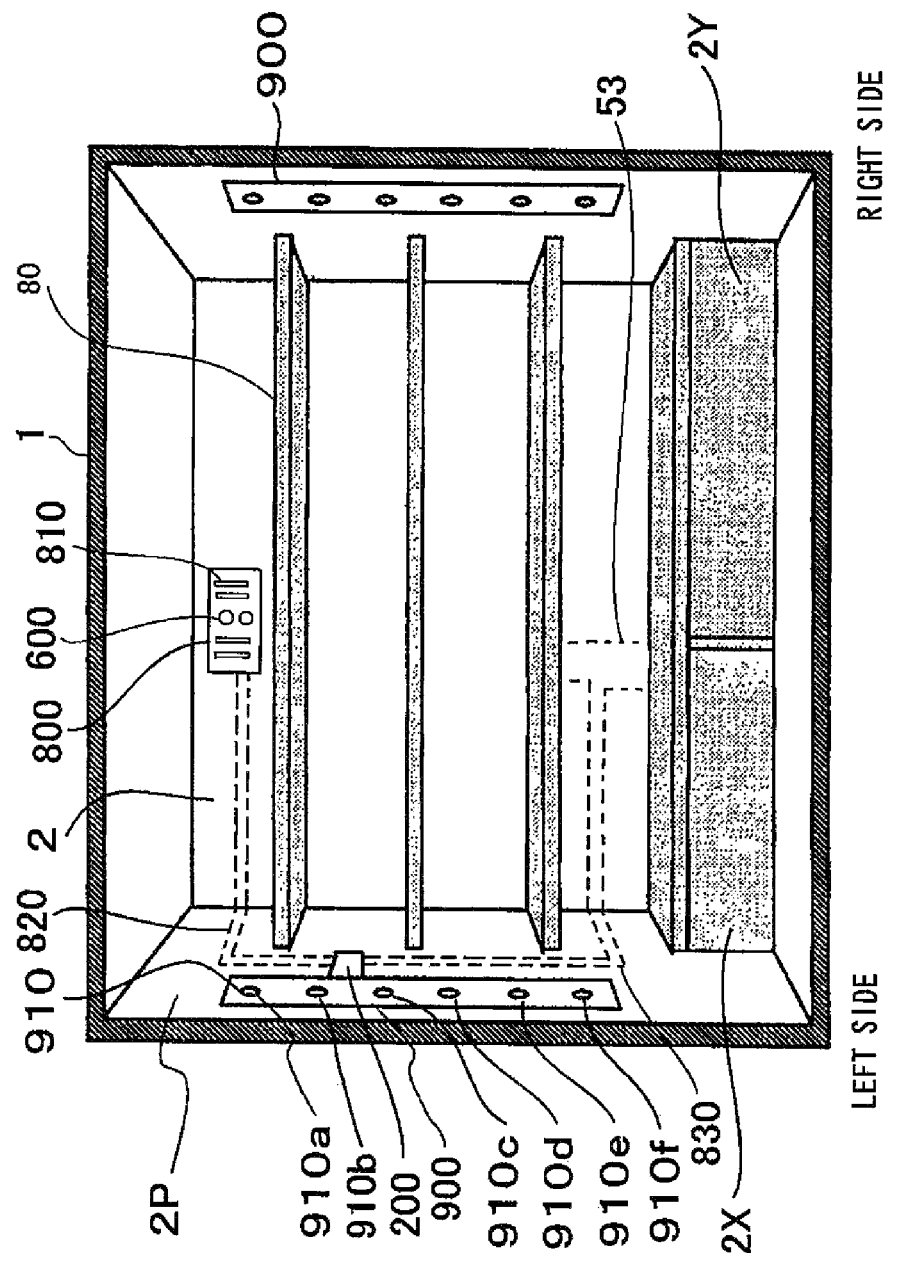
FIG. 27 is a front perspective view of the refrigerating compartment 2 of the refrigerator 1 describing the embodiment of the present invention.
Figure 28:
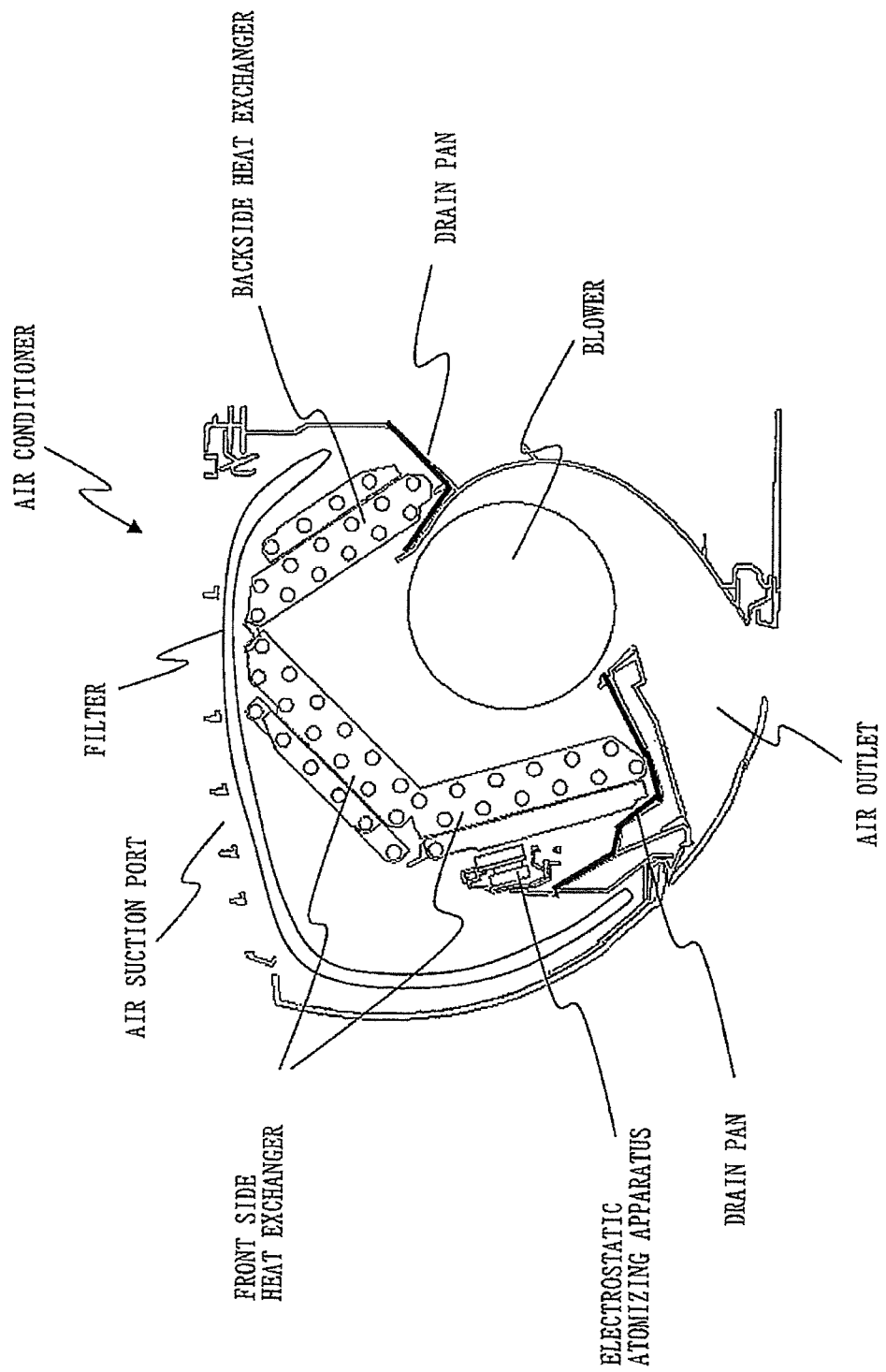
FIG. 28 is a view of an air conditioner including an atomizing apparatus placed downstream of a filter and above a drain pan.
Figure 29:
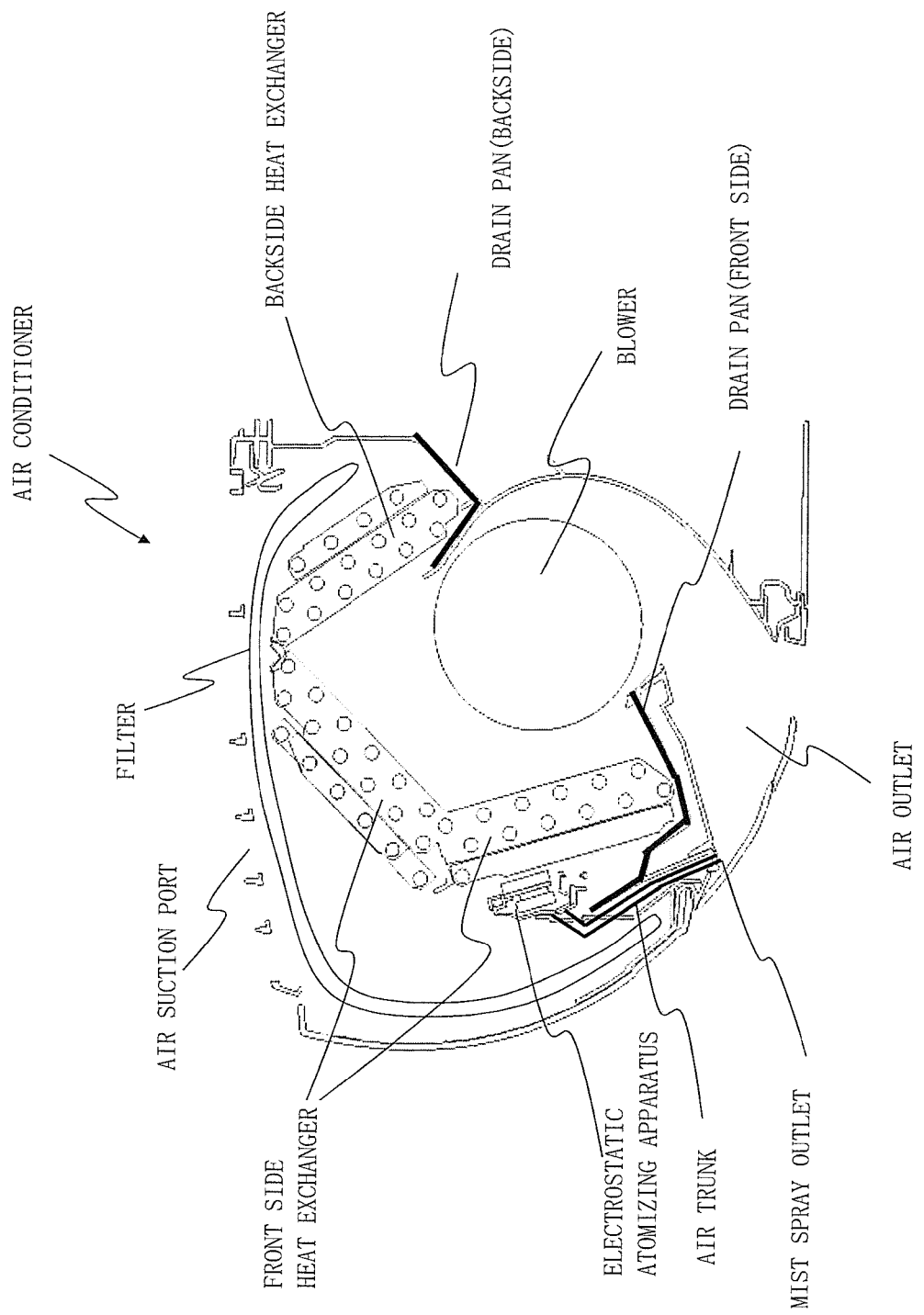
FIG. 29 is a view of an air conditioner wherein a mist spray outlet is provided in a place apart from the atomizing apparatus via an air trunk.

Next, it will be described one example in a case of applying the electrostatic atomizing apparatus 200 to a side wall of a storage compartment in the refrigerator 1. FIG. 26 is a side sectional view of the refrigerator 1 describing the first embodiment of the present invention, and FIG. 27 is a front perspective view of the refrigerating compartment 2 of the refrigerator 1 describing the first embodiment of the present invention. In the diagrams, the same signs are assigned to the similar parts as in FIG. 1 to FIG. 25, whereof the explanations are omitted.

In the diagrams, the electrostatic atomizing apparatus 200 installed in the inner side wall 2P of the refrigerator 1 is housed inside a recess portion formed in the inner side wall 2P. As shown in FIG. 6 through FIG. 11, the electrostatic atomizing apparatus 200 is made up of the electrode holding part 220, the discharge electrode 230 in a rectangular parallelepiped (prismatic columnar) shape or a columnar shape, and the counter electrode 240 including the opening part 241 in an approximately circular shape that is in an approximately similar shape as the cross-sectional shape (approximately circular shape) of the tip end of the protrusion part 231 of the discharge electrode 230, and further is an opening larger than a cross-section (approximately circular shape) of the protrusion part 231. Alternatively, as shown in FIG. 12 through FIG. 17, the electrostatic atomizing apparatus 200 is made up of the discharge electrode 230 including the main body part 232 in a prismatic columnar shape or a columnar shape elongated in the axial direction, and the protrusion part 231 in a pyramid shape or a conical shape that gets thinner toward the counter electrode 240 and that protrudes at the approximately right angle with respect to the axial direction from the main body part 232, the electrode holding part 220 that holds and houses the discharge electrode 230, the conducting member 280 for applying a voltage to the discharge electrode 230, the counter electrode 240 having the opening part 241 in an approximately quadrangle or an approximately circle shape, which is an opening larger than the cross-sectional shape (the approximately quadrangle or the approximately circle) of the tip end of the protrusion part 231 of the discharge electrode 230, and the fixing means 260 (the pressing means) whereby the discharge electrode 230 is held by and secured to the electrode holding part 220 via the conducting member 280.

Here, as a means to provide dew condensation water or supply water to the discharge electrode 230 or the electrode holding part 220, there are water supply means such as the cooling plate 210 that generates dew condensation water, or the water storage tank 270 that supplies supply water, etc., and the water supply means should preferably be installed directly above the discharge electrode 230, and the electrostatic atomizing apparatus 200 should preferably be attached to at least one of the inner side walls 2P, the fixing means 260 (the pressing means) and the electrode holding part 220 so that the dew condensation water that is generated on the cooling plate 210 or the water droplet 275 (the supply water) from the water storage tank 270, etc. drops over the main body part 232 of the discharge electrode 230, the slant part 264 of the fixing means 260 (the pressing means), or the electrode holding part 220 that are provided directly below. Further, in a case of using the water storage tank 270 in place of the cooling plate 210, since a user needs to feed water, it is applicable to install the electrostatic atomizing apparatus 200 in a detachable manner to the inner side wall 2P, the ceiling wall or the partition wall, in which case, the water storage tank 270 should preferably be installed in the fixing means 260 (the pressing means), or the electrode holding part 220 constituting the electrostatic atomizing apparatus 200 in a detachable manner, as shown in FIG. 17.

Cooling air blown from the cooler compartment 131 to the cooling air trunk 53 installed in the rear surface of the storage compartment passes through an electrostatic-atomizing-apparatus inlet cool air trunk 830 such as a duct, etc. whose circumference is surrounded, which is provided in the rear surface wall and the side wall heat insulation material, and which diverges laterally from the cooling air trunk 53 installed in the rear surface of the storage compartment, reaches the electrostatic atomizing apparatus 200 installed in the recess in the inner side wall 2P of the storage compartment, passes through an electrostatic-atomizing-apparatus outlet cool air trunk 820 such as a duct, etc. whose circumference is surrounded, and which is provided in the rear surface wall and the side wall heat insulation material in a state of including fine water droplets that are made into nano-size mist by the electrostatic atomizing apparatus 200, and reaches a mist spray compartment installed in an upper part of the rear surface wall of the storage compartment, for example. A mist spray cover 800 is provided in the mist spray compartment that is installed in a detachable manner, and the cool air including the fine water droplets that are made into nano-size mist by the electrostatic atomizing apparatus 200 is sprayed into the storage compartment from a mist spray outlet 810 formed in the mist spray cover 800.

As seen above, the electrostatic atomizing apparatus 200 including at least the discharge electrode 230 and the counter electrode 240 is allocated in the side wall (for example, in an approximate center position in height which is at a height position that is within reach of a user in the side wall of the refrigerating compartment 2) of the storage compartment, and the mist generated by the electrostatic atomizing apparatus 200 is delivered by cool air inside the electrostatic-atomizing-apparatus outlet cool air trunk 820 such as a cooling air duct whose circumference is surrounded, and is sprayed, to a different place (for example, the upper part of the rear surface wall of the refrigerating compartment 2, or the other second storage compartment (for example, the switching compartment 4 or the vegetable compartment 5) different from the storage compartment (for example, the refrigerating compartment 2) wherein the electrostatic atomizing apparatus 200 is installed, and the like) from a place (for example, the approximate center position in height which is at a height position that is within reach of a user in the side wall of the refrigerating compartment 2) where the electrostatic atomizing apparatus 200 is allocated; therefore, freedom of placement of the electrostatic atomizing apparatus 200 including at least the discharge electrode 230 and the counter electrode 240, and a mist spray unit (for example, the mist spray outlet 810 formed in the mist spray cover 800 provided in the mist spray compartment) for spraying mist that has been generated by the electrostatic atomizing apparatus 200 inside the storage compartment increases, and since mist atomization can be performed from a place where mist atomization is desired, degree of freedom of design increases. Further, since the electrostatic atomizing apparatus 200 including at least the discharge electrode 230 and the counter electrode 240, and the mist spray unit (for example, the mist spray outlet 810 formed in the mist spray cover 800 provided in the mist spray compartment) for spraying mist that has been generated by the electrostatic atomizing apparatus 200 into the storage compartment can be separated as different components, it is possible to make each component smaller and thinner, and to make the inner walls of the storage compartments in the refrigerator 1 thin, the inner volume of the storage compartments can be enlarged, and further, the refrigerator 1 whose cost is reduced can be obtained.

Here, since a user needs to remove the water storage tank 270 and adds water when the water storage tank 270 is installed, it is preferable that the placement of the electrostatic atomizing apparatus 200 is at a height position within reach of a user (without bending low, and is lower position than eye level in view of heights of Japanese women), and desirably at a height position from the waist to the shoulder position (height equal to or higher than approximately 80 cm, and equal to or lower than approximately 140 cm), and on the front side of the storage compartment. Further, the placement position of the mist spray outlet 810 should preferably be at an upper part in the storage compartment in the vertical direction so as to evenly spray from the upper part to the lower part inside the storage compartment by gravity, and in the width direction (the lateral direction), should preferably be at a position where mist can be evenly sprayed in the width direction (the lateral direction) as well inside the storage compartment in a state of being mixed in cool air, and in consideration of the position of a cool air outlet, the mist spray outlet 810 may be formed in one part or plural parts in an approximate center position in the width direction of the refrigerator 1, or may be formed in one part in an approximate end position or in two parts in the positions of the both ends, i.e., one part in each end position, or in plural parts in the width direction.

(Application to an Air Conditioner)

Now, it will be described a configuration in a case wherein the electrostatic atomizing apparatus 200 is mounted on an indoor unit of an air conditioner. Here, since the indoor unit of the air conditioner is the same as an indoor unit of a separate type air conditioner that is well known and common, the diagrammatic representation is omitted. The main body (casing) of the indoor unit includes inside itself a heat exchanger wherein a front side heat exchanger provided in a front side and a rear surface heat exchanger provided in an upper part or in a back side are arranged in an inverted V shape, an air suction inlet that is provided behind or above the front side heat exchanger of the heat exchanger, an air outlet that is provided in a lower part in the front surface of the indoor unit, a filter provided between the air suction inlet and the heat exchanger, a blower that is provided between the front side heat exchanger and the rear surface heat exchanger of the heat exchanger in the inverted V shape, to blow air that is heat exchanged via the filter and the heat exchanger after being taken in from the air suction inlet from the air outlet, and a drain pan that is provided in a lower part of at least one of the front side heat exchanger and the rear surface heat exchanger, wherein the electrostatic atomizing apparatus 200 is provided above the drain pan in downstream of the filter, thereby even when an electrical current is made not to be discharged between the lower end surface 211Y of the heat absorbing fin part 211 and the discharge electrode 230 when a voltage is applied to between the discharge electrode 230 and the counter electrode 240 by forming a notch or an opening in the electrode holding part 220 or the fixing means 260 of the electrostatic atomizing apparatus 200 so as not to accumulate dew condensation water or water dropping from the feed-water means (the heat absorbing fin part 211 or the water storage tank 270) in the discharge electrode 230, the electrode holding part 220 or the fixing means 260 in a state the discharge electrode 230 is held by the electrode holding part 220, water discharged from the notch or the opening in the electrode holding part 220 or the fixing means 260 is discharged to the drain pan; therefore, there is no need to provide a water receiving part additionally, the cost is reduced, the number of components can be reduced, and the assembly efficiency is improved.

Further, it is applicable to allocate the heat absorbing fin part 211, the discharge electrode 230, the counter electrode 240 and the electrode holding part 220 above the drain pan that receives drainage water near the outlet of the air conditioner, and to allocate the heat dissipating fin part 212 near the suction port. In this way, since the heat dissipating fin part 212, the discharge electrode 230 and the counter electrode 240, etc. are allocated near the outlet, a voltage is applied to the discharge electrode 230 and the counter electrode 240 and mist is generated, and the generated mist is blown into a room together with cool air that has been blown from the outlet and has been cooled, thereby bacterial eradication and humidification inside the room can be performed. Further, even when water accumulated in the discharge electrode 230 spills from the electrode holding part 220, the water can be received by the drain pan, and can be discharged outside the room without providing any components such as a water receiving part, etc., and it is possible to obtain an air conditioner of low in cost.

Furthermore, it is also applicable to place the electrostatic atomizing apparatus 200 near the air suction port downstream the air suction port in the indoor unit of the air conditioner, and to provide the mist spray outlet on the upstream side of the air outlet in the indoor unit of the air conditioner via an air conveying path, such as a duct, a hose, etc. Here, the mist spray outlet may double as the air outlet, or the mist spray outlet may be placed so as to open in the air conveying path or the air outlet, so that mist is sprayed from the air outlet inside the room into which the air outlet opens. As shown, the electrostatic atomizing apparatus 200 including at least the discharge electrode 230 and the counter electrode 240 is allocated downstream the air suction port of the indoor unit of the air conditioner or near the air suction port, and the mist generated by the electrostatic atomizing apparatus 200 is sprayed to a place (for example, the inside of the room into which the air outlet of the indoor unit of the air conditioner opens, or the inside of the air conveying path on the upstream side of the air outlet, etc.) different from a section where the electrostatic atomizing apparatus 200 is allocated, via an inside of an air trunk such as a duct whose circumference is surrounded; therefore, freedom of placement of the electrostatic atomizing apparatus 200 including at least the discharge electrode 230 and the counter electrode 240, and the mist spray unit (the mist spray outlet) for spraying the mist generated by the electrostatic atomizing apparatus 200 inside the room increases, and since mist atomization can be performed from a place where mist atomization is desired, degree of freedom of design increases.

Further, since temperature difference between the heat absorbing fin part 211 and the heat dissipating fin part 212 can be controlled by a magnitude of an electrical current, required dew condensation water can be set by a temperature inside the room, etc., lack of dew condensation water can be prevented, and miniaturized nano-size mist can be evenly and stably sprayed. Additionally, since the heat dissipating fin part 212 is allocated near the suction port, even when the heat dissipating fin part 212 produces heat and the temperature rises slightly, the heat is taken in by the suction port, by which a temperature of cool air blown into the room is not influenced; therefore, an air conditioner or a home electrical appliance, etc., temperature control over which is easy without influence on temperature control over an inside of a room can be obtained.

(Display)

Here, displaying of an operation status of the electrostatic atomizing apparatus 200 (the mist spraying apparatus), displaying of an amount of sprayed mist or a degree of bacterial eradication (strength of bacterial eradication) inside a storage compartment by a strength (for example, a magnitude of an applied voltage or a spray amount of sprayed mist) of the operation of the electrostatic atomizing apparatus 200, and in a case of displaying an amount of used electricity, electricity expense, and an amount of carbon dioxide emission, etc. as a figure such as a bar graph, a leaf mark, etc. by the LEDs 910 in the lighting device 900 inside the refrigerator, by dividing the figure into multiple parts and changing the colors in accordance with the number of division, and so on, displaying the amount of sprayed mist or the degree of bacterial eradication, etc. by the number of the divided parts whose colors are changed can be applied not only to the refrigerator 1, but also to an air conditioner or a home electrical appliance, and a similar display can be performed; in a case of the air conditioner, it is applicable to display on a design surface (for example, a front surface cover, etc.) of a front surface of an indoor unit, or a display unit of a remote controller whereby operation, stop, and temperature setting, etc. of the air conditioner are performed, etc., in which case, it is possible to obtain effects that a user can visually determine at once the amount of sprayed mist or the degree of bacterial eradication (strength of bacterial eradication) inside the storage compartment by the operation status of the electrostatic atomizing apparatus (the mist spraying apparatus) 200, and the strength (for example, the magnitude of the applied voltage or the spray amount of the sprayed mist, etc.) of the operation of the electrostatic atomizing apparatus 200 (the mist spraying apparatus), as in the case of the refrigerator.

As for a home electrical appliance such as the refrigerator 1, the air conditioner, etc. according to the present embodiment, it is applicable to display an installation position of the mist spraying apparatus (the electrostatic atomizing apparatus 200) in a figure, etc. in an overall view, etc. so as to be visually confirmed, so that a storage compartment and a section whereto the electrostatic atomizing apparatus 200 or each component (for example, the cooling plate 210, the discharge electrode 230, or the high-voltage power supply part 250, etc.) constituting the electrostatic atomizing apparatus 200 is installed, and material names, etc. of the electrostatic atomizing apparatus 200 or each component of the electrostatic atomizing apparatus 200 can be visually recognized with ease at the time of recycling, and so on.

Here, in the case of the refrigerator 1, an indicator chart such as an overall view, a schematic layout of the storage compartments, a perspective view, a cubic diagram, a partial indicator chart, a developed figure, etc. of the refrigerator 1 in the case of the refrigerator 1 is displayed on the reverse face or the side surfaces of the main body of the refrigerator, on the inside refrigerator side of the opening and closing door, or the control device, etc. Further, in the case of the air conditioner, an indicator chart, such as an overall view, a schematic layout of the components, a perspective view, a cubic diagram, a partial indicator chart, a developed figure, etc. of the indoor unit or the outdoor unit is displayed on a reverse face, side surfaces, an inner side of a design cover (the front cover, etc.), or a control device, etc. Furthermore, the placement position of the electrostatic atomizing apparatus 200 (the mist spraying apparatus) is indicated in these indicator charts such as the overall view, etc. in a figure and so on so as to be visually confirmed at once. In addition, it is applicable to include the installation position of the high-voltage power supply part 250 when the high-voltage power supply part 250 is allocated in a different section, and to include installment positions, etc. of the other components usable in recycling additionally in the display.

In this case, information useful at the time of recycling and disassembly is displayed to be visually recognized at once, by displaying in a sign such as a black circle (●), or in a graphic in an approximately similar shape as the shape of the electrostatic atomizing apparatus 200, etc., and further, by displaying names of materials and used weights used for the electrostatic atomizing apparatus 200, whether the materials are recyclable, a recycle method, precautions at the time of recycling and disassembly, etc. in a reference chart, and the like. Thus, since it is possible to recognize whether a material, etc. that affects the human body at the time of recycling is not used, and a reusable component at the time of recycling and the weight, etc., disassembly can be performed without confusion at the time of disassembly, hence a home electrical appliance such as the refrigerator 1, the air conditioner, etc. which can be recycled, whose disassembly efficiency is favorable, and whose recycle efficiency is improved, can be obtained.

Here, in the case the home electrical appliance is the refrigerator 1, standard use periods are set for the main body of the refrigerator, and each functional component (for example, the electrostatic atomizing apparatus 200, the compressor 12, the defrosting heater 150, and the cool air circulation fan 14, etc.), which are displayed on the control panel 60 of the main body of the refrigerator, etc.

When the home electrical appliance is an appliance such as an air conditioner, an air purifier, etc., it is applicable that standard use periods are set for an indoor unit, an outdoor unit, a main body of the appliance, and functional components (for example, the electrostatic atomizing apparatus 200, a compressor, and a blower, etc.), and are displayed on a design panel of a front face of a main body of an indoor unit, or a remote controller, etc. Further, it is also applicable that, for example, standard use periods are set for the main body of the indoor unit or the main body of the outdoor unit including the functional components, or standard use periods are set for the functional components separately from the main body of the indoor unit or the main body of the outdoor unit, and the standard use periods (standard use times) are displayed on the design panel on the front face of the main body of the indoor unit, or the remote controller that directs operation and stop, etc. of the appliance, etc. as a size, a length, or the number of figures such as a bar graph, a leaf, etc., and a current use period is also displayed alongside by changing colors or patterns, or the like, which can be visually confirmed by a user so as to encourage replacement for the user.

Here, it is also applicable, for example, to set the standard use period for the appliance including the functional component, or to set the standard use periods for the main body of the appliance such as the refrigerator 1, etc., and the functional component (the electrostatic atomizing apparatus 200, or the compressor 12, etc.) separately, display the standard use periods (the standard use times) graphically in a bar graph or the like on the display part of the control panel 60, the front panel, or the remote controller, etc., and to graphically display the current use period (time) alongside by changing colors or patterns, etc., so as to be displayed visually for a user. Further, it is also applicable to store standard performance data (data, etc. of chronological change of ability and input power, etc. concerning performance, such as input power to a compressor, input power to a fan, an used amount of electricity and capability of the whole appliance, etc.) that varies with the number of years in use that is obtained by an experiment or a calculation, etc. in a microcomputer 31 beforehand as a table in addition to display of the actual use period of the appliance, and display a degree of degradation of the performance (the capability or the input power, etc.) as a length of a bar graph or the number of figures. That is, it is also applicable to visually encourage replacement for the user by a display (for example, display as a length of a bar graph, or the number of figures, etc.) whereby an estimated performance at the present time is displayed by a declined rate of performance with respect to an initial performance, while regarding a performance at an initial period of purchase as 100 percent.

That is, since a storing means (the microcomputer 31) that stores a standard use period set beforehand of the appliance such as the electrostatic atomizing apparatus 200, the refrigerator 1, the air conditioner, the air purifier, etc. is included, and the current use period measured by a timer, etc. with respect to the standard use period stored in the storing means (the microcomputer 31) is displayed on a display part (the control panel 60 of the refrigerator, or the display part in the front cover of the indoor unit, etc.) of the main body of the appliance, or the display part of the remote controller that directs operation and stop, etc. of the appliance, as a size, a length, or the number of figures, etc. of a bar graph or a leaf, etc., a user can visually recognize the use period of the appliance by visual confirmation, and it is possible to encourage a service such as replacement of the appliance or a component, or exchange of a component, etc. for the user.

Further, a remaining usable period with respect to the standard use period of the appliance may be displayed as a figure such as a bar graph, a leaf mark, etc. In this case, since the size and the number of the figures such as the bar graph, etc. indicating the usable period decrease as the use period increases, it is possible to let a user have risk awareness, and be conscious about replacement before a breakdown. Additionally, by making a message that encourages replacement or a service displayed when the remaining period becomes smaller than a predetermined period, it is possible to further make the user be conscious about replacement before the breakdown.

Furthermore, it is possible to make the user be aware of improvement of energy-saving consciousness by displaying a magnitude of an applied voltage, an amount of used electricity, electricity expense, and an amount of carbon dioxide emission, etc. in the appliance during operation of the electrostatic atomizing apparatus 200 as a size, a length or the number of figures, such as a bar graph, a leaf, etc. on the main body or the remote controller, etc. that directs operation and stop, etc. of the appliance. Additionally, relation of the amount of used electricity or the amount of carbon dioxide emission, etc. of the appliance due to the magnitude of the applied voltage during operation of the electrostatic atomizing apparatus 200 can be recognized, and energy-saving consciousness is enhanced in the user. Here, by making the user capable of setting the magnitude of the applied voltage to the electrostatic atomizing apparatus 200 (it is applicable that the magnitude of the applied voltage can be changed by a multiple-graded setting such as strong, intermediate and weak, or a non-graded setting) by control buttons, the remote controller or the like, it is possible to select a weak mode and the like when energy saving is desired, and to conserve energy.

Further, it may be applicable to measure an instant amount of used electricity or an accumulated (for example, in every one day, or in every one month, etc.) amount of used electricity by including a means that measures an amount of used electricity of the main body of the appliance or the functional components (for example, the electrostatic atomizing apparatus 200 or the compressor 12, etc.), and to graphically display the instant amount of used electricity or the accumulated (for example, in every one day, or in every one month, etc.) amount of used electricity as a bar graph, or the number of leaf marks, etc. on the control panel 60 on the front face of the refrigerator 1, the display part in a panel on the front face or the top face of the air conditioner or the air purifier, or the display part of the remote controller, and the like, thereby a user using the home electrical appliance is made to be aware of energy saving through sight.

In addition, it is also applicable to start presenting such a graphical display on the main body or the remote controller, etc. in addition to a message that encourages checkup or replacement of the main body or the functional component, and the like, for a user when the actual time of use surpasses a predetermined rate (for example, 90% or 95%, etc. of the standard use time) of the standard use time, thereby a user is encouraged to check, exchange, or replace the main body or the functional component, etc. Furthermore, it is also applicable to encourage checkup, exchange or replacement of the main body or the functional component, etc. for the user through sight by starting display in the above-mentioned figure, etc. on the main body or the remote controller, etc. when the actual use time surpasses the first predetermined rate (for example, 90% of the standard use time, etc.) of the standard use time, and by displaying a message and so on that encourages checkup or exchange of the main body or the functional component, etc. for the user when the actual use time surpasses the second predetermined rate (for example, 95% of the standard use time, etc.) that is greater than the first predetermined rate of the standard use time, so as to indicate display in multiple stages (for example, two stages) as the time passes. In this way, by displaying a figure or a text such as a message that encourages checkup, exchange or replacement for the user on the main body or the remote controller, etc. when the standard use period has passed, it is possible to prevent performance decrease due to aging degradation, or a breakdown or ignition, etc. due to clogging with dust, etc., and to obtain the refrigerator 1, the air conditioner, or a home electrical appliance that is highly reliable. Especially for the electrostatic atomizing apparatus 200 whereto a high voltage is applied, it is effective for preventing lack of water supply to the electrostatic atomizing apparatus 200 due to clogging in the electrode holding part 220 with foreign particles, or clogging between the fin plates with foreign particles, etc., and for preventing a breakdown of the electrostatic atomizing apparatus 200 due to attachment of dust or foreign particles, etc. to the electrodes, ignition by degradation of the electrodes, etc., and the like.

As shown above, in the present embodiment, the discharge electrode 230 that is made up of the main body part 232 formed of foam metal which is a metallic porous body having a three-dimensional net structure, such as titanium material, etc., and of the protrusion part 231 that is integrally formed with the main body part 232 in a manner to protrude from the main body part 232, whereto water which attaches to the surface of the main body part 232 is supplied by capillary action, the electrode holding part 220 that holds the discharge electrode 230, the counter electrode 240 that is provided in the electrode holding part 220, and is provided so as to be opposed to the protrusion part 231, the water supply means (the cooling plate 210 or the water storage tank 270) which is provided directly above the main body part 232 via the predetermined clearance Z and which supplies water to the discharge electrode 230 or the electrode holding part 220, and the fixing means 260 that secures the discharge electrode 230 that is housed in and held by the electrode holding part 220 or the counter electrode 240 to the electrode holding part 220 are included, wherein the electrode holding part 220, the discharge electrode 230, the counter electrode 240 and the fixing means 260 are integrally formed, and mist is generated by applying a voltage to between the discharge electrode 230 and the counter electrode 240; therefore, an amount of water supply and capillary force are larger, and clogging resistance against a foreign matter is much higher since pore diameters are large compared to a case wherein a ceramic material is used for the discharge electrode 230.

Further, it is also applicable to place the electrostatic atomizing apparatus 200 downstream the air suction port in the indoor unit of the air conditioner and near the air suction port, and to provide the mist spray outlet on the upstream side of the air outlet in the indoor unit of the air conditioner via the air conveying path, such as the duct, the hose, etc. Here, the mist spray outlet may double as the air outlet, and mist may be sprayed from the air outlet inside the room into which the air outlet opens by placing the mist spray outlet in a manner to open into the air conveying path or the air outlet. As shown, the electrostatic atomizing apparatus 200 including at least the discharge electrode 230 and the counter electrode 240 is allocated downstream the air suction port in the indoor unit of the air conditioner or near the air suction port, and the mist generated by the electrostatic atomizing apparatus 200 is sprayed to the place (for example, the inside of the room into which the air outlet in the indoor unit of the air conditioner opens, or the inside of the air conveying path on the upstream side of the air outlet, etc.) different from the section where the electrostatic atomizing apparatus 200 is allocated, via the inside of the air trunk such as the duct, etc. whose circumference is surrounded; therefore, freedom of placement of the electrostatic atomizing apparatus 200 including at least the discharge electrode 230 and the counter electrode 240, and the mist spray unit (the mist spray outlet) for spraying mist generated by the electrostatic atomizing apparatus 200 into the room increases, and since mist atomization can be performed from the place where mist atomization is desired, degree of freedom of design increases.

Furthermore, it is possible to increase degree of freedom of a set range of the predetermined clearance F and a set range of an applied voltage, and to easily perform generation of nano-size mist reliably. Further, since the water supply means is provided directly above the main body part 232, in comparison with a case wherein the water supply means is provided in a lower part of the discharge electrode 230 or in a separate place apart from the discharge electrode 230, water supplied from the water supply means directly drops over the discharge electrode 230 (or the electrode holding part 220 or the fixing means 260) provided immediately below, and a conveying part for conveying dew condensation water generated on the heat dissipating fin part 211 in the cooling plate 210, which is the water supply means, or water supplied from the water storage tank 270 to the electrode holding part 220 (or the discharge electrode 230 or the fixing means 260) is unnecessary; therefore, the refrigerator 1 simple in structure, compact in size, and low in cost can be obtained. That is, since the conveying part that conveys water is unnecessary, and there is no possibility that the conveying part is clogged with foreign particles, etc., and the dew condensation water is not supplied to the discharge electrode 230, the electrostatic atomizing apparatus 200 and the refrigerator 1 simple in structure, low in cost, and highly reliable can be obtained. Furthermore, degree of freedom of the shapes and the placement of the feed-water means (for example, the cooling plate 210, the water storage tank 270, or the like), the electrode holding part and the discharge electrode increase, the shapes and the placement of the discharge electrode 230, the counter electrode 240 and the feed-water means (for example, the cooling plate 210, the water storage tank 270, or the like) can be freely set in accordance with the structure of each home electrical appliance, such as the refrigerator 1, the air conditioner, the air purifier, and the like, and the electrostatic atomizing apparatus 200 that is compact in size and efficient can be obtained in accordance with the home electrical appliance.

Further, in a case wherein the sizes (the widths, the thicknesses, etc.) of the external shapes or the cross-sectional areas of the main body part 232 and the protrusion part 231 are approximately the same, when the length in the axial direction of the main body part 232 is within a range of equal to or larger than 4 times but equal to or smaller than 20 times the length of the protrusion part 231, there are effects that the processability is better, the amount of water supply from the main body part 232 to the protrusion part 231 is increased, and the time for water supply can be shortened.

Furthermore, since foam metal such as titanium, etc. is used, which is a metallic porous body having a three-dimensional net structure like a sponge, the amount of water absorption inside the metal is approximately 2 to 5 times larger than that of what is not foam metal, capillary force is larger than that in sintered metal, electrical resistance is approximately $(0.4 \text{ to } 2) \times 10^{-7}$ $\Omega \cdot m$ and small, hence electricity can be efficiently applied to water as conductive material; therefore, the foam metal can conduct electricity far more readily than a ceramic with large electrical resistance (the electrical resistance is approximately $10^{12}$ $\Omega \cdot m$ and large), can increase an amount of generated mist, and setting, etc. of an applied voltage is easy, and further, the applied voltage can be made small, and it is possible to generate nano-size mist readily and easily. In the present embodiment, the discharge electrode made up of the main body part 232 formed of foam metal and the protrusion part 231 whereto water that is attached to the surface of the main body part 232 is supplied by capillary action, the electrode holding part 220 that holds the discharge electrode 230, the counter electrode 240 provided in the electrode holding part 220 and provided so as to be opposed to the protrusion part 231, the water supply means (for example, the cooling plate 210, or the water storage tank 270, etc.) that supplies water to the discharge electrode 230, and the high-voltage power supply part 250 that generates mist from the protrusion part 231 by applying a voltage to between the discharge electrode 230 and the counter electrode 240 are included, wherein foam metal having a three-dimensional net structure with pore diameters of 10 to 800 μm (preferably with pore diameters of 50 to 300 μm, and further preferably with pore diameters of 50 to 150 μm), and a voidage of 60 to 90% (preferably 70 to 80%) is used for the discharge electrode 230, and by setting the pore diameters of the discharge electrode 230 to be between 10 and 800 μm, clogging resistance against foreign matter dramatically increases, and it is possible to supply water from the main body part 232 to the protrusion part 231 stably for a long period. Further, since the foam metal having the three-dimensional net structure, such as titanium, etc. with a high voidage of not less than 60 and not more than 90% is used, a larger amount of water can be retained inside the foam metal compared to a conventional ceramic or sintered metal, etc. Thus, a large amount of nano-size mist can be generated efficiently.

Further, the discharge electrode 230 is formed of foam metal having a three-dimensional net structure, and is made up of the main body part 232 in an approximately rectangular parallelepiped or an approximately columnar shape elongated in the axial direction, and the protrusion part 231 in an approximately rectangular parallelepiped shape, an approximately columnar shape, an approximately pyramid shape, or an approximately conical shape, which protrudes at the approximately right angle with respect to the axial direction of the main body part 232 from the middle in the axial direction of the main body part 232, and which is shorter than the length in the axial direction of the main body part 232, and is integrally formed with the main body part 232, whereto water that attaches to the surface of the main body part 232 is supplied by capillary action, wherein the length in the axial direction of the main body part 232 is within the range of equal to or larger than 4 times but equal to or smaller than 20 times the length of the protrusion part 231, hence the main body part is divided into two parts (for example, the first main body part 237 and the second main body part 238) at a protruding position of the protrusion part 231 against the axial direction of the main body part 232, and water can be supplied by capillary action from two parts (the both ends of the protrusion part 231) of the first main body part 237 and the second main body part 238 to the protrusion part 231; therefore, a large amount of water can be supplied to the protrusion part 231, the amount of sprayed mist can be increased, and mist atomization can be performed stably. Further, even when either (for example, the first main body part) of the first main body part 237 or the second main body part 238 becomes unable to function due to clogging, etc., water can be supplied to the protrusion part 231 by the other part (the other one) (for example, the second main body part 238), hence water can be stably supplied to the protrusion part 231 for a long period, and the electrostatic atomizing apparatus 200 (the mist spraying apparatus) which can stably spray mist for a long period, and is highly reliable can be obtained.

Since a cover part (the feed-water means cover part 220X or 269) that covers at least one of the feed-water means (the heat absorbing fin part 211 of the cooling plate 210 or the water storage tank 270), the electrode holding part 220, and the fixing means 260 is provided in the electrode holding part 220 or the fixing means 260 so that water supplied to the discharge electrode 230, the electrode holding part 220 or the fixing means 260 by dropping from the feed-water means (for example, the heat absorbing fin part 211 of the cooling plate 210 or the water storage tank 270, etc.) provided directly above the discharge electrode 230 or the electrode holding part 220 is not directly subject to an air flow in a fall path of water from the feed-water means until the water drops over the discharge electrode 230, the dropping water droplet 275 or dew condensation water is less likely to be subject to foreign materials such as dust, mold, foreign particles, etc. in air surrounding the place where the feed-water means, the electrode holding part 220 or the fixing means 260 (the pressing means) is provided, a water droplet that attaches to the discharge electrode 230 or a water droplet inside the electrode holding part 220 is less likely to foul, clogging in the discharge electrode 230 can be prevented, and the electrostatic atomizing apparatus 200 that is highly reliable, clean and hygienic can be obtained.

Furthermore, since the notch or the opening is formed in the electrode holding part 220 or the fixing means 260, and dew condensation water dropping from the feed-water means (the heat absorbing fin part 211 or the water storage tank 270) or water does not accumulate in the discharge electrode 230, the electrode holding part 220 or the fixing means 260 in a state wherein the discharge electrode 230 is held in the electrode holding part 220, there is no possibility that a water droplet is in a state of attaching to the surface of the main body part 232 of the discharge electrode 230, or water is in a state of being accumulated in the electrode holding part 220, and that an electrical current is discharge d between the lower end surface 211Y of the heat absorbing fin part 211 and the discharge electrode 230, even when a voltage is applied to between the discharge electrode 230 and the counter electrode 240, hence the electrostatic atomizing apparatus 200 or an appliance that is safety can be obtained. Here, the holding part of the discharge electrode 230 in the electrode holding part 220 should preferably be configured (or, should be configured to be able to eject water from the holding part of the discharge electrode 230 so as to configure the discharge electrode 230 not to accumulate water in the surface thereof, wherein it is configured that a water reservoir part that accumulates the ejected water is separately provided in a position apart from the discharge electrode 230, such as on the lower side, and the water accumulating in the water reservoir part does not contact with the discharge electrode 230) not to accumulate water therein. Further, by setting the predetermined clearance Z between the lower end surface 211Y of the heat absorbing fin part 211 and the discharge electrode 230 equal to or larger than 4 mm (preferably equal to or larger than 6 mm) so as to secure a distance where discharge does not take place between the heat absorbing fin part 211 and the discharge electrode 230 even when a water droplet is attached to the upper surface of the main body part 232 of the discharge electrode 230, and it is possible to improve safety further.

In addition, the discharge electrode 230 that is made up of the main body part 232 formed of foam metal, and of the protrusion part 231 that is integrally formed with the main body part 232, and is formed so as to protrude from the main body part 232, whereto water which attaches to the surface of the main body part 232 is supplied by capillary action, the electrode holding part 220 that houses the discharge electrode 230, the counter electrode 240 that is provided in the electrode holding part 220, and is provided so as to be opposed to the protrusion part 231, the water supply means (the heat absorbing fin part 211 of the cooling plate 210, or the water storage tank 270), which is provided directly above the main body part 232 via the predetermined clearance Z and which supplies water to the discharge electrode 230 or the electrode holding part 220, the electrostatic atomizing apparatus 200 which is made up of at least the discharge electrode 230, the counter electrode 240 and the electrode holding part 220, and which generates mist by applying a voltage between the discharge electrode 230 and the counter electrode 240, and a spray outlet that is provided in a place apart from the electrostatic atomizing apparatus 200, and that is connected to the electrostatic atomizing apparatus 200 via the air conveying path are included, wherein nano-size mist generated by the electrostatic atomizing apparatus 200 is sprayed to inside of a storage compartment, a room, etc., into which the spray outlet opens, from the spray outlet provided in the place apart from the electrostatic atomizing apparatus 200; therefore, freedom of placement of the electrostatic atomizing apparatus 200 including at least the discharge electrode 230 and the counter electrode 240, and the mist spray unit (the mist spray outlet) for spraying mist generated by the electrostatic atomizing apparatus 200 into the room increases, and since mist atomization can be performed from the place where mist atomization is desired, hence it is possible to perform design in accordance with a structure of each home electrical appliance, such as the refrigerator 1, an air conditioner, an air purifier, etc., and degree of freedom of design increases. Furthermore, since the water supply means is provided directly above the main body part 232 via the predetermined clearance Z, degree of freedom of the shape and the placement of the feed-water means (the cooling plate 210 or the water storage tank 270), which is the water supply means, or the discharge electrode 230 increases, and it is possible to freely set the shapes and the placement of the discharge electrode 230, the counter electrode 240, the cooling plate 210 and the water storage tank 270 in accordance with the structure of each home electrical appliance, such as the refrigerator 1, the air conditioner, the air purifier, etc., and to obtain the electrostatic atomizing apparatus that is compact in size and of great efficiency can be obtained in accordance with home electrical appliance.

REFERENCE SIGNS LIST

1: Refrigerator, 1A: Machine compartment, 2: Refrigerating compartment, 2A: Chilled compartment, 2P: Inner side wall, 2X: Approximately closed container, 2Y: Approximately closed container, 3: Ice making compartment, 4: Switching compartment, 5: Vegetable compartment, 6: Freezing compartment, 7: Refrigerating compartment door, 7A: Left refrigerating compartment door, 7B: Right refrigerating compartment door, 8: Ice making compartment door, 9: Switching compartment door, 10: Vegetable compartment door, 11: Freezing compartment door, 12: Compressor, 13: Cooler, 14: Cool air circulation fan, 19: Switching compartment thermistor, 22: Thermopile, 15: Switching compartment damper, 16: Switching compartment cooling air trunk, 30: Control device, 50: Cooling air trunk, 51: Partition wall, 53: Cooling air trunk, 55: Refrigerating compartment damper, 60: Control panel, 60a: Compartment selection switch, 60b: Temperature zone transfer switch, 60c: Instant freezing switch, 60d: Ice making transfer switch, 60e: Mist spray switch, 72: Door pocket, 80: Inside refrigerator shelf, 131: Cooler compartment, 150: Defrosting heater, 151: Heater roof, 152: Defrosting electrode holding part, 200: Electrostatic atomizing apparatus, 210: Cooling plate, 211: Heat absorbing fin part, 211a: Heat absorbing fin plate, 211b: Heat absorbing fin plate, 211c: Heat absorbing fin plate, 211d: Heat absorbing fin plate, 211e: Heat absorbing fin plate, 211T: Protrusion part, 211W: Slant part, 211X: Outer side surface, 211Y: Lower end surface, 212: Heat dissipating fin part, 212a: Heat dissipating fin plate, 212b: Heat dissipating fin plate, 212c: Heat dissipating fin plate, 212d: Heat dissipating fin plate, 212e: Heat dissipating fin plate, 213: Heat conducting part, 214: Void part, 220: Electrode holding part, 220G: Water concentration part, 220K: Width direction size, 220L: Length direction size, 220W: Slant part, 220X:

Feed-water means cover part, 222: Notch part, 223: Counter electrode housing part, 230: Discharge electrode, 231: Protrusion part, 232: Main body part, 237: The first main body part, 238: The second main body part, 240: Counter electrode, 241: Opening part, 250: High-voltage power supply part, 251: Power supply, 260: Fixing means, 261: Counter electrode cover part, 262: Conducting member pressing part, 263: Step part, 268: Fixing nail part, 269: Feed-water means cover part, 270: Water storage tank, 271: Graduation mark, 275: Water droplet, 277: Water discharge spout, 280: Conducting member, 286: Electrode conducting means conducting part, 300: Cover, 511: Cooling plate heat-insulating material, 512: Kit component, 515: Front surface opening part, 531: Side cool air outlet, 532: Side cool air outlet, 533: Upper cool air outlet, 534: Lower cool air outlet, 600: Electrostatic-atomizing-apparatus light, 800: Mist spray cover, 810: Mist spray outlet, 820: Electrostatic-atomizing-apparatus outlet cool air trunk, 830: Electrostatic-atomizing-apparatus inlet cool air trunk, 900: Lighting device, 910: LED, 910a: LED, 910b: LED, 910c: LED, 910d: LED, 910e: LED, 910f: LED, 915: Optical axis.

The invention claimed is:

1. An atomizing apparatus that generates mist by being applied a voltage, the atomizing apparatus comprising:
   a discharge electrode composed of a main body part, and a protrusion part whereto water that attaches to a surface of the main body is supplied;
   an electrode holding part that houses the discharge electrode;
   a water storage tank that is provided apart from the discharge electrode or the electrode holding part via a space, and that supplies water to the discharge electrode or the electrode holding part,
   wherein the water storage tank, the electrode holding part and the discharge electrode are integral; and
   a pressing member that prevents the discharge electrode housed in the electrode holding part from moving, the pressing member being integral with the water storage tank, the electrode holding part and the discharge electrode; and
   wherein the pressing member includes an opening portion for allowing water supplied by the water storage tank to pass through and contact the discharge electrode and one of a conducting member pressing part and an electrode pressing portion for pressing the discharge electrode against the electrode holding part.

2. The atomizing apparatus according to claim 1, further comprising a feed-water means cover part that covers at least a part of a water supply path between the water supply means and the electrode holding part.

3. The atomizing apparatus according to claim 1, further comprising a predetermined clearance between the water storage tank and the discharge electrode.

4. The atomizing apparatus according to claim 1, wherein the electrode holding part receives the water dropping from the water storage tank via the space, and further includes a water discharge spout to discharge water that is supplied by the water storage tank in a state where the discharge electrode is held by the electrode holding part.

5. The atomizing apparatus according to claim 1, wherein the main body part has a rectangular parallelepiped shape or a columnar shape, the protrusion part has a rectangular parallelepiped shape, a columnar shape, pyramid shape, or a conical shape, and a length of the main body part from an end to another opposite end is between 4 and 20 times longer than the protrusion part from a base attached to the main body to the tip end of the protrusion part.

6. The atomizing apparatus according to claim 1, wherein the main body part has a rectangular parallelepiped shape and has a large area to receive water by being larger in width than in thickness.

7. The atomizing apparatus according to claim 1, wherein, in the discharge electrode, the main body is elongated in an axial direction, the protrusion part protrudes at a right angle to the axial direction of the main body part from a middle in the axial direction of the main body part, and the protrusion part is shorter than a length in the axial direction of the main body part.

8. The atomizing apparatus according to claim 1, wherein a foam metal with a three-dimensional net structure, with a pore diameter of 10 to 800 μm and a voidage of 60 to 90% is used for the main body part.

9. An air conditioner comprising:
   a heat exchanger;
   an air suction port provided before or above the heat exchanger;
   a blower for blowing air taken in from the air suction port and heat exchanged by the heat exchanger, from an air outlet;
   a filter that is provided between the air suction port and the heat exchanger;
   a drain pan provided in a lower part of the heat exchanger; and
   the atomizing apparatus according to claim 1, the atomizing apparatus being placed downstream of the filter and above the drain pan.

10. The air conditioner according to claim 9, wherein the mist generated by the atomizing apparatus is supplied to a room into which a mist spray outlet opens from the